United States Patent
Wang et al.

(10) Patent No.: US 11,492,360 B2
(45) Date of Patent: Nov. 8, 2022

(54) ORGANIC COMPOUND AND ELECTROLUMINESCENT DEVICE CONTAINING THE SAME

(71) Applicant: BEIJING SUMMER SPROUT TECHNOLOGY CO., LTD., Beijing (CN)

(72) Inventors: Tao Wang, Beijing (CN); Zhongxun Ma, Beijing (CN); Bin Li, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 421 days.

(21) Appl. No.: 16/745,555

(22) Filed: Jan. 17, 2020

(65) Prior Publication Data

US 2020/0231602 A1 Jul. 23, 2020

(30) Foreign Application Priority Data

Jan. 18, 2019 (CN) .......................... 201910049207.0

(51) Int. Cl.
*C07D 495/04* (2006.01)
*C07D 517/04* (2006.01)
(Continued)

(52) U.S. Cl.
CPC ......... *C07D 517/04* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS 7,279,704 B2 10/2007 Walters et al.
7,968,146 B2 6/2011 Wagner et al.
(Continued)

FOREIGN PATENT DOCUMENTS

CN 101580708 A1 11/2009
CN 107922376 A 4/2018
(Continued)

OTHER PUBLICATIONS

CAS abstract of Voronov et al. Khimiya Geterotsiklicheskikh Soedinenii 1967, 6, 1003-1009. (Year: 1967).*
(Continued)

*Primary Examiner* — Robert S Loewe
(74) *Attorney, Agent, or Firm* — Sandberg Phoenix & von Gontard PC

(57) ABSTRACT

An organic compound having the structure of Formula (I), shown below, is disclosed. When used in a hole injection layer or a hole transporting layer, it can greatly improve the balance of electron holes and electron transporting of a device, thereby bringing excellent device effects, for example, improving the efficiency and lifetime of a device. At the same time, it also achieves a good effect when the organic compound having the structure of Formula (I) is used as a P-type conductive doping material in a charge generation layer of a multi-layer OLED device.

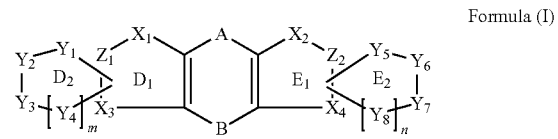

Formula (I)

20 Claims, 1 Drawing Sheet

(51) Int. Cl.
    *C07D 495/14*     (2006.01)
    *C07D 491/22*     (2006.01)
    *C07D 493/04*     (2006.01)
    *C07D 495/22*     (2006.01)
    *C07D 409/14*     (2006.01)
    *C07D 421/14*     (2006.01)
    *H01L 51/00*     (2006.01)
    *C07D 405/14*     (2006.01)

(52) U.S. Cl.
    CPC ......... *C07D 421/14* (2013.01); *C07D 491/22* (2013.01); *C07D 493/04* (2013.01); *C07D 495/04* (2013.01); *C07D 495/14* (2013.01); *C07D 495/22* (2013.01); *H01L 51/0067* (2013.01); *H01L 51/0073* (2013.01); *H01L 51/0074* (2013.01)

(56) References Cited

U.S. PATENT DOCUMENTS

2017/0069850 A1* 3/2017 Hwang ............... H01L 51/0061
2019/0013469 A1* 1/2019 Miyashita .............. H04N 5/379

FOREIGN PATENT DOCUMENTS

| JP | H09319110 A | 12/1997 |
| JP | H1026836 A | 1/1998 |
| JP | 3589796 B2 | 11/2004 |
| WO | 2011159763 A1 | 12/2011 |
| WO | 203176325 A1 | 11/2013 |
| WO | WO-2021135841 A1 * | 7/2021 ........... C07D 493/02 |

OTHER PUBLICATIONS

First Office Action Issued for Corresponding Chinese Patent Application No. 201910049207.0 dated Dec. 28, 2020.
Second Office Action Issued for Corresponding Chinese Patent Application No. 201910049207.0 dated Jun. 29, 2021.
First Office Action Issued for Corresponding Korean Patent Application No. 10-2020-0006872 dated Jun. 30, 2021.
Search Report for Chinese Application 2019100492070 dated Dec. 16, 2020.
Jiang Quan et al, Display Device Technology (2nd Edition); Beijing: National Defense Industry Press; 2014.8; ISBN 978-7-118-08076-6; Chinese Edition Library CIP Data Core (2014) No. 163317 (3 Pages).
Yoshihiro Ohba et al; Synthesis of New Type Benzo[B]Thiophene Fused Quinones and Their Tetracyanoquinodimethane Derivatives; Journal of Heterocyclic Chemistry 1997, vol. 34 (3), 781-787.

* cited by examiner

ORGANIC COMPOUND AND ELECTROLUMINESCENT DEVICE CONTAINING THE SAME

CROSS-REFERENCE TO RELATED APPLICATIONS

This application claims priority to Chinese patent application No. 201910049207.0 filed on Jan. 18, 2019, and which is incorporated herein by reference.

TECHNICAL FIELD

The present disclosure belongs to the technical field of organic electroluminescent materials, and particularly relates to an organic compound and a composition and an electroluminescent device comprising the same.

BACKGROUND

Organic light emitting diode (OLED) is a type of display unit that uses organic self-luminous phenomenon. It has excellent performances such as a wide viewing angle, being thinner than a liquid crystal display unit, emission of light with high brightness under low driving voltage, and a fast response speed. Recently, it has been highly anticipated in applications such as a full-color display unit or lighting.

Generally, an organic electroluminescent device has a structure including a positive electrode, a negative electrode, and an organic material layer therebetween. Charges are injected into the organic layer formed between the anode and cathode to form electron-hole pairs such that organic compounds with fluorescent or phosphorescent properties emit light. Because holes and electrons move at different speeds, the above-mentioned organic layer is often formed by multilayer structures composed of different materials, such as a hole injection layer, a hole transporting layer, a light emitting layer, an electron transport layer, and an electron injection layer, etc.

In OLED devices, a hole injection layer (HIL) can help holes to be injected into the organic layer from the ITO anode. In order to allow an OLED device to reach a low driving voltage, the injection energy barrier between the HIL layer and the ITO anode must be sufficiently small. There are many HIL materials that have been developed, such as some triarylamine compounds with very shallow HOMO energy levels, very electron-deficient heterocyclic compounds, and triarylamine compounds doped with P-type conductive materials.

Yoshihiro Ohba et al. reported the synthesis of compound

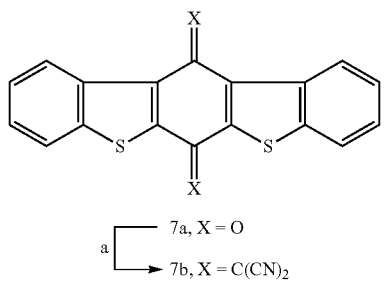

(J. Heterocyclic Chem., 34, (1997) 781-787) and focused on use of compounds 1b-8b as analogs of TCNQ. The π-conjugated system was extended by introducing thiophene-fused structures to expect to form a charge transfer complex with an electron donor compound. However, compound 7b was not successfully separated and purified, but only a mixture containing isomers was obtained, and only simple tests (CV and UV) were performed on the mixture in terms of characterization.

JP3589796B2 discloses two types of dibenzofuranquinones, the specific structures of which are

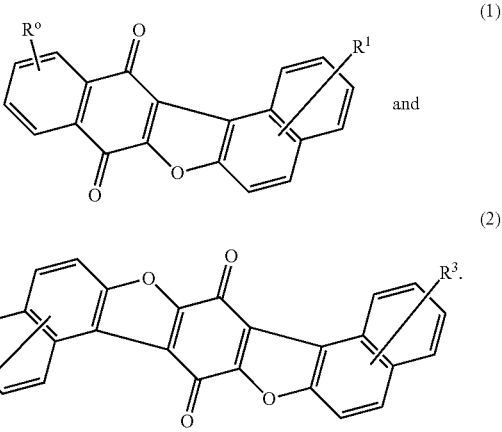

However, their performance still needs to be improved, such as they have weak hole injection ability.

There is a need in the art to develop a hole injection material that can improve the balance of electron holes and electron transporting of OLEDs, and improve the efficiency and lifetime of a device. It is critical to develop new high-performance HIL materials.

SUMMARY

One object of the present disclosure is to provide an organic compound having the structure of Formula (I):

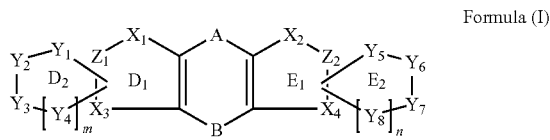

in Formula (I), A and B are each independently selected from

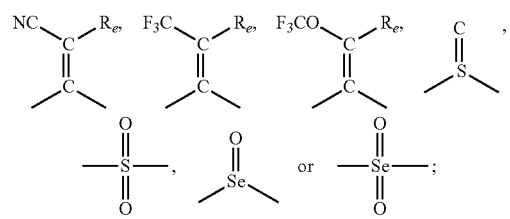

in Formula (I), $D_1$ and $E_1$ are each independently selected from any one of a five-membered unsaturated carbocyclic ring and a five-membered unsaturated heterocyclic ring;

in Formula (I), $D_2$ and $E_2$ are each independently selected from any one of a five-membered aromatic carbocyclic ring, a five-membered aromatic heterocyclic ring, a six-membered aromatic carbocyclic ring, and a six-membered aromatic heterocyclic ring, and the $D_2$ and $D_1$ are fused and share two atoms, and the $E_2$ and $E_1$ are fused and share 2 atoms;

in Formula (I), m and n are independently 0 or 1; when m is 0, $D_2$ is a five-membered ring; when m is 1, $D_2$ is a six-membered ring; when n is 0, $E_2$ is a five-membered ring; and when n is 1, $E_2$ is a six-membered ring;

in Formula (I), $X_1$, $X_2$, $X_3$, and $X_4$ are each independently selected from any one of C, $C(R_1)(R_2)$, $N(R_1)$, O, $Si(R_1)(R_2)$, S, S=O, $S(=O)_2$, Se, Se=O, and $Se(=O)_2$;

in Formula (I), $Y_1$, $Y_2$, $Y_3$, $Y_4$, $Y_5$, $Y_6$, $Y_7$, and $Y_8$ are each independently selected from any one of $CR_b$, $CR_a$, N, and $NR_b$, and at least one of $Y_1$, $Y_2$, $Y_3$, $Y_4$, $Y_5$, $Y_6$, $Y_7$, and $Y_8$ is selected from $CR_a$;

the $R_a$ is an electron-withdrawing group; and the $R_e$, $R_1$, $R_2$ and $R_b$ are each independently selected from any one or a combination of at least two of hydrogen, deuterium, halogen, a substituted or unsubstituted alkyl group having 1-20 carbon atoms, a substituted or unsubstituted cycloalkyl group having 3-20 cyclic carbon atoms, a substituted or unsubstituted heteroalkyl group having 1-20 carbon atoms, a substituted or unsubstituted aralkyl having 7-30 carbon atoms, a substituted or unsubstituted alkoxyl group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amine group having 0-20 carbon atoms, a substituted or unsubstituted acyl group having 0-20 carbon atoms, a substituted or unsubstituted carbonyl group having 0-20 carbon atoms, a substituted or unsubstituted carboxylic group having 0-20 carbon atoms, a substituted or unsubstituted ester group having 0-20 carbon atoms, a substituted or unsubstituted nitrile group having 0-20 carbon atoms, a substituted or unsubstituted isonitrile group having 0-20 carbon atoms, a substituted or unsubstituted sulfanyl group having 0-20 carbon atoms, a substituted or unsubstituted sulfinyl group having 0-20 carbon atoms, a substituted or unsubstituted sulfonyl having 0-20 carbon atoms, and a substituted or unsubstituted phosphino group having 0-20 carbon atoms.

A second object of the present disclosure is to provide a composition, which comprises the organic compound as described in the first object and at least one material.

A third object of the present disclosure is to provide an electroluminescent device comprising an anode, a cathode, and an organic layer disposed between the anode and the cathode, wherein the organic layer contains the organic compound as described in the first object.

Compared with the prior art, the present disclosure has the following beneficial effects:

When used in a hole injection layer or a hole transporting layer, the organic compound having the structure of Formula (I) provided in the present disclosure can greatly improve the balance of electron holes and electron transporting of a device, thereby bringing excellent device effects, for example, improving the efficiency and lifetime of the device. At the same time, it also achieves a good effect when the organic compound having the structure of Formula (I) is used as a P-type conductive doping material in the charge generation layer of a multi-layer OLED device.

DETAILED DESCRIPTION

Figure 1:
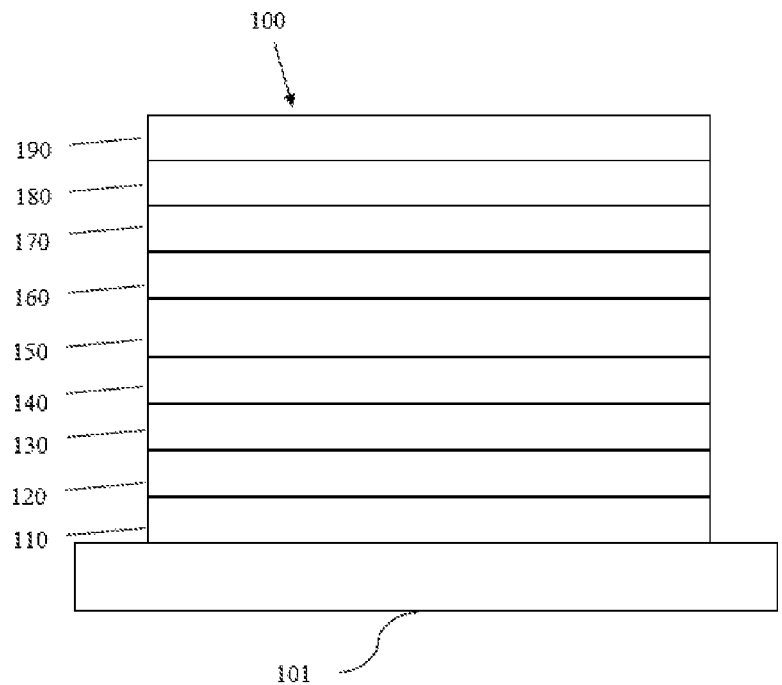
FIG. 1 shows a structural schematic diagram of the organic light-emitting device 100.

The technical solutions of the present disclosure will be further described below by way of specific embodiments. It will be apparent to those skilled in the art that the embodiments are merely illustrations of the present disclosure and should not be construed as specific limitations to the present disclosure.

In a specific embodiment, an organic compound is provided in the present disclosure, wherein the organic compound has the structure of Formula (I):

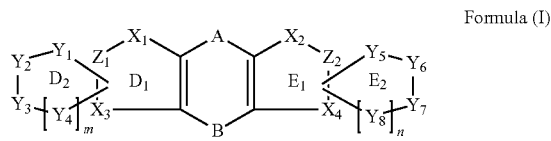

Formula (I)

in Formula (I), A and B are each independently selected from

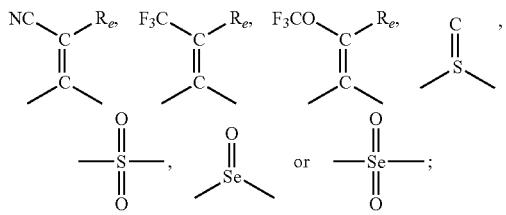

in Formula (I), $D_1$ and $E_1$ are each independently selected from any one of a five-membered unsaturated carbocyclic ring and a five-membered unsaturated heterocyclic ring;

in Formula (I), $D_2$ and $E_2$ are each independently selected from any one of a five-membered aromatic carbocyclic ring, a five-membered aromatic heterocyclic ring, a six-membered aromatic carbocyclic ring, and a six-membered aromatic heterocyclic ring, and the $D_2$ and $D_1$ are fused and share two atoms, and the $E_2$ and $E_1$ are fused and share 2 atoms;

in Formula (I), m and n are independently 0 or 1; when m is 0, $D_2$ is a five-membered ring; when m is 1, $D_2$ is a six-membered ring; when n is 0, $E_2$ is a five-membered ring; and when n is 1, $E_2$ is a six-membered ring;

$Z_1$ and $Z_2$ are C;

in Formula (I), $X_1$, $X_2$, $X_3$, and $X_4$ are each independently selected from any one of C, $C(R_1)(R_2)$, $N(R_1)$, O, $Si(R_1)(R_2)$, S, S=O, $S(=O)_2$, Se, Se=O, and $Se(=O)_2$;

in Formula (I), $Y_1$, $Y_2$, $Y_3$, $Y_4$, $Y_5$, $Y_6$, $Y_7$, and $Y_8$ are each independently selected from any one of $CR_b$, $CR_a$, N, and $NR_b$, and at least one of $Y_1$, $Y_2$, $Y_3$, $Y_4$, $Y_5$, $Y_6$, $Y_7$, and $Y_8$ is selected from $CR_a$;

the $R_a$ is an electron-withdrawing group; and the $R_e$, $R_1$, $R_2$ and $R_b$ are each independently selected from any one or a combination of at least two of hydrogen, deuterium, halogen, a substituted or unsubstituted alkyl group having 1-20 carbon atoms, a substituted or unsubstituted cycloalkyl group having 3-20 cyclic carbon atoms, a substituted or unsubstituted heteroalkyl group having 1-20 carbon atoms, a substituted or unsubstituted aralkyl having 7-30 carbon atoms, a substituted or unsubstituted alkoxyl group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amine group having 0-20 carbon atoms, a substituted or unsubstituted acyl group having 0-20 carbon atoms, a substituted or unsubstituted carbonyl group having 0-20 carbon atoms, a substituted or unsubstituted carboxylic group having 0-20 carbon atoms, a substituted or unsubstituted ester group having 0-20 carbon atoms, a substituted or unsubstituted nitrile group having 0-20 carbon atoms, a substituted or unsubstituted isonitrile group having 0-20 carbon atoms, a substituted or unsubstituted sulfanyl group having 0-20 carbon atoms, a substituted or unsubstituted sulfinyl group having 0-20 carbon atoms, a substituted or unsubstituted sulfonyl having 0-20 carbon atoms, a substituted or unsubstituted amine group having 0-20 carbon atoms, and a substituted or unsubstituted phosphino group having 0-20 carbon atoms; and any two adjacent substituents are optionally joined to form a ring.

In the above selection range of $R_e$, $R_1$, $R_2$ and $R_b$, the substituents for substitution may be selected from one of deuterium, halogen, cyano, C1-C10 alkyl, C1-C10 cycloalkyl, C2-C6 alkenyl, C2-C6 cycloalkenyl, C1-C6 alkoxyl, C1-C6 thioalkoxyl, C6-C30 monocyclic aryl, C6-C30 fused cyclic aryl, C3-C30 monocyclic heteroaryl, and C3-C30 fused cyclic heteroaryl.

In the structure of Formula (I) in the present disclosure, if $X_1$, $X_2$, $X_3$ and $X_4$ are optionally C, it can be understood that fuse occurs at said position.

"Any two adjacent substituents can be optionally joined to form a ring" refers to that any two adjacent $R_e$, $R_1$, $R_2$, $R_a$ and $R_b$ are optionally joined to form a ring. It should be noted that the optional connection of any two adjacent substituents to form a ring is an optional technical solution, and the $R_e$, $R_1$, $R_2$, $R_a$, and $R_b$ may not form a ring.

When used in an electroluminescent device, the compound provided by the present disclosure can extend the service life of the device and improve the luminous efficiency. The technical effect can obviously reflect the results. The inventor speculates that the principle to obtain the above effect is that: the A and B groups are selected to be electron-withdrawing groups, cooperating with a suitable large π bond, and an electron-withdrawing group that cooperates with it is connected at the farthest end such that holes can be effectively extracted, thereby improving the luminous efficiency and extending the service life.

When $R_a$ in the present disclosure is an electron withdrawing group, the electron withdrawing group referred to is any optional electron withdrawing group in the art.

In a specific embodiment, the compound has the structure shown in any one of Formula (II) and Formula (III):

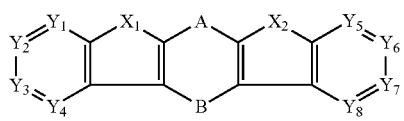

Formula (II)

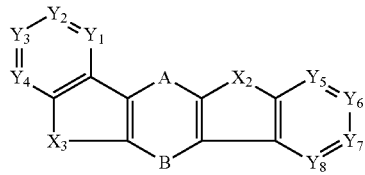

Formula (III)

in Formula (II) and Formula (III), A, B, $Y_1$, $Y_2$, $Y_3$, $Y_4$, $Y_5$, $Y_6$, $Y_7$, and $Y_8$ have the same scope as in claim 1, and $X_1$, $X_2$, $X_3$, and $X_4$ are each independently selected from any one of $C(R_1)(R_2)$, $N(R_1)$, O, $Si(R_1)(R_2)$, S, S=O, $S(=O)_2$, Se, Se=O, and $Se(=O)_2$; specifically:

A and B are each independently selected from

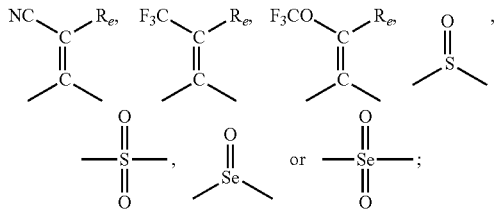

$X_1$, $X_2$, $X_3$, and $X_4$ are each independently selected from any one of $C(R_1)(R_2)$, $N(R_1)$, O, $Si(R_1)(R_2)$, S, S=O, $S(=O)_2$, Se, Se=O, and $Se(=O)_2$;

$Y_1$, $Y_2$, $Y_3$, $Y_4$, $Y_5$, $Y_6$, $Y_7$, and $Y_8$ are each independently selected from any one of $CR_b$, $CR_a$, N, and $NR_b$, and at least one of $Y_1$, $Y_2$, $Y_3$, $Y_4$, $Y_5$, $Y_6$, $Y_7$, and $Y_8$ is selected from $CR_a$;

the $R_a$ is an electron-withdrawing group; and the $R_e$, $R_1$, $R_2$ and $R_b$ are each independently selected from any one or a combination of at least two of hydrogen, deuterium, halogen, a substituted or unsubstituted alkyl group having 1-20 carbon atoms, a substituted or unsubstituted cycloalkyl group having 3-20 cyclic carbon atoms, a substituted or unsubstituted heteroalkyl group having 1-20 carbon atoms, a substituted or unsubstituted aralkyl having 7-30 carbon atoms, a substituted or unsubstituted alkoxyl group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amine group having 0-20 carbon atoms, a substituted or unsubstituted acyl group having 0-20 carbon atoms, a substituted or unsubstituted carbonyl group having 0-20 carbon atoms, a substituted or unsubstituted carboxylic group having 0-20 carbon atoms, a substituted or unsubstituted ester group having 0-20 carbon atoms, a substituted or unsubstituted nitrile group having 0-20 carbon atoms, a substituted or unsubstituted isonitrile group having 0-20 carbon atoms, a substituted or unsubstituted sulfanyl group having 0-20 carbon atoms, a substituted or unsubstituted sulfinyl group having 0-20 carbon atoms, a substituted or unsubstituted sulfonyl having 0-20 carbon atoms, and a substituted or unsubstituted phosphino group having 0-20 carbon atoms; and any two adjacent substituents are optionally joined to form a ring.

In another specific embodiment, in Formula (I), $X_1$, $X_2$, $X_3$, and $X_4$ are each independently selected from any one of C, O, S, S=O, S(=O)$_2$, Se, Se=O, and Se(=O)$_2$.

In another specific embodiment, in Formula (II) and Formula (III), $X_1$, $X_2$, $X_3$, and $X_4$ are each independently selected from any one of O, S, S=O, S(=O)$_2$, Se, Se=O, and Se(=O)$_2$.

In this specific embodiment, the cooperation of the positional relationship of the aromatic ring and the selection range of $X_1$, $X_2$, $X_3$ and $X_4$ can minimize the LUMO energy level of the compound and improve the charge mobility.

In another specific embodiment, in Formula (I), A and B are each independently selected from

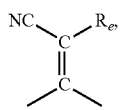

and $R_e$ is a cyano group.

In another specific embodiment, in Formula (II) and Formula (III), A and B are each independently selected from

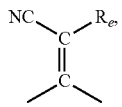

and $R_e$ is a cyano group.

In another specific embodiment, in Formula (II) and Formula (III), $X_1$, $X_2$, $X_3$, and $X_4$ are each independently selected from any one of O, S, S=O, S(=O)$_2$, Se, Se=O, and Se(=O)$_2$; and A and B are each independently selected from

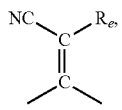

and $R_e$ is a cyano group.

The $R_a$ in the present disclosure has a Hammett substituent constant value of ≥0.3 and has a strong electron-withdrawing ability so that it can significantly reduce the LUMO energy level of the compound and achieve the effect of improving charge mobility.

It should be noted that the Hammett substituent constant value includes the Hammett substituent para constant and/or meta constant. As long as one of the para and meta constants is greater than or equal to 0.3, the group can be used as the preferred group for $R_a$ in the present disclosure.

Exemplary $R_a$ can be any one or a combination of at least two of fluorine atom, chlorine atom, bromine atom, iodine atom, nitroso, nitro, sulfate group, sulfonate group, nitrate group, trifluoromethyl group, pentafluoroethyl group, trichloromethyl group, trifluoromethoxy group, pentafluoroethoxy group, trifluoromethylthio group, pentafluoroethylthio group, sulfone group, sulfoxide group, carboxyl group, carboxylate group, aldehyde group, carbonyl group, cyano group, isocyano group, oxycyano group, thiocyano group, selenocyano group, amido group, sulfonamido group, azo group, diazo group, azide group, fluorophenyl group, pyridyl group, pyrimidinyl group, triazinyl group, and dimethyl triazinyl group, etc.

In a specific embodiment, the organic compound is selected from compound AO-1 to compound AO-164, compound AS-1 to compound AS-164, compound ASe-1 to compound ASe-164, compound BO-1 to compound BO-199, compound BS-1 to compound BS-199, compound BSe-1 to compound BSe-199. For the specific structures of compound AO-1 to compound AO-164, compound AS-1 to compound AS-164, compound ASe-1 to compound ASe-164, compound BO-1 to compound BO-199, compound BS-1 to compound BS-199, and compound BSe-1 to compound BSe-199, please refer to claim 11.

Wherein, the selection of $X_1$ and $X_2$ is given after each compound, for example:

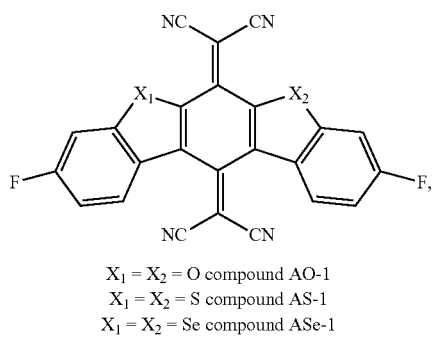

$X_1 = X_2 =$ O compound AO-1
$X_1 = X_2 =$ S compound AS-1
$X_1 = X_2 =$ Se compound ASe-1 when $X_1$ and $X_2$ are both O, it is denoted as compound AO-1; when $X_1$ and $X_2$ are both S, it is denoted as compound AS-1; and when $X_1$ and $X_2$ are both Se, it is denoted as compound ASe-1. The three schemes in which $X_1$ and $X_2$ are both O, $X_1$ and $X_2$ are both S, and $X_1$ and $X_2$ are both Se are optional parallel schemes. For example

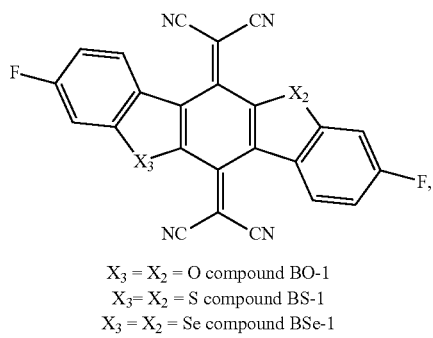

$X_3 = X_2 =$ O compound BO-1
$X_3 = X_2 =$ S compound BS-1
$X_3 = X_2 =$ Se compound BSe-1 when $X_2$ and $X_3$ are both O, it is denoted as compound BO-1; when $X_2$ and $X_3$ are both S, it is denoted as compound BS-1; and when $X_2$ and $X_3$ are both Se, it is denoted as compound BSe-1. The three schemes in which $X_2$ and $X_3$ are both O, $X_2$ and $X_3$ are both S, and $X_2$ and $X_3$ are both Se are optional parallel schemes. For the compound AO-2 to compound AO-164, compound AS-2 to compound AS-164, compound ASe-2 to compound ASe-164, compound BO-2 to compound BO-199, compound BS-2 to compound BS-199, and compound BSe-2 to compound BSe-199, the compounds of the general formula are explained as above.

In a specific embodiment, the organic compound can be partially or completely deuterated.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heteroalkyl—as used herein includes linear and branched heteroalkyl groups. Preferred heteroalkyl groups are alkyl groups that include at least one heteroatom such as nitrogen, oxygen, and sulfur. Heteroalkyl groups may also be aromatic heterocyclic groups having at least one heteroatom selected from a nitrogen atom, an oxygen atom, a sulfur atom, and a selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group. Alkylsilyl—as used herein has an alkyl-substituted silicon atom. Examples of alkylsilyl include trimethylsilyl, methylethylsilyl, triethylsilyl, methylethylpropylsilyl, and the like.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a thiolalkyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, the expression that adjacent substituents can be optionally joined to form a ring is intended to be taken to mean that two radicals are linked to each other by a chemical bond. This is illustrated by the following scheme:

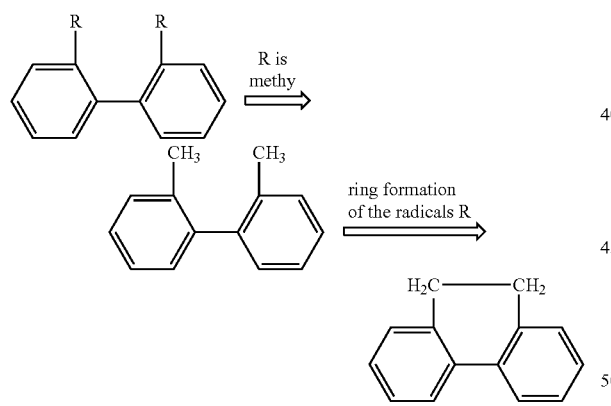

Furthermore, the expression that adjacent substituents can be optionally joined to form a ring is also intended to be taken to mean that in the case where one of the two radicals represents hydrogen, the second radical is bonded at a position to which the hydrogen atom was bonded, with formation of a ring. This is illustrated by the following scheme:

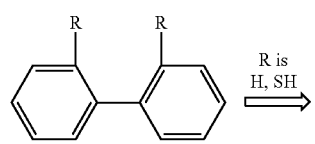

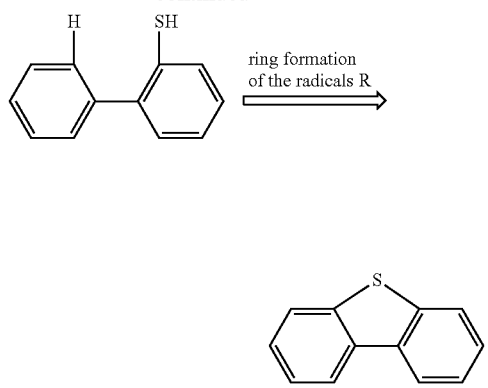

For

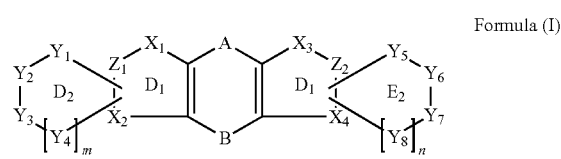

Formula (I)

provided by the present disclosure, by way of example, the present disclosure provides methods for preparing organic compound AO-22, compound BO-24, and compound BO-25, specifically as follows:

Synthesis Example 1: Synthesis of Compound AO-22

Step 1

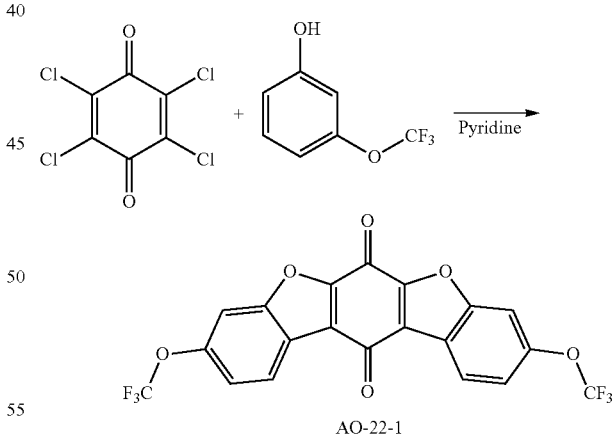

AO-22-1

In a 1 L round-bottom flask, tetrachlorobenzoquinone (5 g, 20.3 mmol), m-trifluoromethoxyphenol (7.6 g, 42.8 mmol), and pyridine (400 mL) were added. The mixture was heated under reflux in the air overnight. The reaction solution was cooled to room temperature, and water was added to separate out the precipitate. The solution was filtered, and the filter cake was washed with water until the filtrate became colorless. The solid was collected and dried to give a red solid intermediate AO-22-1 (3.1 g, 33% yield).

Step 2

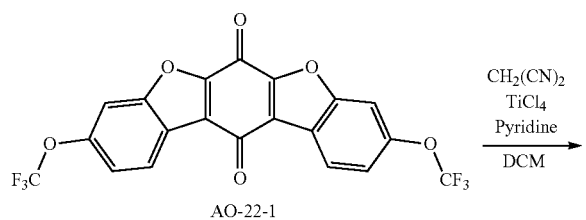

In a three-necked flask, the intermediate AO-22-1 (2.5 g, 5.5 mmol), malononitrile (1.8 g, 27.5 mmol), and DCM (350 mL) were added. The resulting solution was cooled to 0° C. with an ice water bath under nitrogen protection. Then titanium tetrachloride (6 mL, 55 mmol) was added dropwise into the reaction solution within 30 min. A solution of pyridine (8.75 mL, 110 mmol) in DCM (30 mL) was then added dropwise to the reaction solution within 1 h. Afterwards, the ice-water bath was removed and the reaction was allowed to warm up to room temperature for 30 min. The reaction was quenched with water and extracted with DCM. The organic phases were combined, washed with brine, dried over magnesium sulfate, and filtered, and the solvent was removed under reduced pressure. The obtained dark green crude product was purified by silica gel column chromatography by eluting with PE/DCM (1/1, v/v) to obtain the purple solid product AO-22 (0.5 g, 16% yield). The product was identified as the target product with a molecular weight of 552.

Synthesis Example 2: Synthesis of Organic Compound BO-24

Step 1

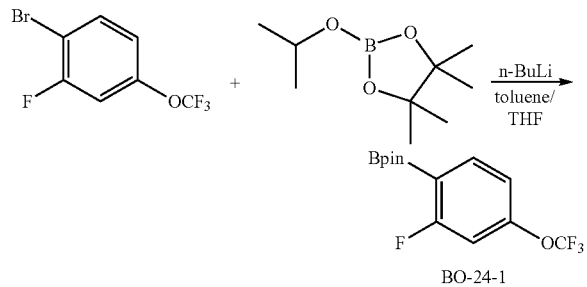

Under a nitrogen atmosphere, 1-bromo-2-fluoro-4-(trifluoromethoxy)benzene (25.9 g, 100 mmol) and isopropyl pinacol borate (22.3 g, 120 mmol) were added to toluene (160 mL) and tetrahydrofuran (40 mL), and butyllithium (75 mL, 120 mmol, 1.6M) was slowly added at −78° C. over about one hour. After the addition was completed, the reaction was warmed up to room temperature. TLC showed that the raw materials were completely converted, and then a saturated solution of ammonium chloride (200 mL) was added to quench the reaction. The layers were separated and extracted twice with dichloromethane. The organic phases were combined and dried, and the solvent was removed under reduced pressure. Then the residue was purified by column chromatography (eluent: PE 100% to PE:EA 20:1) to obtain a colorless oily intermediate BO-24-1 (33 g), which was left to stand for a period of time to become a white solid. The yield was 90%.

Step 2

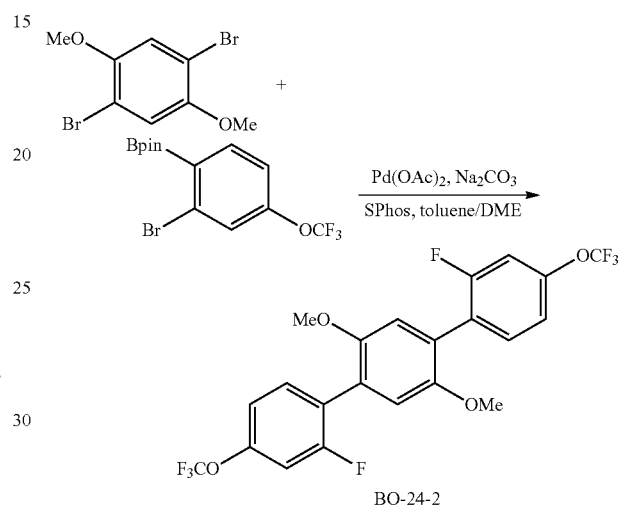

Under a nitrogen atmosphere, palladium acetate (483 mg, 2.16 mmol) and SPhos (1.8 g, 4.32 mmol) were added to toluene (160 mL) and DME (40 mL). Nitrogen was introduced for 20 minutes, and subsequently 1,4-dibromo-2,5-dimethoxybenzene (12.8 g, 43.2 mmol) and 2-(2-fluoro-4-(trifluoromethoxy)phenyl)-4,4,5,5-tetramethyl-1,3,2-dioxaborolane (33 g, 108 mmol) were added. Nitrogen was continuously introduced, and finally sodium carbonate aqueous solution (172 mL, 1M) was added, and the reaction was warmed up to 100° C. for overnight. After the raw materials were completely converted, water (200 mL) was added, and the layers were separated. The aqueous phase was extracted twice with dichloromethane. The organic phases were combined, washed with saturated brine, and dried, and the solvent was removed under reduced pressure. Then the residue was purified by column chromatography (eluent: PE:DCM 10:1) to obtain a white solid intermediate BO-24-2 (19 g) with a yield of 89%.

Step 3

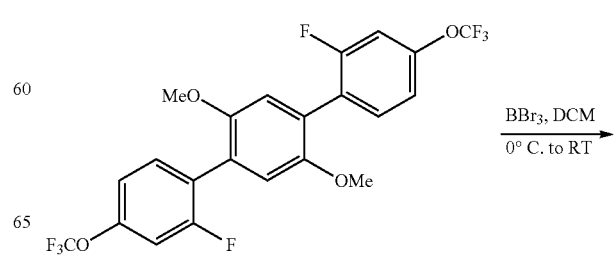

-continued

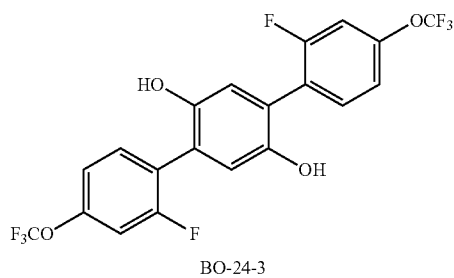

BO-24-3

Under a nitrogen atmosphere, 2,2"-difluoro-2',5'-dimethoxy-4,4"-bis(trifluoromethoxy)-1,1':4',1"-terphenyl (19 g, 38.5 mmol) was added to dried DCM (200 mL). Nitrogen was introduced for 20 minutes, and subsequently boron tribromide (28.8 g, 115 mmol) was added dropwise at 0° C. After the addition was completed, the reaction was slowly warmed up overnight. After the raw materials were completely converted, the solution was carefully quenched with water, extracted with EA, washed with brine, and dried, and the solvent was removed under reduced pressure. Then the residue was purified by column chromatography (eluent: PE:EA 10:1) to obtain a white solid, which was washed with PE and a small amount of EA to obtain 16 g of intermediate BO-24-3 with a yield of 90%.

Step 4

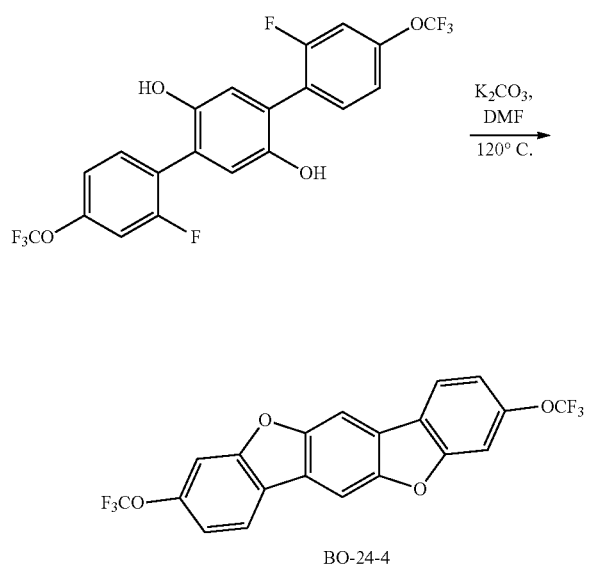

BO-24-4

Under a nitrogen atmosphere, 2,2"-difluoro-4,4"-bis(trifluoromethoxy)-[1,1':4',1"-terphenyl]-2',5'-diol (16 g, 34.6 mmol) was added to DMF (100 mL), and potassium carbonate (11.76 g, 104 mmol) was added. Nitrogen was introduced for 20 minutes, and subsequently the reaction was heated to 120° C. for overnight. After the raw materials were completely converted, the reaction solution was cooled to room temperature, and poured into water (400 mL). A large amount of white solids were precipitated. After filtration, the filter cake was washed with water and PE and fully dried to obtain the white solid intermediate BO-24-4 (11.8 g) with a yield of 80%.

Step 5

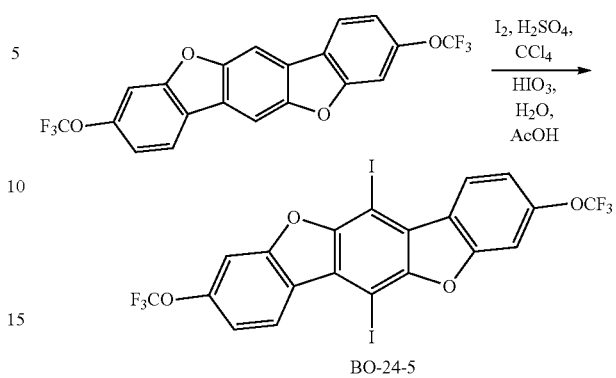

BO-24-5

The intermediate BO-24-4 (16.8 g, 40 mmol) was added to acetic acid (200 mL), and then pre-milled iodine powder (20 g, 80 mmol), iodic acid (14.2 g, 80 mmol), carbon tetrachloride (10 mL), concentrated sulfuric acid (2 mL) and distilled water (20 mL) were added, respectively. The reaction was heated to 65° C. and stirred for 48 h (opened and equipped with a tail gas treating unit). A large amount of white solids were precipitated. The reaction was cooled to room temperature, and filtered to obtain a solid, which was washed with a small amount of acetic acid, ethyl acetate and petroleum ether, respectively. Finally, it was recrystallized from toluene (800 mL) to obtain a white solid intermediate BO-24-5 (18 g) with a yield of 66%.

Step 6

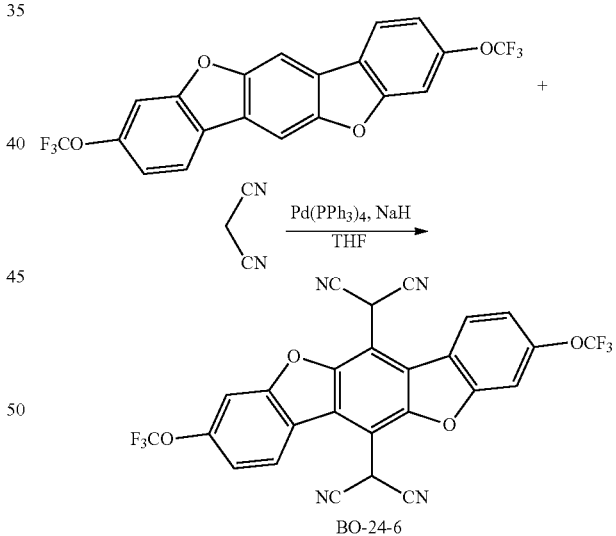

BO-24-6

Under a nitrogen atmosphere, malononitrile (2.43 g, 36.8 mmol) was added to THF (140 mL), and then sodium hydride (3 g, 73.8 mmol) was added at 0° C. The mixture was stirred for ten minutes, and then warmed up to room temperature. Under the introduction of nitrogen, intermediate BO-24-5 (10 g, 14.75 mmol) and tetrakis(triphenylphosphine)palladium (0.854 g, 0.74 mmol) were added. Nitrogen was continuously introduced for 20 minutes, and then the reaction was heated to 75° C., and a yellow solid was precipitated. After the conversion was completed, the solvent was removed, and the reaction was cooled to room temperature. 1N dilute hydrochloric acid (200 mL) was added, and a large amount of solids were precipitated. After filtration, the filter cake was washed with a small amount of water and petroleum ether, and then dried to obtain a yellow solid intermediate BO-24-6, which was used directly in the next step without further purification.

Step 7

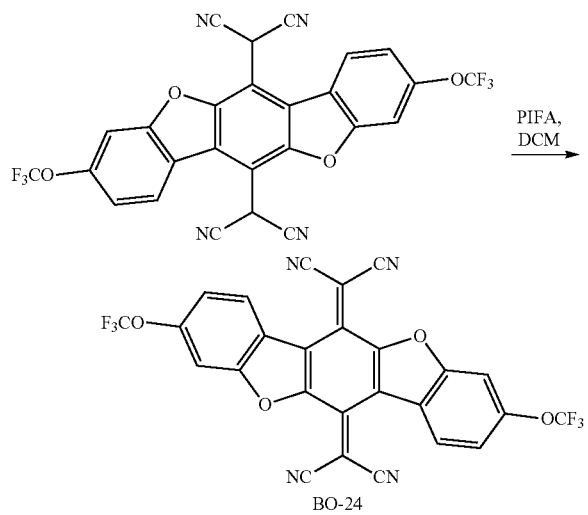

Under a nitrogen atmosphere, the intermediate BO-24-6 obtained in the previous step was added to DCM (200 mL). Nitrogen was introduced for 20 minutes, and then PIFA (7 g, 16.23 mmol) was added. The mixture was stirred at room temperature overnight. The solution was black. After the raw materials were completely converted, the mixture was directly purified by column chromatography (eluent: a gradient of PE:DCM 2:1 to 1:2). Then the solid was dissolved in a small amount of DCM and washed with n-hexane to obtain a dark brown solid compound BO-24 (7.5 g) with a yield of 90%.

The product was identified as the target product with a molecular weight of 552. Based on the mass spectrometry results of the compound, a peak at M/Z=552 was confirmed.

Synthesis Example 3: Synthesis of Compound BO-25

Step 1

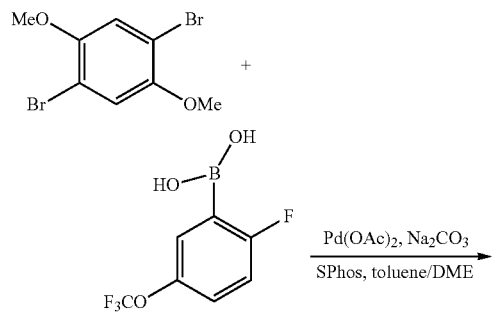

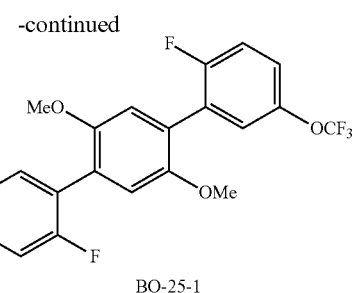

Under a nitrogen atmosphere, palladium acetate (190 mg, 0.85 mmol) and SPhos (693 mg, 1.69 mmol) were added to toluene (40 mL) and DME (10 mL). Nitrogen was introduced for 20 minutes, and subsequently 1,4-dibromo-2,5-dimethoxybenzene (5.0 g, 16.9 mmol) and 2-fluoro-5-(trifluoromethoxy)phenylboronic acid (9.5 g, 42.4 mmol) were added. Nitrogen was continuously introduced, and finally sodium carbonate aqueous solution (60 mL, 1 M) was added. The reaction was warmed up to 100° C. for overnight. After the raw materials were completely converted, water (150 mL) was added, and the layers were separated. The aqueous phase was extracted twice with dichloromethane. The organic phases were combined, washed with saturated brine, and dried, and the solvent was removed under reduced pressure. Then the residue was purified by column chromatography (eluent: PE:DCM 10:1). A white solid intermediate BO-25-1 (7.5 g) was obtained with a yield of 90%.

Step 2

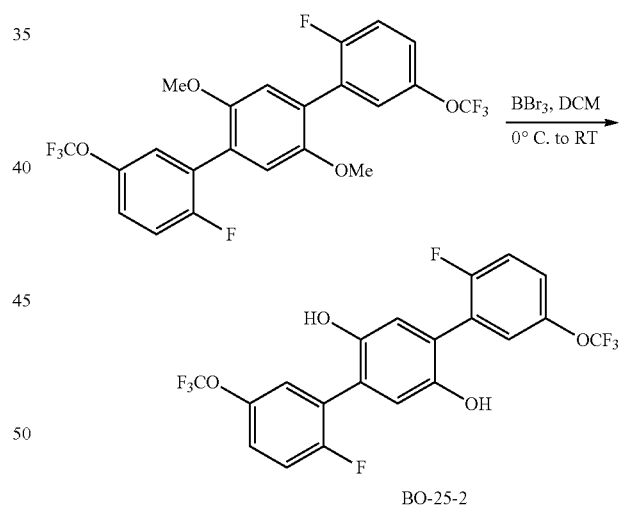

Under a nitrogen atmosphere, 2,2"-difluoro-2',5'-dimethoxy-5,5"-bis(trifluoromethoxy)-1,1':4',1"-terphenyl (7.5 g, 15.2 mmol) was added to dried DCM (80 mL). Nitrogen was introduced for 20 minutes, and subsequently boron tribromide (11.5 g, 46.0 mmol) was added dropwise at 0° C. After the addition was completed, the reaction was slowly warmed up to room temperature for overnight. After the raw materials were completely converted, the solution was carefully quenched with water and extracted with EA, then the organic phases were combined, washed with brine, and dried, and the solvent was removed under reduced pressure. Then the residue was purified by column chromatography (eluent: PE:EA 10:1) to obtain a white solid, which was washed with PE and a small amount of EA to obtain 6.5 g of intermediate BO-25-2 with a yield of 91%.

Step 3

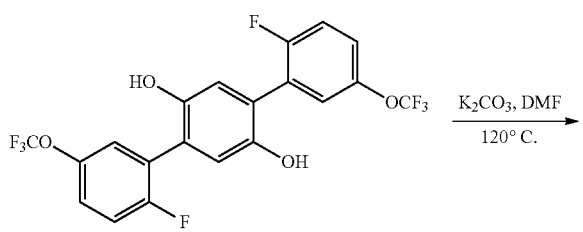

Under a nitrogen atmosphere, 2,2''-difluoro-5,5''-bis(trifluoromethoxy)-[1,1':4',1''-terphenyl]-2',5'-diol (6 g, 14.1 mmol) was added to DMF (40 mL), and potassium carbonate (4.78 g, 42.3 mmol) was added. Nitrogen was introduced for 20 minutes, and subsequently the reaction was heated to 120° C. for overnight. After the raw materials were completely converted, the reaction solution was cooled to room temperature, and poured into water (100 mL). A large amount of white solids were precipitated. After filtration, the solid was washed with water and PE and fully dried to obtain the white solid intermediate BO-25-3 (5.1 g) with a yield of 85%.

Step 4

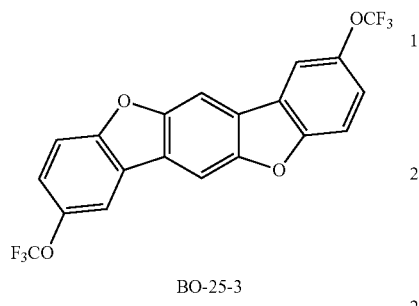

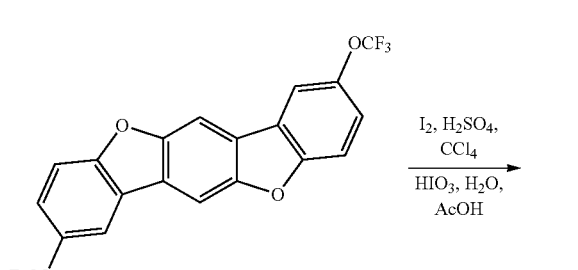

The intermediate BO-25-3 (5.1 g, 12.1 mmol) was added to acetic acid (60 mL), and then pre-milled iodine powder (6.1 g, 25 mmol), iodic acid (4.3 g, 25 mmol), carbon tetrachloride (1 mL), concentrated sulfuric acid (0.5 mL) and distilled water (6 mL) were added, respectively. The reaction was heated to 85° C. and stirred for 72 h (opened and equipped with a tail gas treating unit). A large amount of white solids were precipitated. The reaction was cooled to room temperature, and filtered to obtain a solid, which was washed with a small amount of acetic acid, ethyl acetate and petroleum ether, respectively. Afterwards, it was recrystallized from toluene (300 mL) to obtain a white solid intermediate BO-25-4 (4.9 g, 60% yield).

Step 5

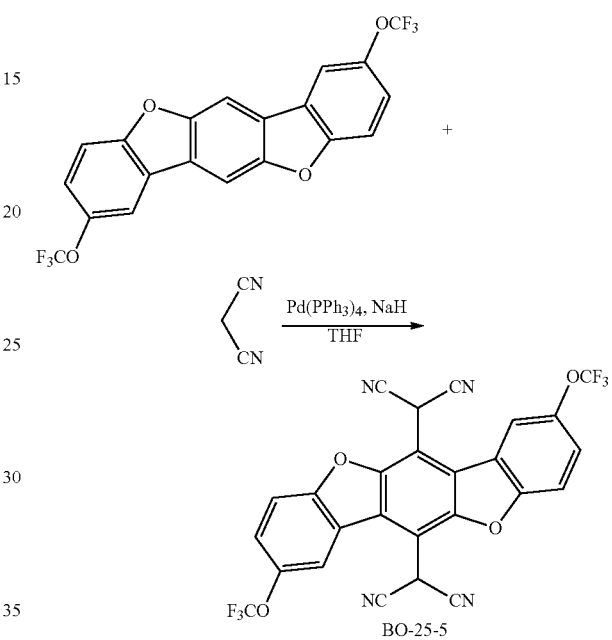

Under a nitrogen atmosphere, malononitrile (1.2 g, 18 mmol) was added to THF (70 mL), and then sodium hydride (1.47 g, 36.2 mmol) was added at 0° C. The mixture was stirred for ten minutes, and then warmed up to room temperature. Under the introduction of nitrogen, BO-25-4 (4.9 g, 7.24 mmol) and tetrakis(triphenylphosphine)palladium (0.418 g, 0.36 mmol) were added. Nitrogen was continuously introduced for 20 minutes, then the reaction was heated to 75° C., and a yellow solid was precipitated. After the conversion was completed, the solvent was removed, and the reaction was cooled to room temperature. 3 N dilute hydrochloric acid (50 mL) was added, and a large amount of solids were precipitated. After filtration, the filter cake was washed with a small amount of water and petroleum ether, and then dried to obtain a yellow solid intermediate BO-25-5 (3.6 g, 91% yield).

Step 6

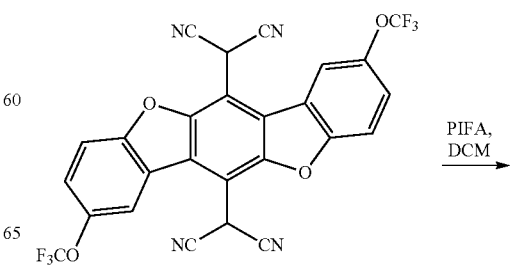

-continued

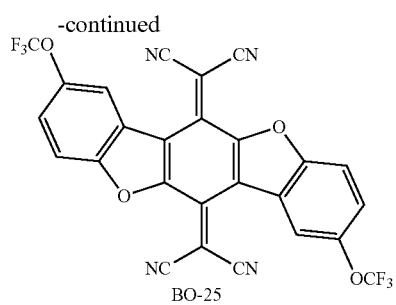

BO-25

Under a nitrogen atmosphere, the BO-25-5 obtained in the previous step was added to DCM (200 mL). Nitrogen was introduced for 20 minutes, and then PIFA (3.5 g, 8 mmol) was added. The mixture was stirred at room temperature overnight. The solution was black. After the raw materials were completely converted, the mixture was directly purified by column chromatography (eluent: a gradient of PE:DCM 2:1 to 1:2). Then the resulting solid was dissolved in a small amount of DCM and washed with n-hexane and toluene to obtain a red solid compound BO-25 (3.2 g) with a yield of about 90%.

The product was identified as the target product with a molecular weight of 552. Based on the mass spectrometry results of the compound, a peak at M/Z=552 was confirmed.

Synthesis Comparative Example: Synthesis of Comparative Compound 1

Step 1: Synthesis of Intermediate a

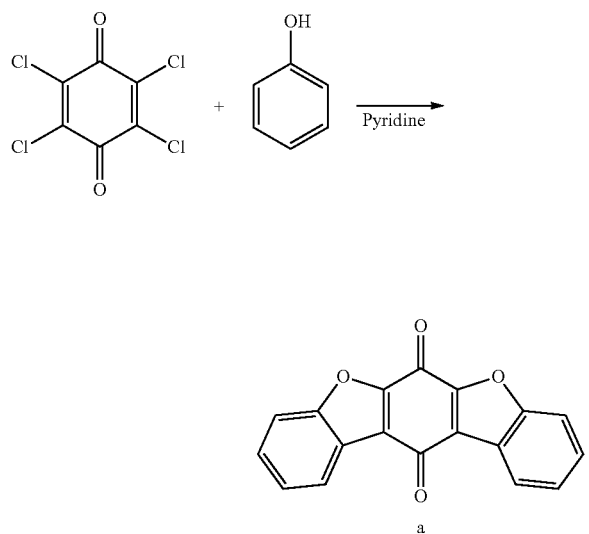 [SMILES: O=C1C(Cl)=C(Cl)C(=O)C(Cl)=C1Cl ; Oc1ccccc1 ; O=C1c2oc3ccccc3c2C(=O)c2c1oc1ccccc21]

a

In a 1 L round bottom flask, tetrachlorobenzoquinone (5 g, 20.3 mmol), phenol (3.8 g, 40.6 mmol) and pyridine (400 mL) were added. The mixture was heated under reflux in the air overnight. The reaction solution was cooled to room temperature, and water was added to separate out the precipitate. The solution was filtered, and the filter cake was washed with water until the filtrate became colorless. The solid was collected and dried to give a red solid intermediate a (2.9 g, 49% yield).

Step 2: Synthesis of Comparative Compound 1

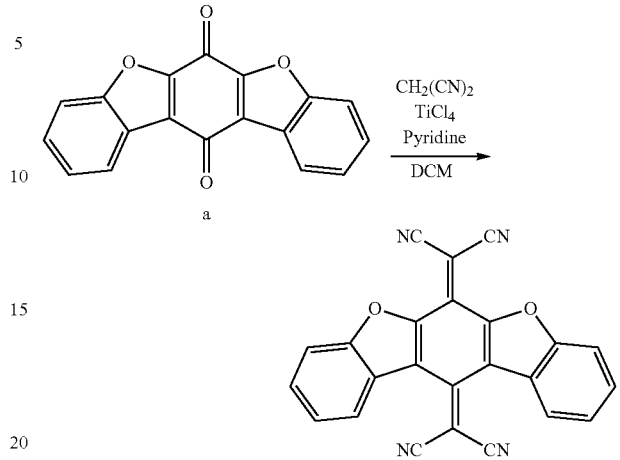

In a three-necked flask, the intermediate a (2.5 g, 8.7 mmol), malononitrile (2.8 g, 43.4 mmol), and DCM (350 mL) were added. The resulting solution was cooled to 0° C. with an ice water bath under nitrogen protection. Then titanium tetrachloride (9.5 mL, 87 mmol) was added dropwise into the reaction solution within 30 min. A solution of pyridine (14 mL, 174 mmol) in DCM (30 mL) was then added dropwise to the reaction solution within 1 h. Afterwards, the ice-water bath was removed and the reaction was allowed to warm up to room temperature for 30 min. The reaction was quenched with water and extracted with DCM. The organic phases were combined, washed with brine, dried over magnesium sulfate, and filtered, and the solvent was removed under reduced pressure. The obtained dark green crude product was purified by silica gel column chromatography by eluting with PE/DCM (1/1, v/v) to obtain the purple solid comparative compound 1 (0.46 g, 15% yield). The product was identified as the target product with a molecular weight of 384.

Based on the same inventive concept, the present disclosure also provides a composition, which comprises an organic compound as described above and at least one material.

Preferably, the composition comprises an organic compound as described above and at least one aromatic amine compound.

Based on the same inventive concept, the present disclosure also provides an electroluminescent device, which includes an anode, a cathode, and an organic layer disposed between the anode and the cathode, wherein the organic layer contains the organic compound as described above.

In a specific embodiment, the organic layer comprises at least one or two layers of a hole injection layer and a hole transporting layer.

Exemplary thicknesses of the hole injection layer and the hole transporting layer according to the present disclosure may independently be 100-400 angstroms, such as 100 angstroms, 250 angstroms, 300 angstroms, 350 angstroms, 400 angstroms, etc.

In yet another specific embodiment, the hole injection layer includes an organic compound as described above and at least one material.

In yet another specific embodiment, the hole injection layer includes an organic compound as described above and at least one aromatic amine compound.

In a specific embodiment, the hole transporting layer includes an organic compound as described above and at least one material.

In a specific embodiment, the hole transporting layer includes an organic compound as described above and at least one aromatic amine compound.

The aromatic amine compound according to the present disclosure exemplarily has the structure of Formula (VI):

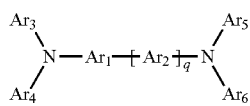

Formula VI wherein, $Ar_1$, $Ar_2$, $Ar_3$, $Ar_4$, $Ar_5$ and $Ar_6$ are each independently selected from a substituted or unsubstituted aryl group having 6-30 carbon atoms or a substituted or unsubstituted heteroaryl group having 3-30 carbon atoms;

q is an integer from 0 to 10; preferably an integer from 0 to 5; further preferably 0, 1, 2, or 3; and wherein, $Ar_1$ and $Ar_2$, $Ar_1$ and $Ar_3$, $Ar_1$ and $Ar_4$, $Ar_3$ and $Ar_4$, $Ar_2$ and $Ar_5$, $Ar_2$ and $Ar_6$ and $Ar_5$ and $Ar_6$ are each optionally connected to each other.

The aromatic amine compound according to the present disclosure is selected from the group consisting of the following compounds:

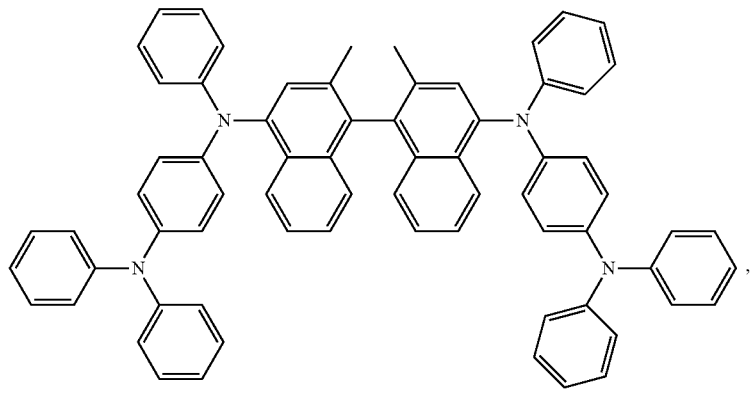

,

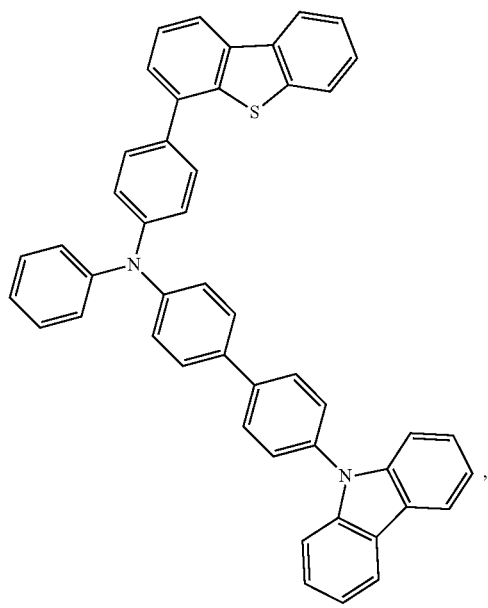

,

-continued
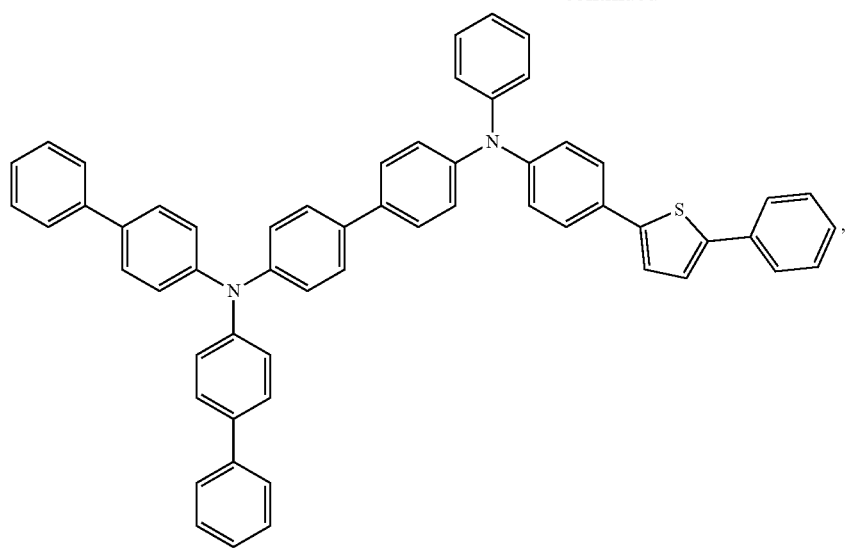
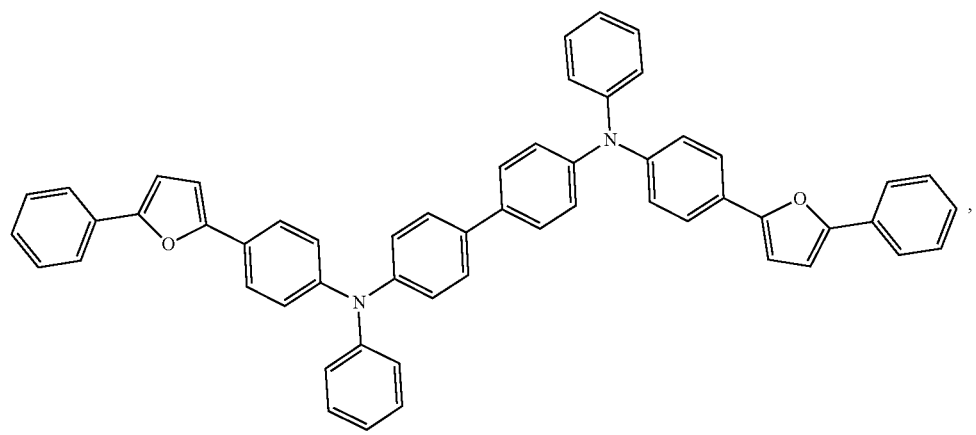
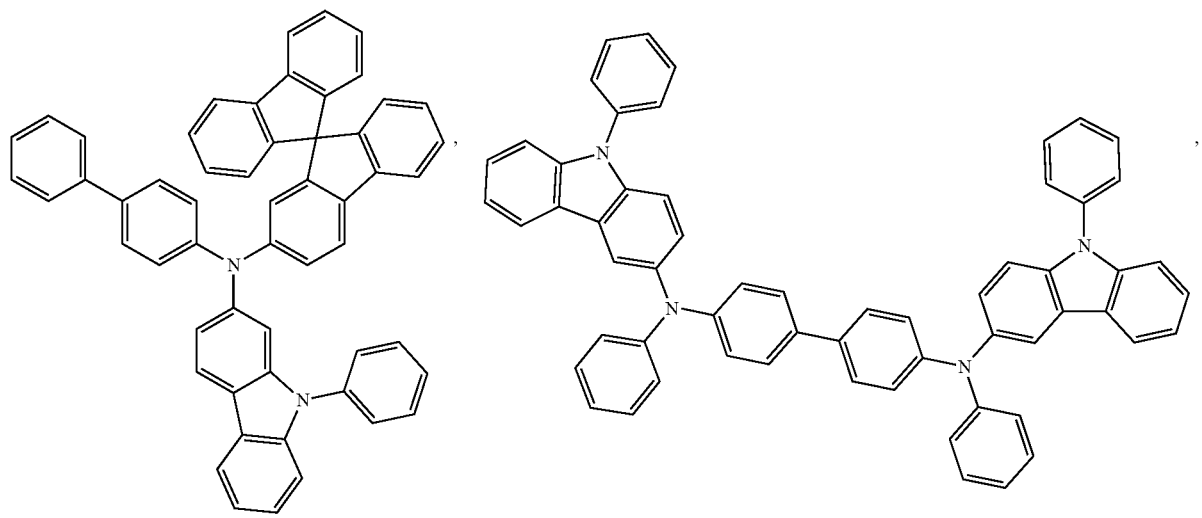

-continued
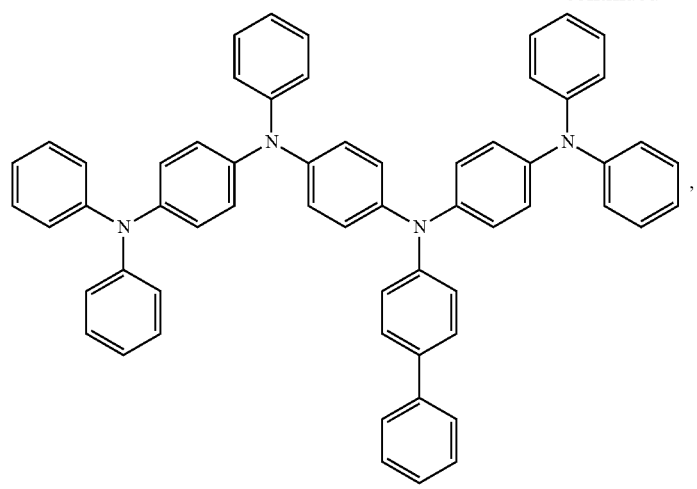
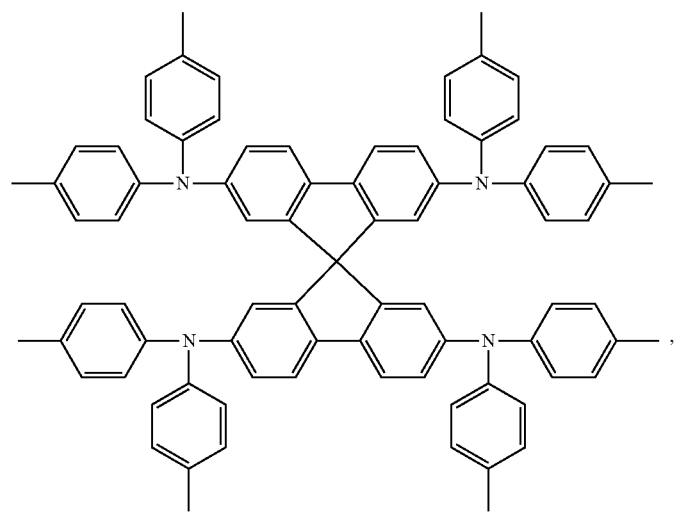
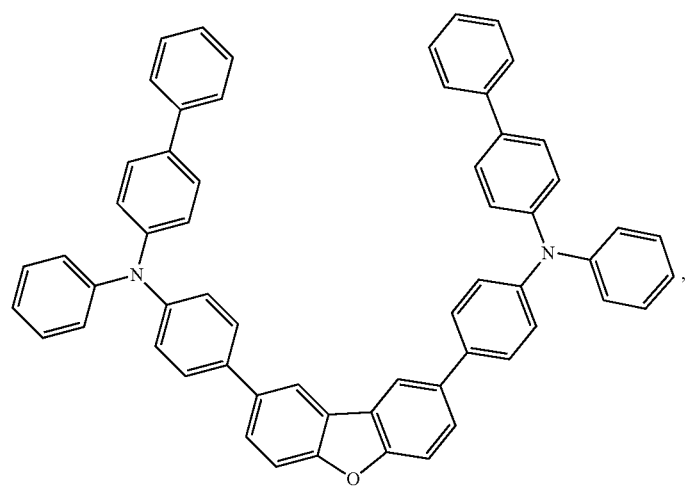

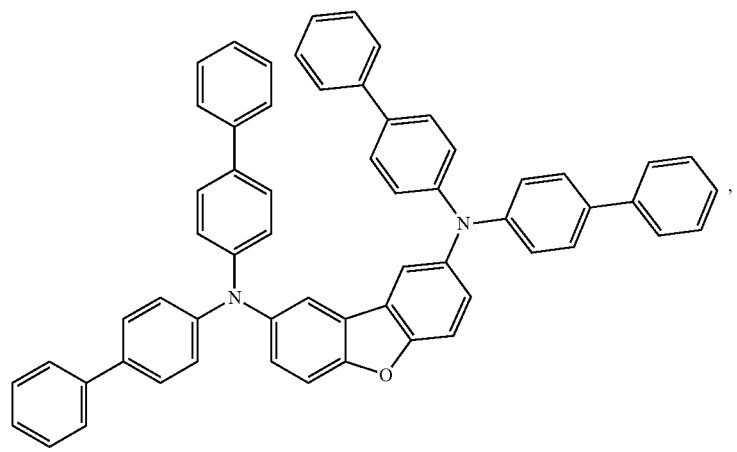
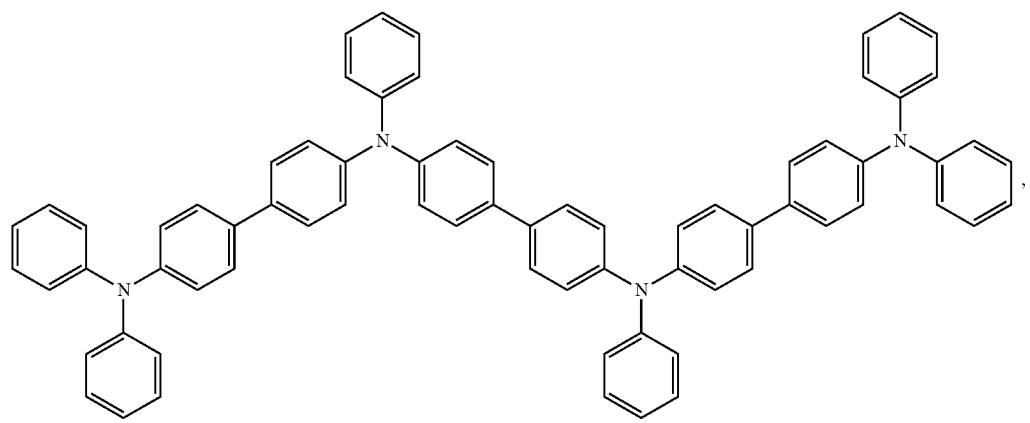
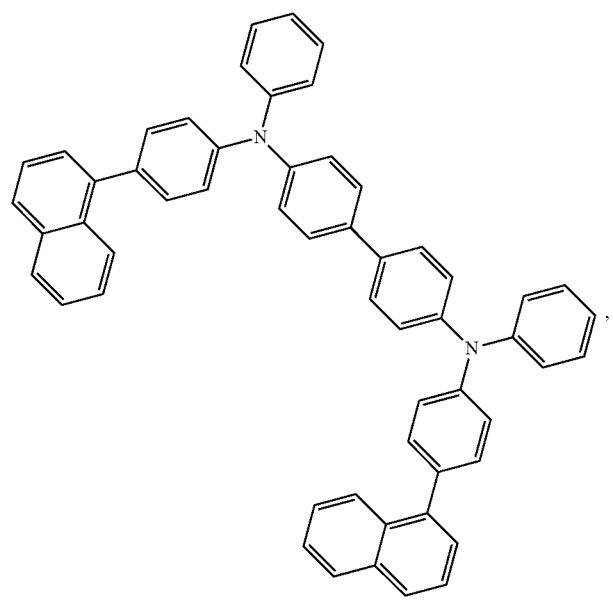

-continued
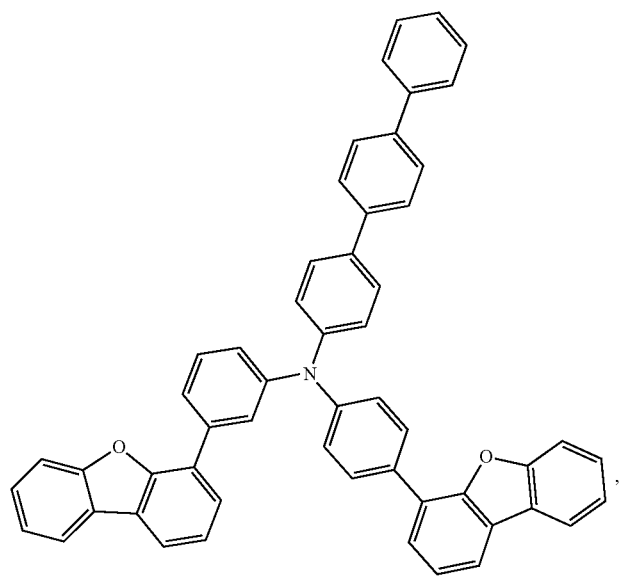
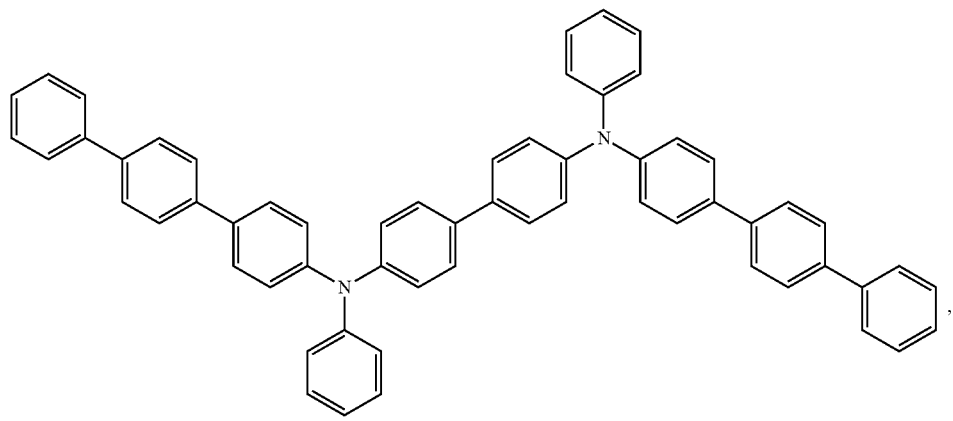
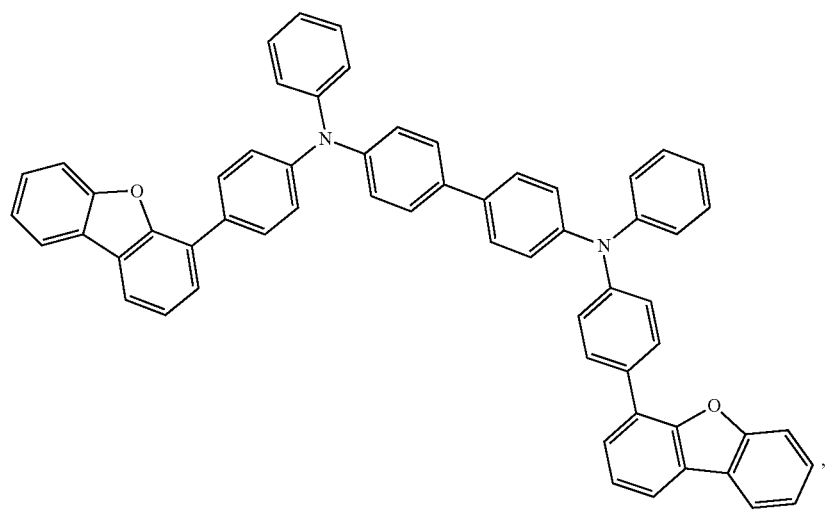

-continued
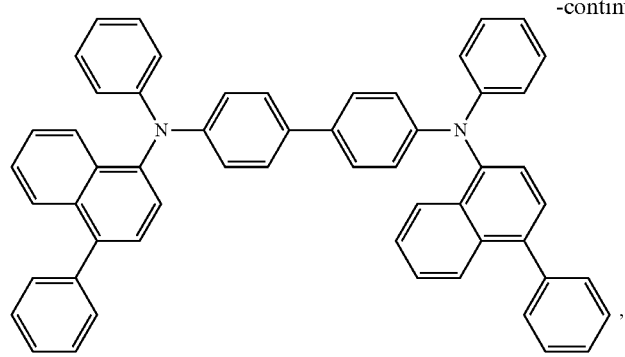
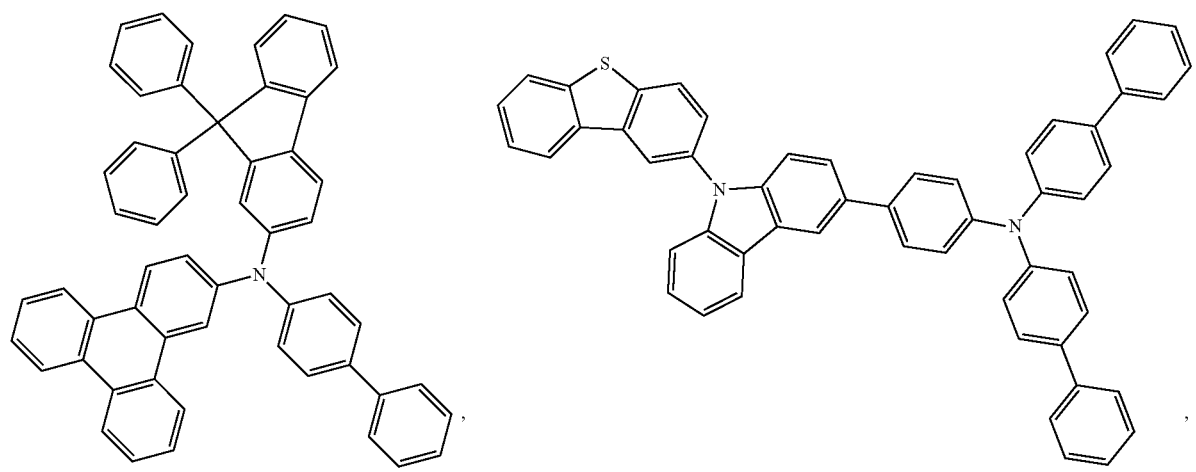
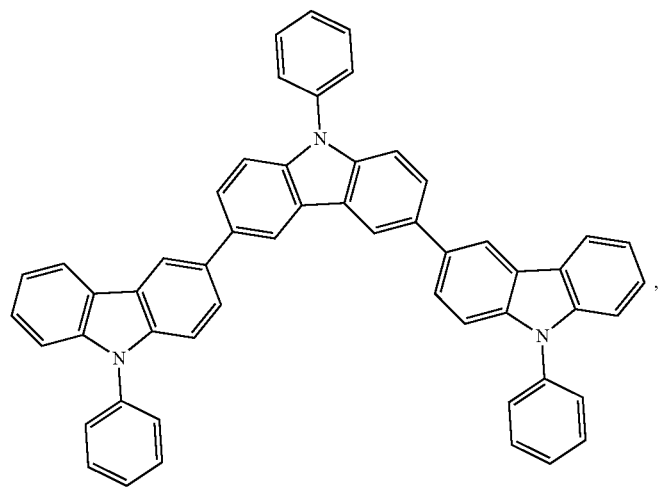

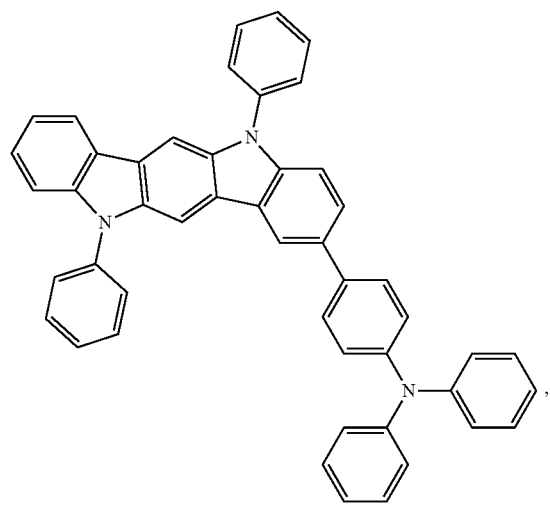
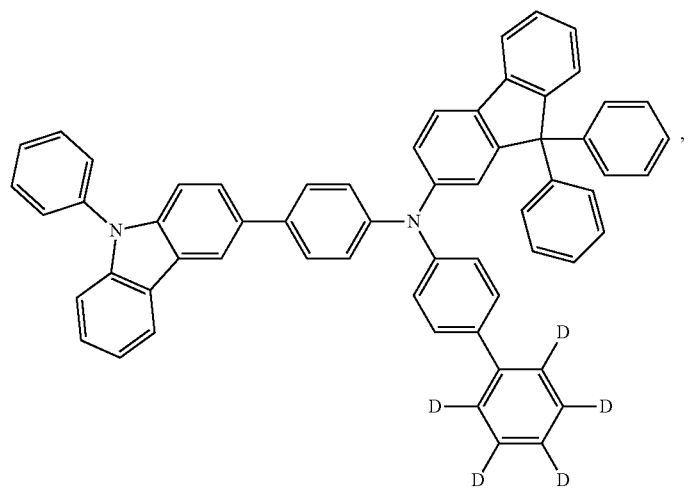
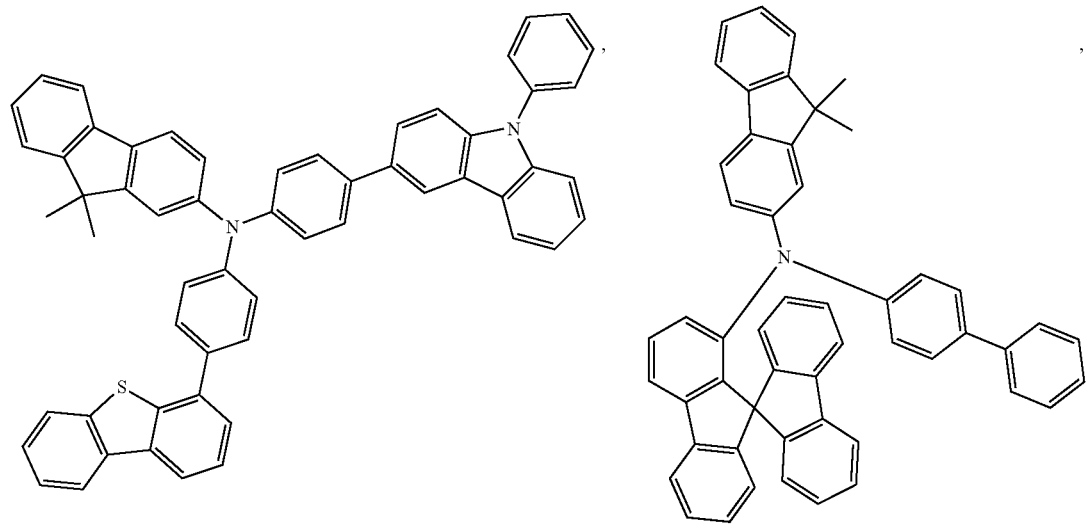

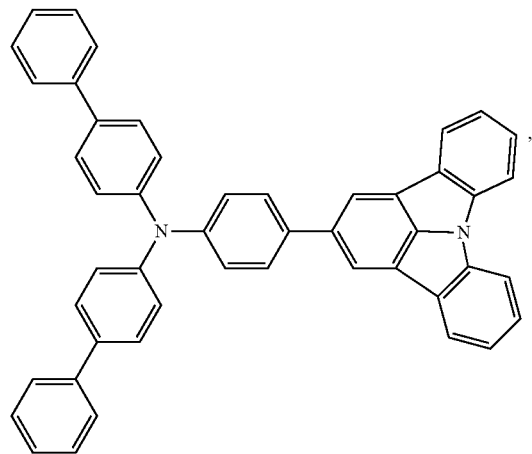
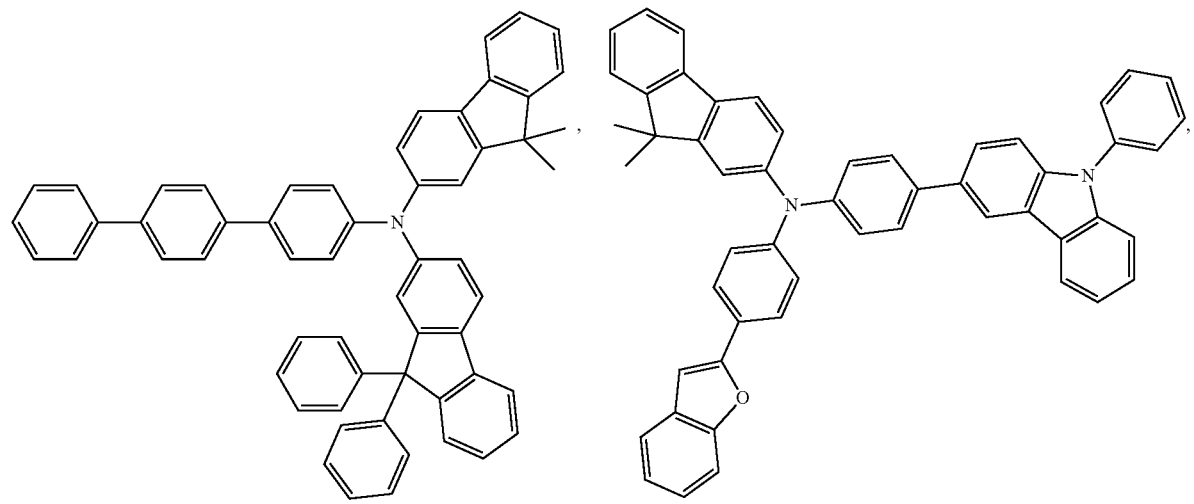
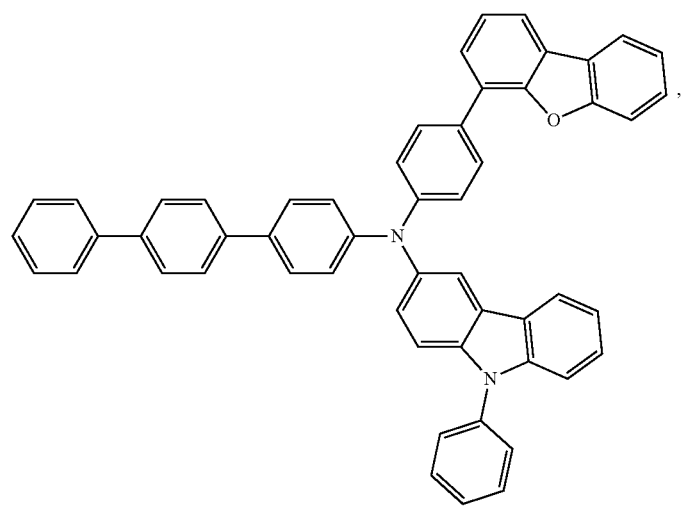

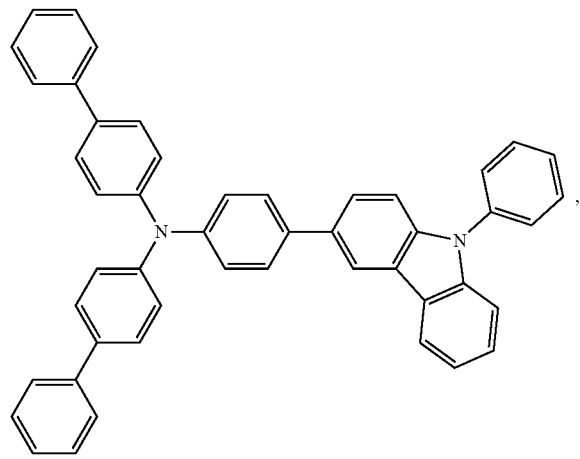
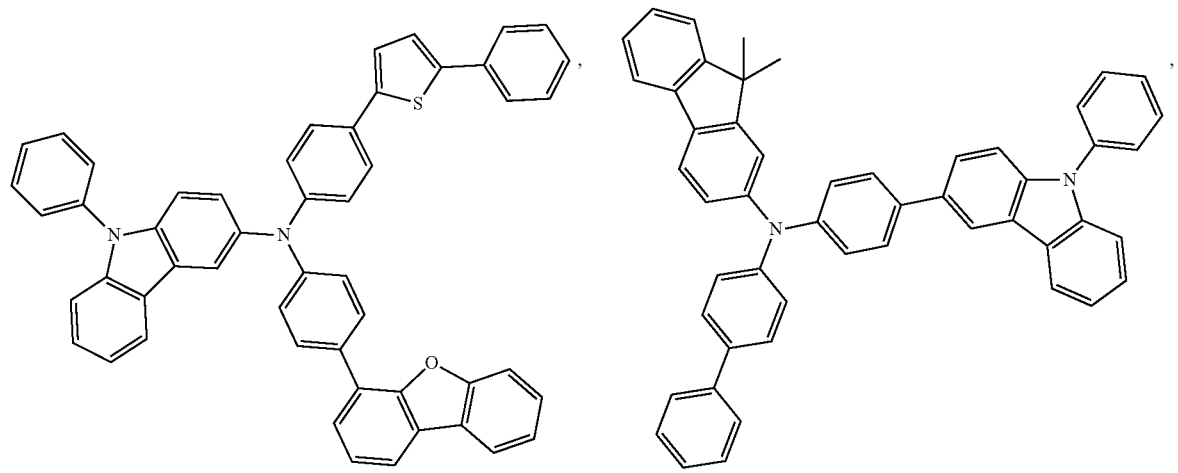
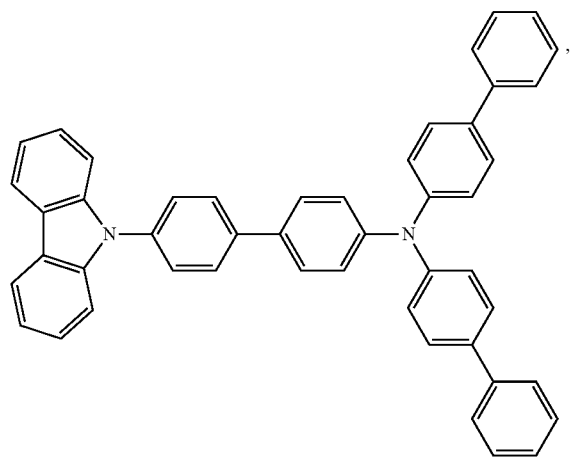

-continued

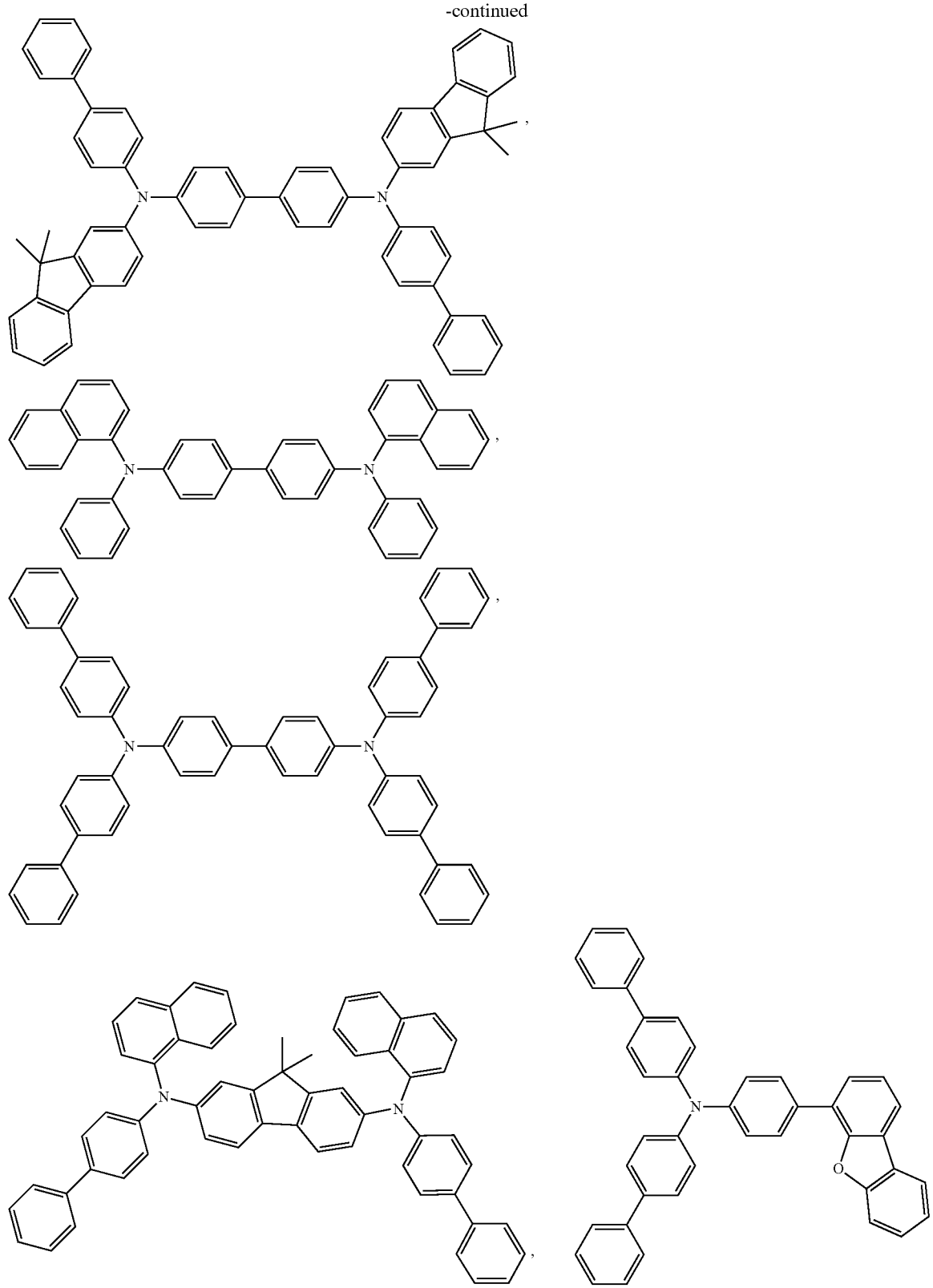

FIG. 1 schematically shows the organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

Figure 2:
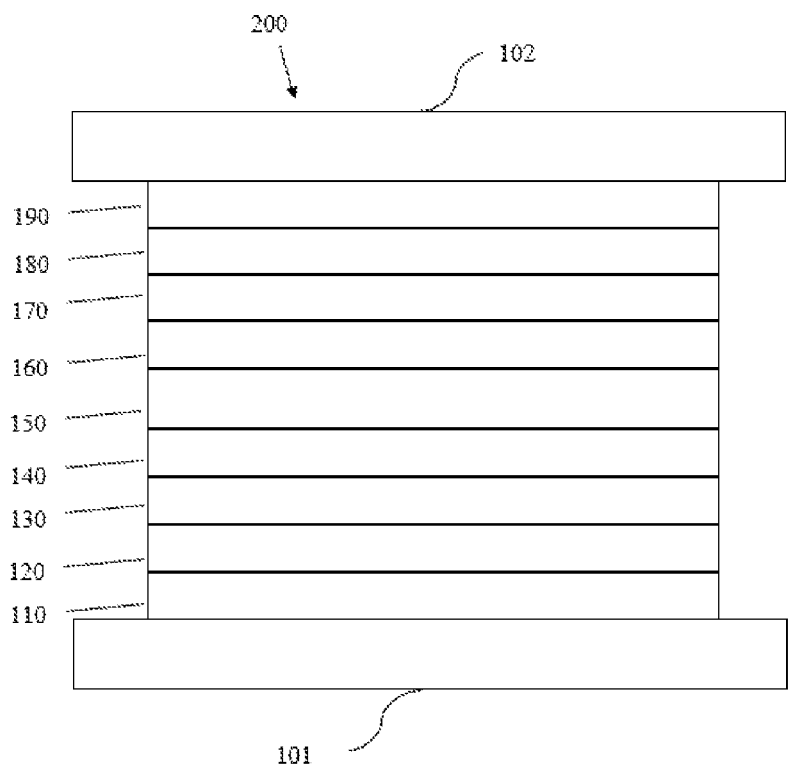
FIG. 2 shows a structural schematic diagram of the organic light-emitting device 200.

An OLED can be encapsulated by a barrier layer. FIG. 2 schematically shows the organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum; the hole transporting layer may have a first hole transporting layer and a second hole transporting layer.

In one embodiment, an OLED may be described as having an "organic layer" disposed between a cathode and an anode. This organic layer may comprise a single layer or multiple layers.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

The present disclosure will be further described below in combination with Examples, but the embodiments of the present disclosure are not limited thereto. The drugs and reagents used in the Examples can be obtained commercially, or they can be prepared by methods that have been disclosed.

A method for preparing an electroluminescent device comprising the follow steps:

Firstly, a glass substrate with a 120 nm-thick indium tin oxide (ITO) anode was cleaned, and then treated with oxygen plasma and UV ozone. After processing, the substrate was oven-dried in a glovebox to remove moisture. The substrate was then mounted on a substrate holder and loaded into a vacuum chamber. The organic layers specified below were deposited by thermal vacuum evaporation sequentially on the ITO anode at a rate of 0.2-2 angstroms per second under a vacuum degree of about $10^{-8}$ Torr.

Device Example 1

Compound BO-24 of the present disclosure was deposited as a hole injection layer (HIL), Compound HT was deposited as a first hole transporting layer (HTL1), and Compound HT was deposited as a second hole transporting layer (HTL2).

Device Comparative Example 1

Compound HI was deposited as a hole injection layer (HIL), Compound HT was deposited as a first hole transporting layer (HTL1), and Compound HT was deposited as a second hole transporting layer (HTL2).

Device Example 2

Compound HT doped with Compound BO-24 (3%) of the present disclosure was deposited as a hole injection layer (HIL) and a first hole transporting layer (HTL1), and Compound HT was deposited as a second hole transporting layer (HTL2).

Device Comparative Example 2

Compound HT was deposited as a hole injection layer (HIL) and a first hole transporting layer (HTL1), and Compound HT was deposited as a second hole transporting layer (HTL2).

On the second hole transporting layer (HTL2), all Examples and Comparative Examples included compound GD doped with compound H1 and compound H2 (10:45:45, 400 angstroms) as a emitting layer (EML), compound H2 (100 angstroms) as a hole blocking layer (HBL), and compound ET and 8-hydroxyquinolinolato-lithium (Liq) (40:60, 350 angstroms) as an electron transporting layer (ETL). Finally, 10 angstroms of 8-hydroxyquinolinolato-lithium (Liq) was deposited as an electron injection layer, and 1200 angstroms of aluminum was deposited as a cathode. The device was then transferred back to the glovebox and encapsulated with a glass lid and a moisture getter to complete the device.

For a layer with more than one materials being used, it was obtained by doping different compounds at the recorded weight ratio.

Some detailed device layer structures and thicknesses are shown in Table 1.

TABLE 1

| Part of the device structure of the device example | | | |
|---|---|---|---|
| No. | HIL | HTL1 | HTL2 |
| Example 1 | Compound BO-24 (100 Å) | Compound HT (200 Å) | Compound HT (200 Å) |
| Comparative Example 1 | Compound HI (100 Å) | Compound HT (200 Å) | Compound HT (200 Å) |
| Example 2 | Compound HT: Compound BO-24 (3 wt %) (300 Å) | | Compound HT (200 Å) |
| Comparative Example 2 | Compound HT (300 Å) | | Compound HT (200 Å) |

The structures of the materials used in the device are as follows:

Compound HI

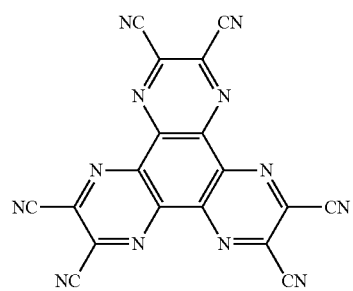

Compound HT

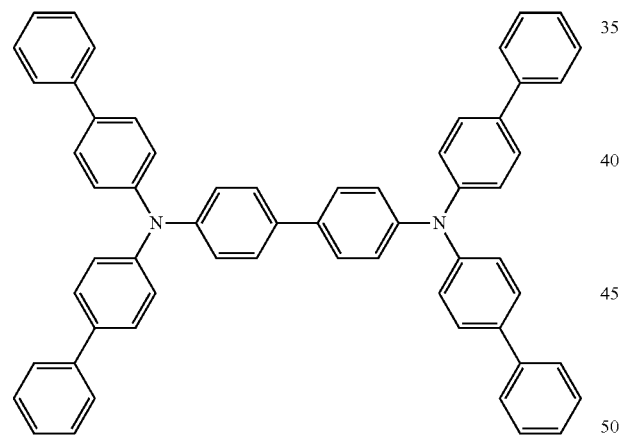

Compound H1

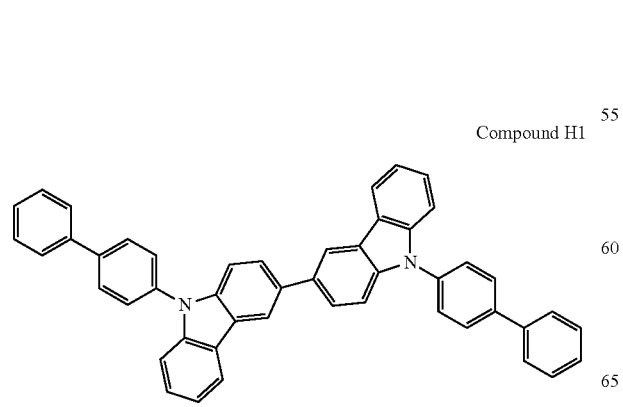

-continued

Compound H2

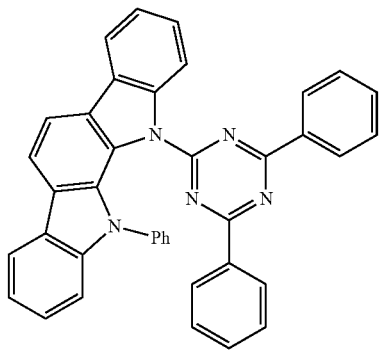

Compound GD

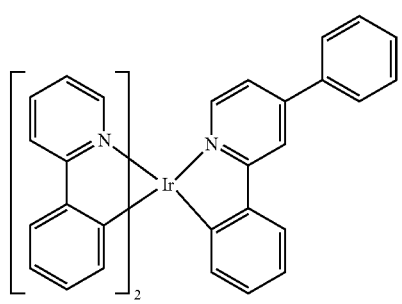

Compound ET

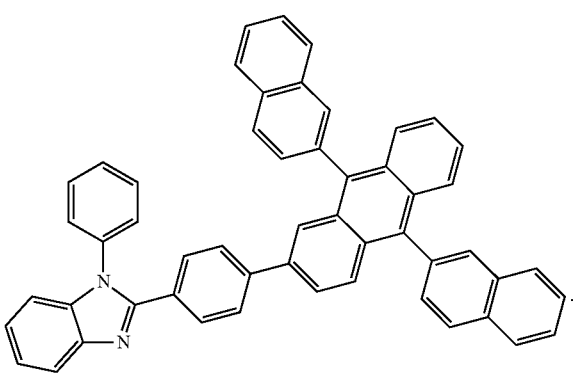

The LUMO energy levels of compounds AO-22, BO-24, BO-25 and compound HI are shown in Table 2:

TABLE 2

Data on LUMO energy level

| Compound No. | LUMO (eV) |
|---|---|
| Compound AO-22 | −4.70 |
| Compound BO-24 | −4.72 |
| Compound BO-25 | −4.73 |
| Compound HI | −4.20 |
| Comparative Compound 1 | −4.42 |

From the data in Table 2, it is shown that by introducing an electron-withdrawing substituent trifluoromethoxy on the $D_2$ and $E_2$ rings, the LUMO energy level of the compound of the present disclosure is reduced by 0.28 eV or more than that of Comparative Compound 1, which indicates that the substitution of an electron-withdrawing group on the $D_2$ and/or $E_2$ ring has an important role. At the same time, the LUMO energy level of the compound of the present disclosure is much lower than that of the compound HI such that a sufficiently small injection energy barrier between the HIL layer and the ITO anode can be achieved. Moreover, when the compound of the present disclosure is doped with a hole transporting material and used as a hole injection or transporting layer, there is also a greater chance to achieve a P-type conductivity effect.

Device Performance Test:

At a brightness of 1000 nits, the device of Example 1 was measured to have an external quantum efficiency (EQE) of 22.35%, a current efficiency (CE) of 76.20 cd/A, a color coordinate (CIE) of 0.439, 0.550, and a lifetime (LT97), measured from an initial brightness of 21750 nits at a constant current, of 310 hours. As measured under the same conditions, the device of Comparative Example 1 had an external quantum efficiency (EQE) of 21.95%, a current efficiency (CE) of 75.11 cd/A, a color coordinate (CIE) of 0.437, 0.552, and, under the same conditions, a lifetime of 234 hours. The device of Example 1 was slightly more efficient than that of Comparative Example 1, but more importantly, the lifetime of the device of Example 1 was significantly improved.

In addition, at a brightness of 1000 nits, the device of Example 2 was measured to have an external quantum efficiency (EQE) of 24.79%, a current efficiency (CE) of 84.32 cd/A, and a color coordinate (CIE) of 0.441, 0.548. As measured under the same conditions, the device of Comparative Example 2 had an external quantum efficiency (EQE) of 19.03%, a current efficiency (CE) of 65.12 cd/A, and a color coordinate (CIE) of 0.434, 0.554. It can be seen that the efficiency of the device of Example 2 was significantly improved compared to that of Comparative Example 2.

Either using the compound of the present disclosure as a hole injection layer material or doping it with a hole transporting material and using the resultant mixture as a hole injection or transporting layer can improve the balance of electron holes and electron transporting of the device, thereby bringing excellent device effects. This proves that compared to the prior art, use of the organic light-emitting device developed by the present disclosure results in a higher luminous efficiency, a longer service life, and a higher application value in the industry.

Although the detailed methods of the present disclosure have been described by the above Examples, the present disclosure is not limited thereto, that is to say, it is not meant that the present disclosure has to be implemented depending on the above detailed methods. It will be apparent to those skilled in the art that any improvements made to the present disclosure, equivalent replacements and addition of adjuvant ingredients to the raw materials of the products of the present disclosure, and selections of the specific implementations, etc., all fall within the protection scope and the disclosed scope of the present disclosure.

What is claimed is:

1. An organic compound having the structure of Formula (I):

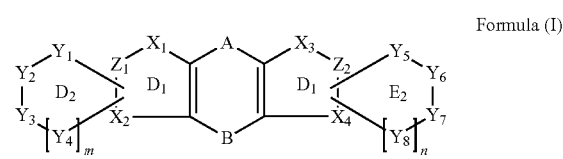

Formula (I)

in Formula (I), A and B are each independently selected from

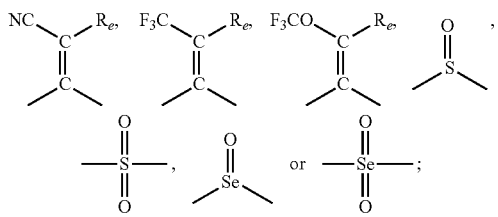

in Formula (I), $D_1$ and $E_1$ are each independently selected from any one of a five-membered unsaturated carbocyclic ring and a five-membered unsaturated heterocyclic ring;

in Formula (I), $D_2$ and $E_2$ are each independently selected from any one of a five-membered aromatic carbocyclic ring, a five-membered aromatic heterocyclic ring, a six-membered aromatic carbocyclic ring, and a six-membered aromatic heterocyclic ring, and the $D_2$ and $D_1$ are fused and share two atoms, and the $E_2$ and $E_1$ are fused and share 2 atoms;

in Formula (I), m and n are independently 0 or 1; when m is 0, $D_2$ is a five-membered ring; when m is 1, $D_2$ is a six-membered ring; when n is 0, $E_2$ is a five-membered ring; and when n is 1, $E_2$ is a six-membered ring;

$Z_1$ and $Z_2$ are C;

in Formula (I), $X_1$, $X_2$, $X_3$, and $X_4$ are each independently selected from any one of C, $C(R_1)(R_2)$, $N(R_1)$, O, $Si(R_1)(R_2)$, S, S=O, $S(=O)_2$, Se, Se=O, and $Se(=O)_2$;

in Formula (I), $Y_1$, $Y_2$, $Y_3$, $Y_4$, $Y_5$, $Y_6$, $Y_7$, and $Y_8$ are each independently selected from any one of $CR_b$, $CR_a$, N, and $NR_b$, and at least one of $Y_1$, $Y_2$, $Y_3$, $Y_4$, $Y_5$, $Y_6$, $Y_7$, and $Y_8$ is selected from $CR_a$;

the $R_a$ is an electron-withdrawing group;

the $R_e$, $R_1$, $R_2$ and $R_b$ are each independently selected from any one or a combination of at least two of hydrogen, deuterium, halogen, a substituted or unsubstituted alkyl group having 1-20 carbon atoms, a substituted or unsubstituted cycloalkyl group having 3-20 cyclic carbon atoms, a substituted or unsubstituted heteroalkyl group having 1-20 carbon atoms, a substituted or unsubstituted aralkyl having 7-30 carbon atoms, a substituted or unsubstituted alkoxyl group having 1-20 carbon atoms, a substituted or unsubstituted aryloxy group having 6-30 carbon atoms, a substituted or unsubstituted alkenyl group having 2-20 carbon atoms, a substituted or unsubstituted aryl group having 6-30 carbon atoms, a substituted or unsubstituted heteroaryl group having 3-30 carbon atoms, a substituted or unsubstituted alkylsilyl group having 3-20 carbon atoms, a substituted or unsubstituted arylsilyl group having 6-20 carbon atoms, a substituted or unsubstituted amine group having 0-20 carbon atoms, a substituted or unsubstituted acyl group having 1-20 carbon atoms, a substituted or unsubstituted carbonyl group having 1-20 carbon atoms, a substituted or unsubstituted carboxylic group having 1-20 carbon atoms, a substituted or unsubstituted ester group having 1-20 carbon atoms, a substituted or unsubstituted nitrile group having 1-20 carbon atoms, a substituted or unsubstituted isonitrile group having 1-20 carbon atoms, a substituted or unsubstituted sulfanyl group having 0-20 carbon atoms, a substituted or unsubstituted sulfinyl group having 0-20 carbon atoms, a substituted or unsubstituted sulfonyl having 0-20 carbon atoms, and a substituted or unsubstituted phosphino group having 0-20 carbon atoms; and any two adjacent substituents can optionally be joined to form a ring.

2. The organic compound according to claim 1, wherein the compound has a structure shown in any one of Formula (II) and Formula (III):

Formula (II)

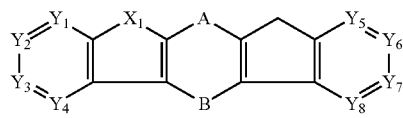

Formula (III)

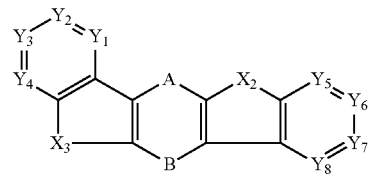

in Formula (II), $X_1$ and $X_2$, are each independently selected from any one of $C(R_1)(R_2)$, $N(R_1)$, O, $Si(R_1)(R_2)$, S, S=O, $S(=O)_2$, Se, Se=O, and $Se(=O)_2$;

in Formula (III), $X_2$ and $X_3$ are each independently selected from any one of $C(R_1)(R_2)$, $N(R_1)$, O, $Si(R_1)(R_2)$, S, S=O, $S(=O)_2$, Se, Se=O, and $Se(=O)_2$; and A, B, $Y_1$, $Y_2$, $Y_3$, $Y_4$, $Y_5$, $Y_6$, $Y_7$, $Y_8$, $R_1$, and $R_2$ have the same scope as in claim 1.

3. The organic compound according to claim 2, wherein in Formula (II), $X_1$ and $X_2$ are each independently selected from any one of O, S, S=O, $S(=O)_2$, Se, Se=O, and $Se(=O)_2$;

in Formula (III), $X_2$ and $X_3$ are each independently selected from any one of O, S, S=O, $S(=O)_2$, Se, Se=O, and $Se(=O)_2$.

4. The organic compound according to claim 2, wherein in Formula (II) and Formula (III), A and B are each independently selected from

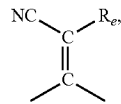

and $R_e$ is a cyano group.

5. The organic compound according to claim 2, wherein in Formula (II), $X_1$ and $X_2$ are each independently selected from any one of O, S, S=O, $S(=O)_2$, Se, Se=O, and $Se(=O)_2$;

in Formula (III), $X_2$ and $X_3$ are each independently selected from any one of O, S, S=O, $S(=O)_2$, Se, Se=O, and $Se(=O)_2$; and A and B are each independently selected from

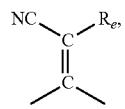

and $R_e$ is a cyano group.

6. The organic compound according to claim 2, wherein the $R_a$ has a Hammett substituent constant value of ≥0.3.

7. The organic compound according to claim 2, wherein $R_a$ is selected from any one or a combination of at least two of fluorine atom, chlorine atom, bromine atom, iodine atom, nitroso, nitro, sulfate group, sulfonate group, nitrate group, trifluoromethyl group, pentafluoroethyl group, trichloromethyl group, trifluoromethoxy group, pentafluoroethoxy group, trifluoromethylthio group, pentafluoroethylthio group, sulphone group, sulfoxide group, carboxyl group, carboxylate group, aldehyde group, carbonyl group, cyano group, isocyano group, oxycyano group, thiocyano group, selenocyano group, amido group, sulfonamido group, azo group, diazo group, azide group, fluorophenyl group, pyridyl group, pyrimidinyl group, triazinyl group, and dimethyl triazinyl group.

8. The organic compound according to claim 1, wherein in Formula (I), A and B are each independently selected from

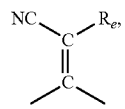

and $R_e$ is a cyano group.

9. The organic compound according to claim 1, wherein the $R_a$ has a Hammett substituent constant value of ≥0.3.

10. The organic compound according to claim 1, wherein $R_a$ is selected from any one or a combination of at least two of fluorine atom, chlorine atom, bromine atom, iodine atom, nitroso, nitro, sulfate group, sulfonate group, nitrate group, trifluoromethyl group, pentafluoroethyl group, trichloromethyl group, trifluoromethoxy group, pentafluoroethoxy group, trifluoromethylthio group, pentafluoroethylthio group, sulphone group, sulfoxide group, carboxyl group, carboxylate group, aldehyde group, carbonyl group, cyano group, isocyano group, oxycyano group, thiocyano group, selenocyano group, amido group, sulfonamido group, azo group, diazo group, azide group, fluorophenyl group, pyridyl group, pyrimidinyl group, triazinyl group, and dimethyl triazinyl group.

11. The organic compound according to claim 1, wherein the organic compound is any one of the compounds having the following structures:

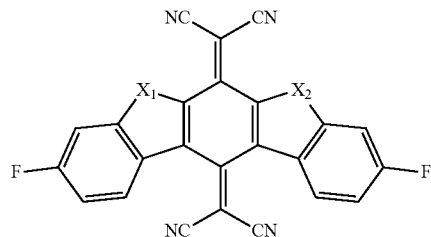

$X_1 = X_2 = O$ compound AO-1
$X_1 = X_2 = S$ compound AS-1
$X_1 = X_2 = Se$ compound ASe-1

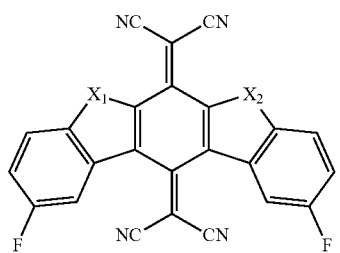

$X_1 = X_2 = O$ compound AO-2
$X_1 = X_2 = S$ compound AS-2
$X_1 = X_2 = Se$ compound ASe-2

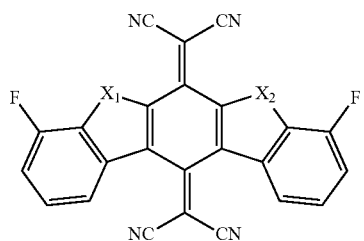

$X_1 = X_2 = O$ compound AO-3
$X_1 = X_2 = S$ compound AS-3
$X_1 = X_2 = Se$ compound ASe-3

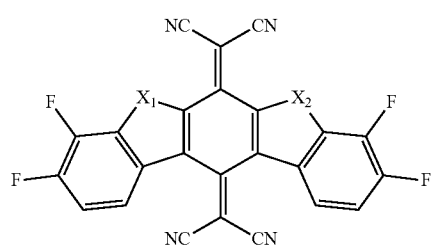

$X_1 = X_2 = O$ compound AO-4
$X_1 = X_2 = S$ compound AS-4
$X_1 = X_2 = Se$ compound ASe-4

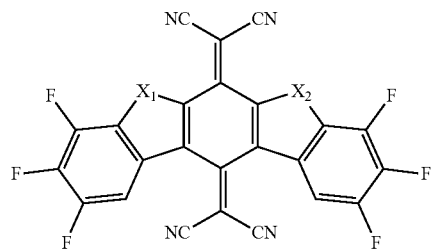

X₁ = X₂ = O compound AO-5
X₁ = X₂ = S compound AS-5
X₁ = X₂ = Se compound ASe-5
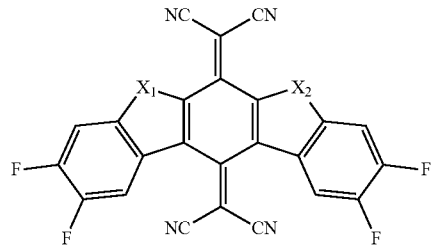
X₁ = X₂ = O compound AO-6
X₁ = X₂ = S compound AS-6
X₁ = X₂ = Se compound ASe-6
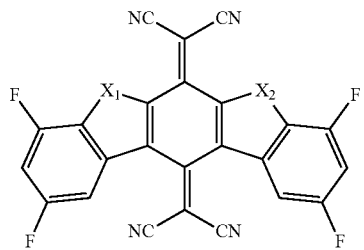
X₁ = X₂ = O compound AO-7
X₁ = X₂ = S compound AS-7
X₁ = X₂ = Se compound ASe-7
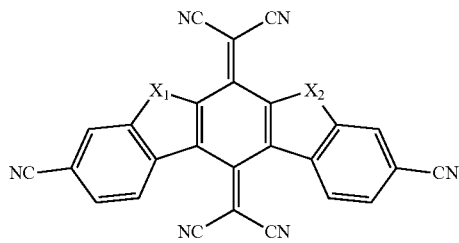
X₁ = X₂ = O compound AO-8
X₁ = X₂ = S compound AS-8
X₁ = X₂ = Se compound ASe-8
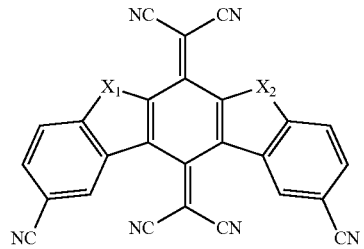
X₁ = X₂ = O compound AO-9
X₁ = X₂ = S compound AS-9
X₁ = X₂ = Se compound ASe-9

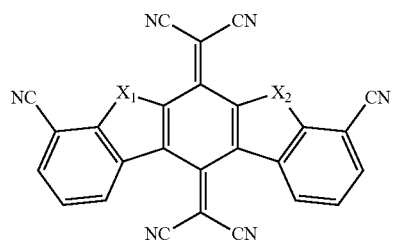
X$_1$ = X$_2$ = O compound AO-10
X$_1$ = X$_2$ = S compound AS-10
X$_1$ = X$_2$ = Se compound ASe-10
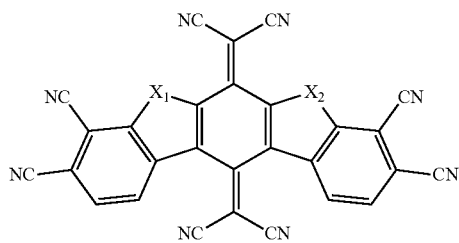
X$_1$ = X$_2$ = O compound AO-11
X$_1$ = X$_2$ = S compound AS-11
X$_1$ = X$_2$ = Se compound ASe-11
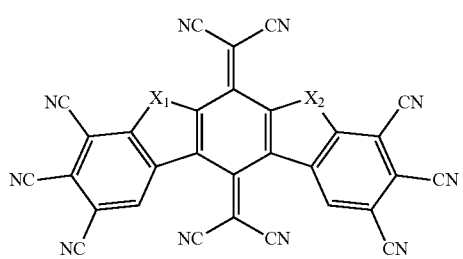
X$_1$ = X$_2$ = O compound AO-12
X$_1$ = X$_2$ = S compound AS-12
X$_1$ = X$_2$ = Se compound ASe-12
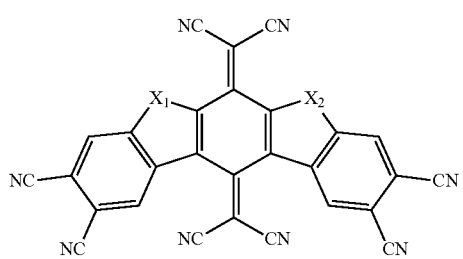

X₁ = X₂ = O compound AO-13
X₁ = X₂ = S compound AS-13
X₁ = X₂ = Se compound ASe-13
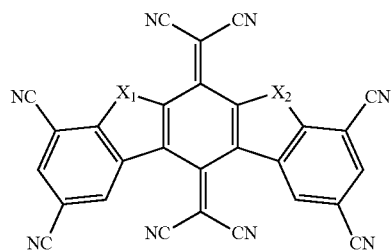
X₁ = X₂ = O compound AO-14
X₁ = X₂ = S compound AS-14
X₁ = X₂ = Se compound ASe-14
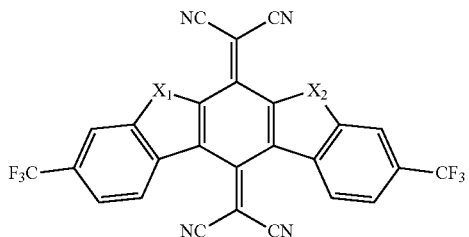
X₁ = X₂ = O compound AO-15
X₁ = X₂ = S compound AS-15
X₁ = X₂ = Se compound ASe-15
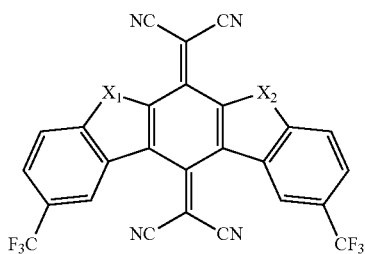
X₁ = X₂ = O compound AO-16
X₁ = X₂ = S compound AS-16
X₁ = X₂ = Se compound ASe-16
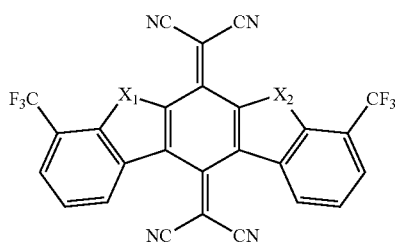
X₁ = X₂ = O compound AO-17
X₁ = X₂ = S compound AS-17
X₁ = X₂ = Se compound ASe-17

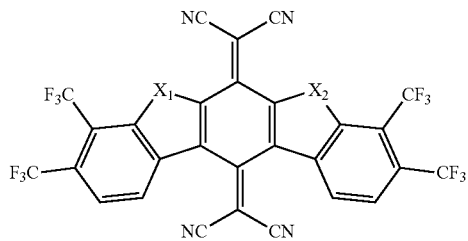
X₁ = X₂ = O compound AO-18
X₁ = X₂ = S compound AS-18
X₁ = X₂ = Se compound ASe-18
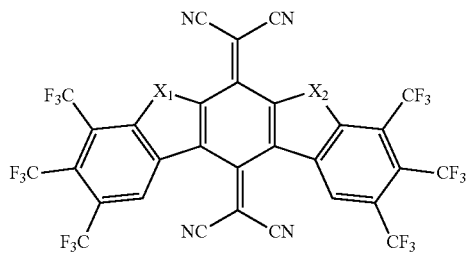
X₁ = X₂ = O compound AO-19
X₁ = X₂ = S compound AS-19
X₁ = X₂ = Se compound ASe-19
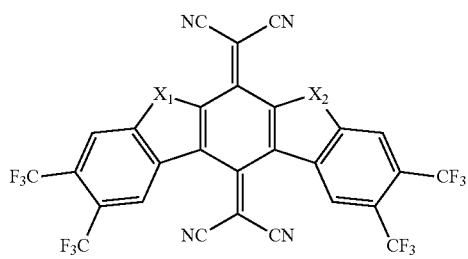
X₁ = X₂ = O compound AO-20
X₁ = X₂ = S compound AS-20
X₁ = X₂ = Se compound ASe-20
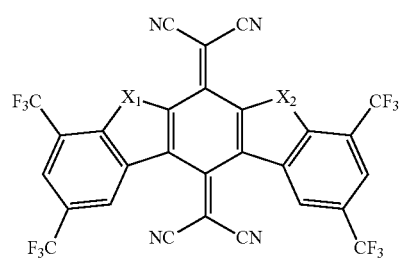
X₁ = X₂ = O compound AO-21
X₁ = X₂ = S compound AS-21
X₁ = X₂ = Se compound ASe-21
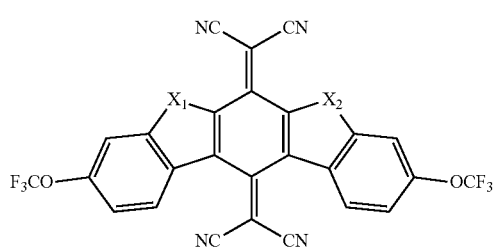

X₁ = X₂ = O compound AO-22
X₁ = X₂ = S compound AS-22
X₁ = X₂ = Se compound ASe-22
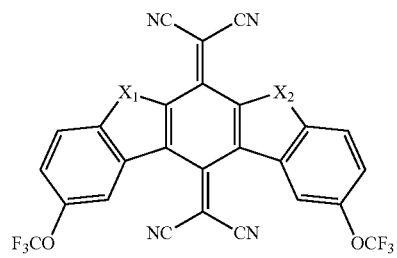
X₁ = X₂ = O compound AO-23
X₁ = X₂ = S compound AS-23
X₁ = X₂ = Se compound ASe-23
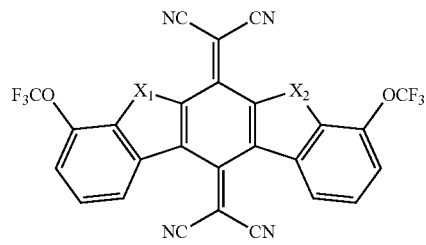
X₁ = X₂ = O compound AO-24
X₁ = X₂ = S compound AS-24
X₁ = X₂ = Se compound ASe-24
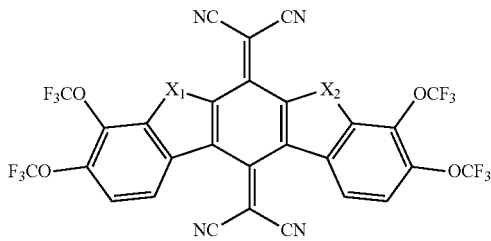
X₁ = X₂ = O compound AO-25
X₁ = X₂ = S compound AS-25
X₁ = X₂ = Se compound ASe-25
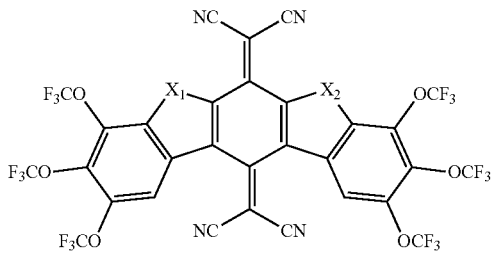
X₁ = X₂ = O compound AO-26
X₁ = X₂ = S compound AS-26
X₁ = X₂ = Se compound ASe-26

-continued
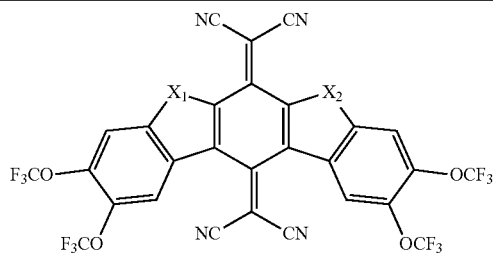
X₁ = X₂ = O compound AO-27
X₁ = X₂ = S compound AS-27
X₁ = X₂ = Se compound ASe-27
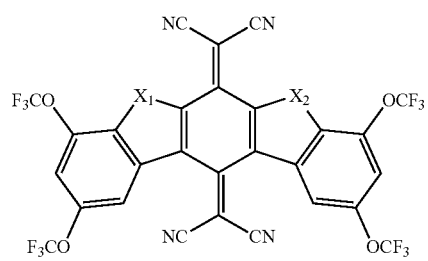
X₁ = X₂ = O compound AO-28
X₁ = X₂ = S compound AS-28
X₁ = X₂ = Se compound ASe-28
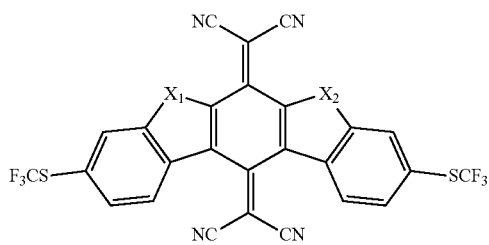
X₁ = X₂ = O compound AO-29
X₁ = X₂ = S compound AS-29
X₁ = X₂ = Se compound ASe-29
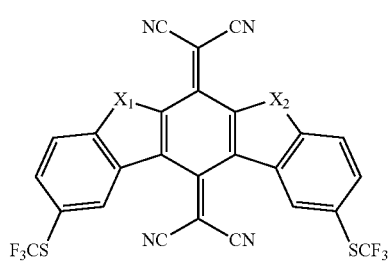
X₁ = X₂ = O compound AO-30
X₁ = X₂ = S compound AS-30
X₁ = X₂ = Se compound ASe-30
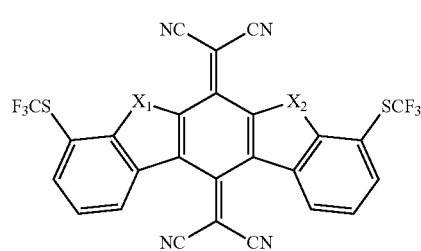

$X_1 = X_2 = $ O compound AO-31
$X_1 = X_2 = $ S compound AS-31
$X_1 = X_2 = $ Se compound ASe-31
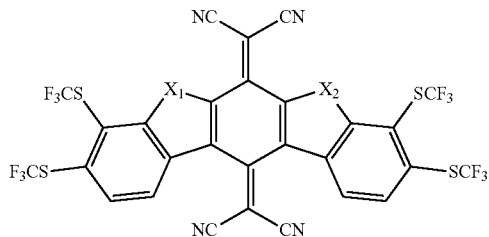
$X_1 = X_2 = $ O compound AO-32
$X_1 = X_2 = $ S compound AS-32
$X_1 = X_2 = $ Se compound ASe-32
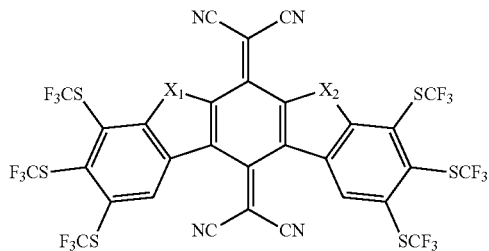
$X_1 = X_2 = $ O compound AO-33
$X_1 = X_2 = $ S compound AS-33
$X_1 = X_2 = $ Se compound ASe-33
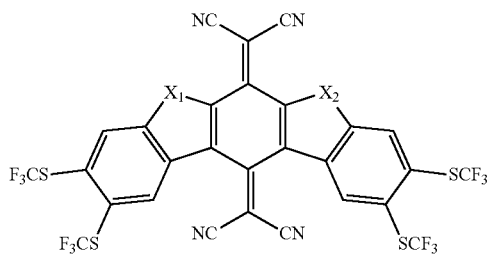
$X_1 = X_2 = $ O compound AO-34
$X_1 = X_2 = $ S compound AS-34
$X_1 = X_2 = $ Se compound ASe-34
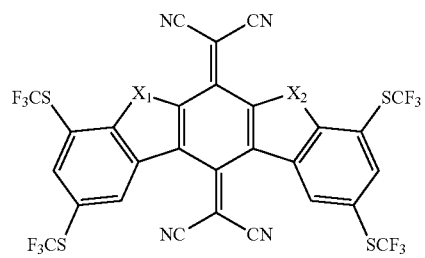
$X_1 = X_2 = $ O compound AO-35
$X_1 = X_2 = $ S compound AS-35
$X_1 = X_2 = $ Se compound ASe-35

-continued
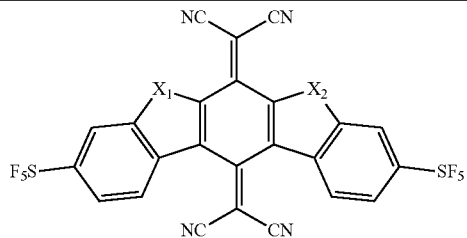
X₁ = X₂ = O compound AO-36
X₁ = X₂ = S compound AS-36
X₁ = X₂ = Se compound ASe-36
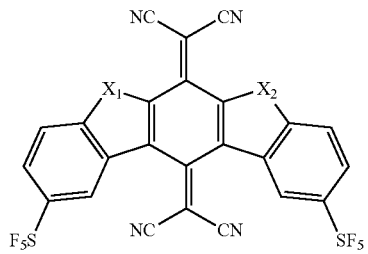
X₁ = X₂ = O compound AO-37
X₁ = X₂ = S compound AS-37
X₁ = X₂ = Se compound ASe-37
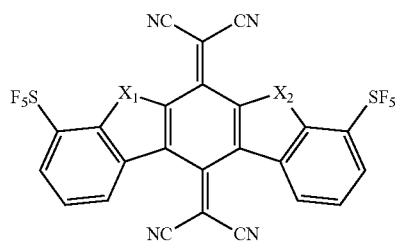
X₁ = X₂ = O compound AO-38
X₁ = X₂ = S compound AS-38
X₁ = X₂ = Se compound ASe-38
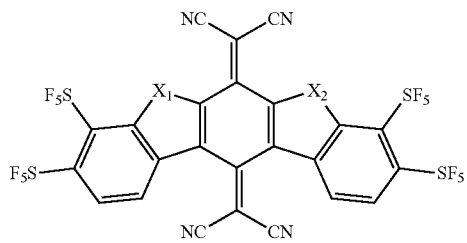
X₁ = X₂ = O compound AO-39
X₁ = X₂ = S compound AS-39
X₁ = X₂ = Se compound ASe-39
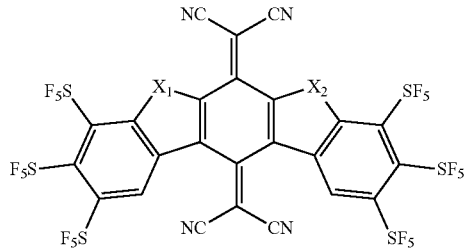
X₁ = X₂ = O compound AO-40
X₁ = X₂ = S compound AS-40
X₁ = X₂ = Se compound ASe-40

-continued
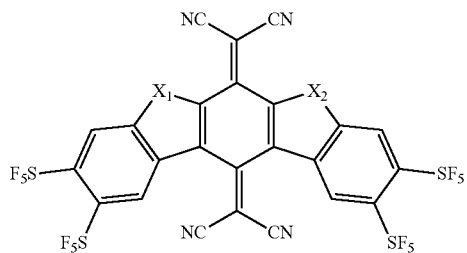
X₁ = X₂ = O compound AO-41
X₁ = X₂ = S compound AS-41
X₁ = X₂ = Se compound ASe-41
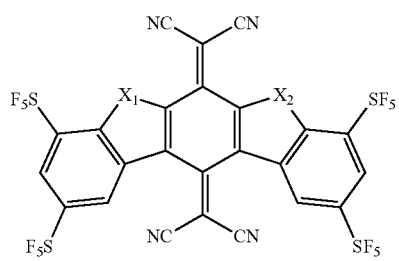
X₁ = X₂ = O compound AO-42
X₁ = X₂ = S compound AS-42
X₁ = X₂ = Se compound ASe-42
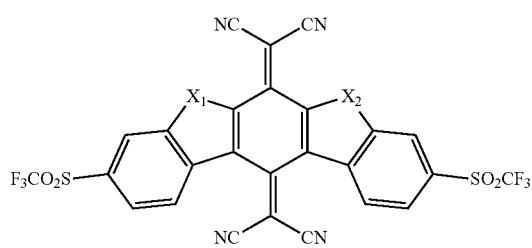
X₁ = X₂ = O compound AO-43
X₁ = X₂ = S compound AS-43
X₁ = X₂ = Se compound ASe-43
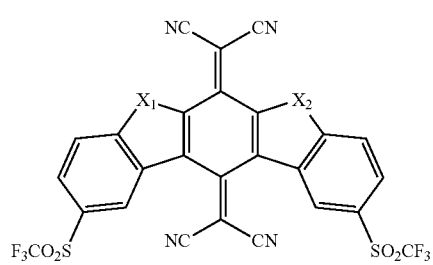
X₁ = X₂ = O compound AO-44
X₁ = X₂ = S compound AS-44
X₁ = X₂ = Se compound ASe-44
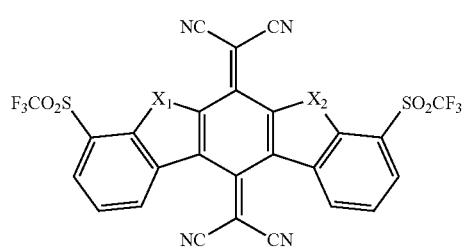

X₁ = X₂ = O compound AO-45
X₁ = X₂ = S compound AS-45
X₁ = X₂ = Se compound ASe-45
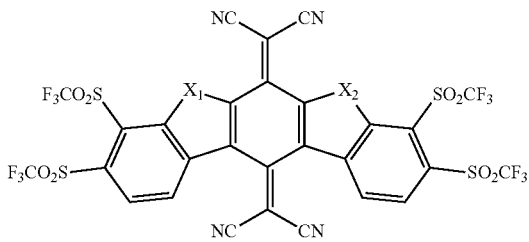
X₁ = X₂ = O compound AO-46
X₁ = X₂ = S compound AS-46
X₁ = X₂ = Se compound ASe-46
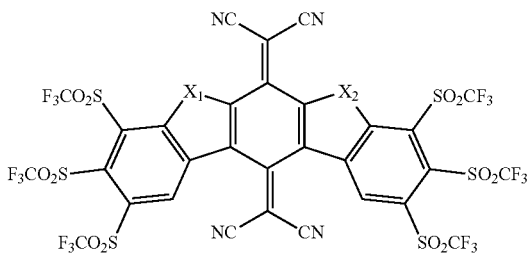
X₁ = X₂ = O compound AO-47
X₁ = X₂ = S compound AS-47
X₁ = X₂ = Se compound ASe-47
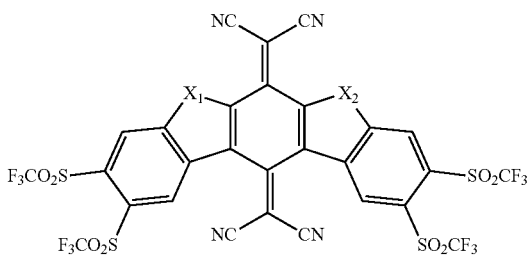
X₁ = X₂ = O compound AO-48
X₁ = X₂ = S compound AS-48
X₁ = X₂ = Se compound ASe-48
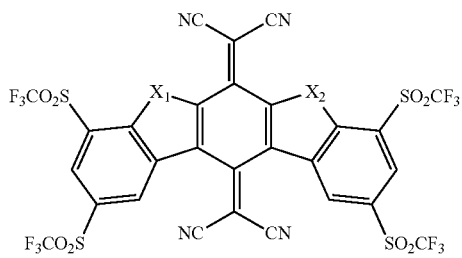
X₁ = X₂ = O compound AO-49
X₁ = X₂ = S compound AS-49
X₁ = X₂ = Se compound ASe-49

-continued
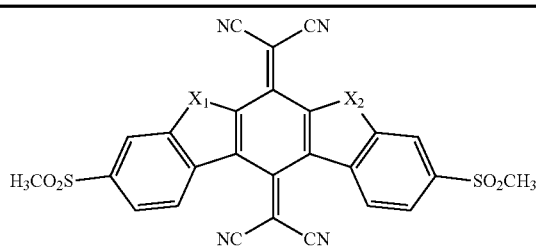
X₁ = X₂ = O compound AO-50
X₁ = X₂ = S compound AS-50
X₁ = X₂ = Se compound ASe-50
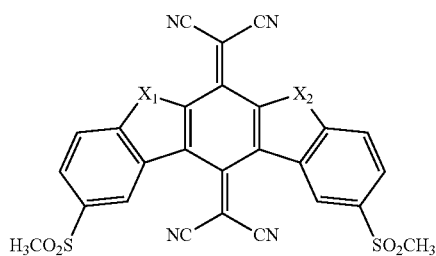
X₁ = X₂ = O compound AO-51
X₁ = X₂ = S compound AS-51
X₁ = X₂ = Se compound ASe-51
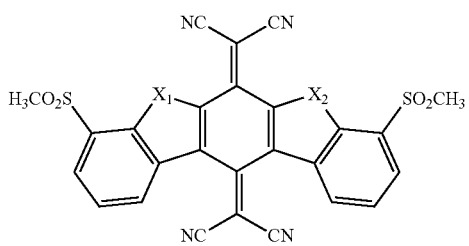
X₁ = X₂ = O compound AO-52
X₁ = X₂ = S compound AS-52
X₁ = X₂ = Se compound ASe-52
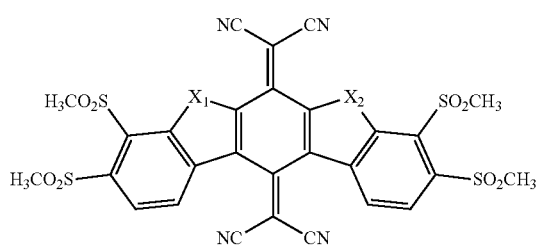
X₁ = X₂ = O compound AO-53
X₁ = X₂ = S compound AS-53
X₁ = X₂ = Se compound ASe-53
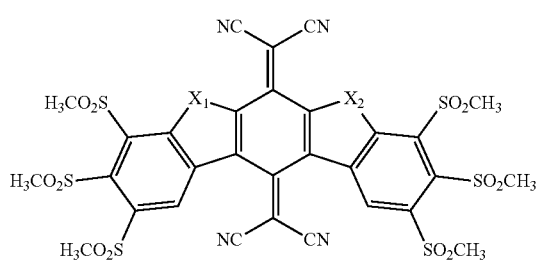

X₁ = X₂ = O compound AO-54
X₁ = X₂ = S compound AS-54
X₁ = X₂ = Se compound ASe-54
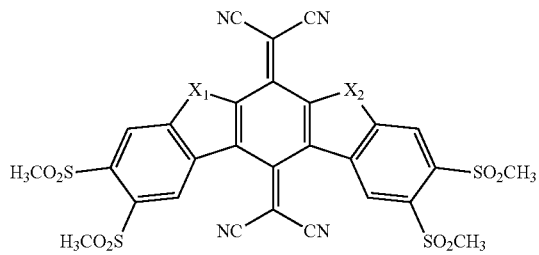
X₁ = X₂ = O compound AO-55
X₁ = X₂ = S compound AS-55
X₁ = X₂ = Se compound ASe-55
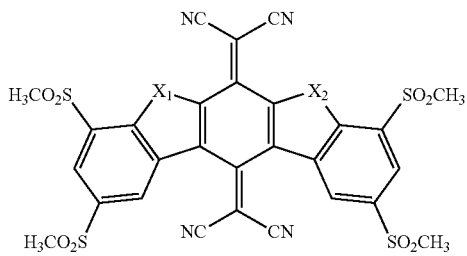
X₁ = X₂ = O compound AO-56
X₁ = X₂ = S compound AS-56
X₁ = X₂ = Se compound ASe-56
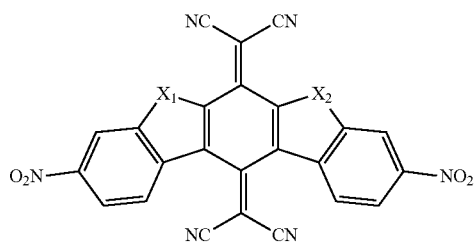
X₁ = X₂ = O compound AO-57
X₁ = X₂ = S compound AS-57
X₁ = X₂ = Se compound ASe-57
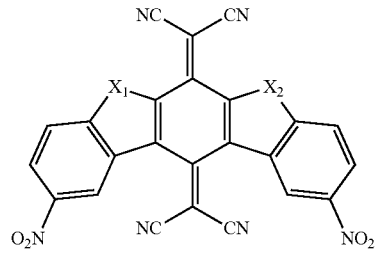
X₁ = X₂ = O compound AO-58
X₁ = X₂ = S compound AS-58
X₁ = X₂ = Se compound ASe-58

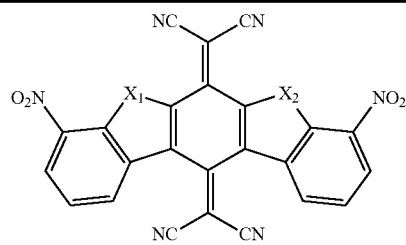
X₁ = X₂ = O compound AO-59
X₁ = X₂ = S compound AS-59
X₁ = X₂ = Se compound ASe-59
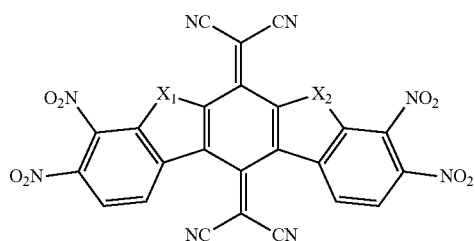
X₁ = X₂ = O compound AO-60
X₁ = X₂ = S compound AS-60
X₁ = X₂ = Se compound ASe-60
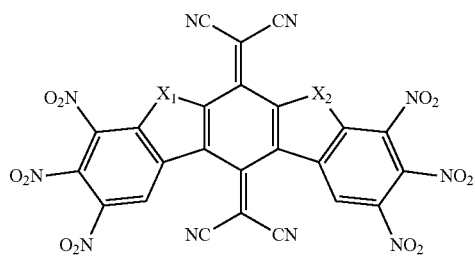
X₁ = X₂ = O compound AO-61
X₁ = X₂ = S compound AS-61
X₁ = X₂ = Se compound ASe-61
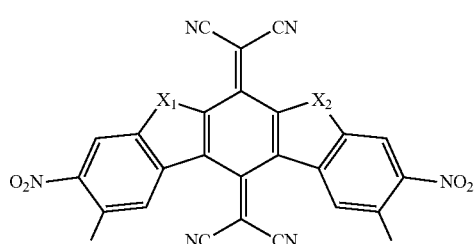
X₁ = X₂ = O compound AO-62
X₁ = X₂ = S compound AS-62
X₁ = X₂ = Se compound ASe-62
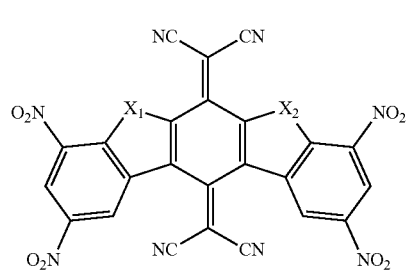

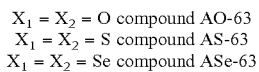
X₁ = X₂ = O compound AO-63
X₁ = X₂ = S compound AS-63
X₁ = X₂ = Se compound ASe-63
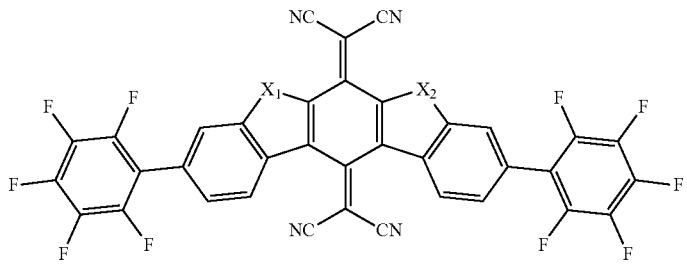
X₁ = X₂ = O compound AO-64
X₁ = X₂ = S compound AS-64
X₁ = X₂ = Se compound ASe-64
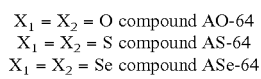
X₁ = X₂ = O compound AO-65
X₁ = X₂ = S compound AS-65
X₁ = X₂ = Se compound ASe-65
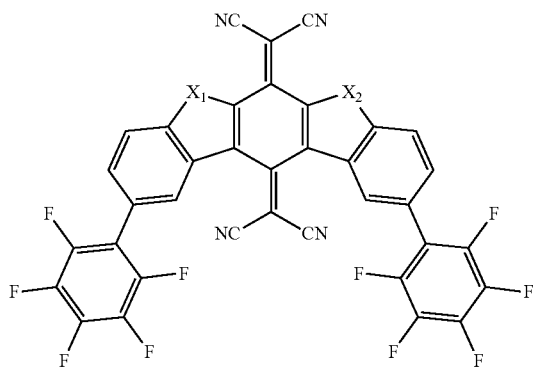
X₁ = X₂ = O compound AO-66
X₁ = X₂ = S compound AS-66
X₁ = X₂ = Se compound ASe-66
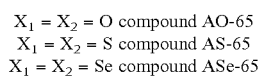
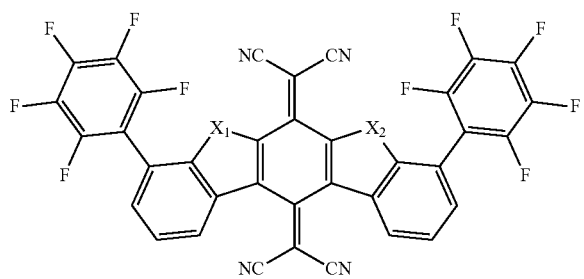
X₁ = X₂ = O compound AO-67
X₁ = X₂ = S compound AS-67
X₁ = X₂ = Se compound ASe-67
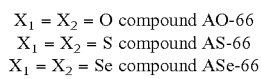
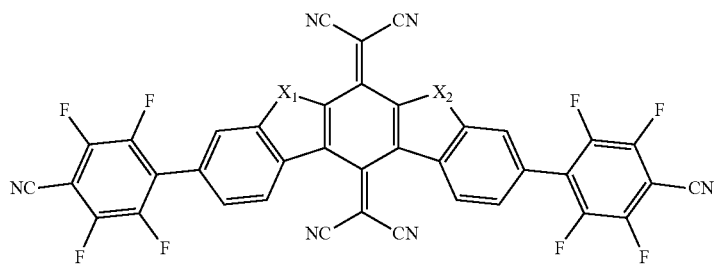
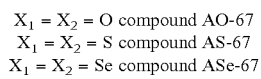

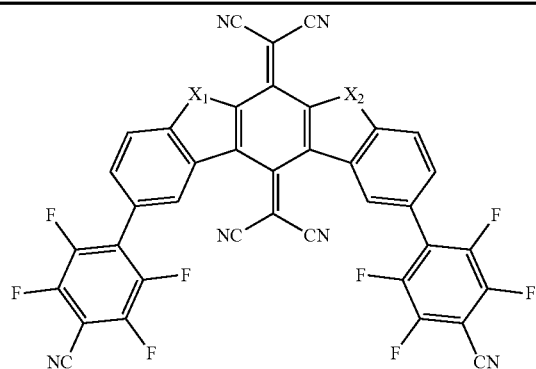
X₁ = X₂ = O compound AO-68
X₁ = X₂ = S compound AS-68
X₁ = X₂ = Se compound ASe-68
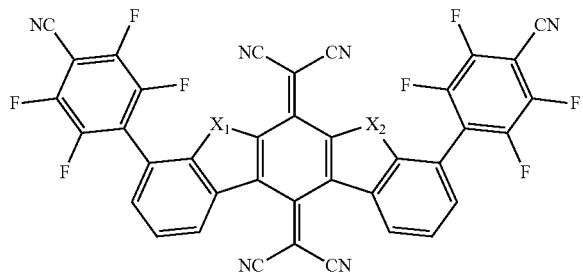
X₁ = X₂ = O compound AO-69
X₁ = X₂ = S compound AS-69
X₁ = X₂ = Se compound ASe-69
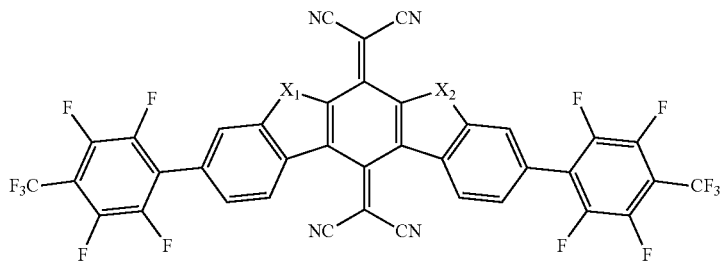
X₁ = X₂ = O compound AO-70
X₁ = X₂ = S compound AS-70
X₁ = X₂ = Se compound ASe-70
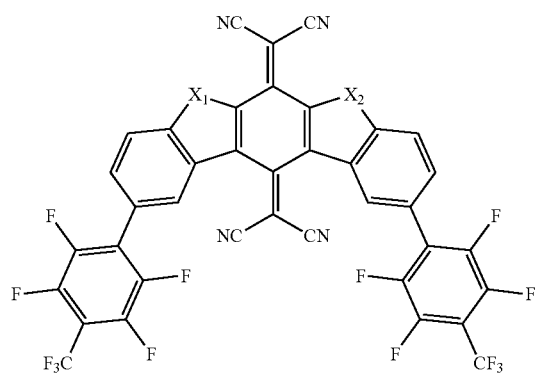
X₁ = X₂ = O compound AO-71
X₁ = X₂ = S compound AS-71
X₁ = X₂ = Se compound ASe-71

-continued
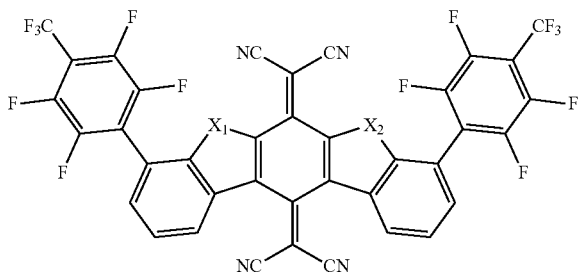
X₁ = X₂ = O compound AO-72
X₁ = X₂ = S compound AS-72
X₁ = X₂ = Se compound ASe-72
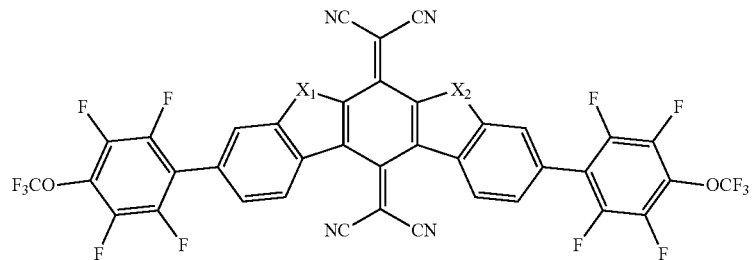
X₁ = X₂ = O compound AO-73
X₁ = X₂ = S compound AS-73
X₁ = X₂ = Se compound ASe-73
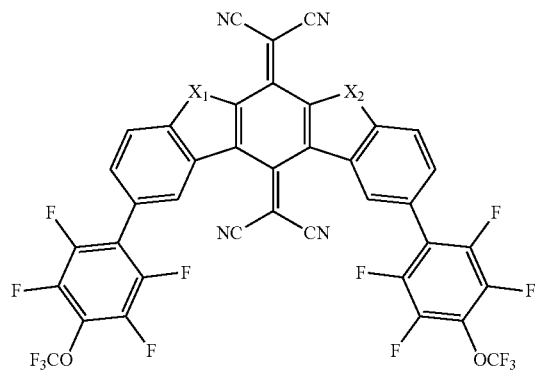
X₁ = X₂ = O compound AO-74
X₁ = X₂ = S compound AS-74
X₁ = X₂ = Se compound ASe-74
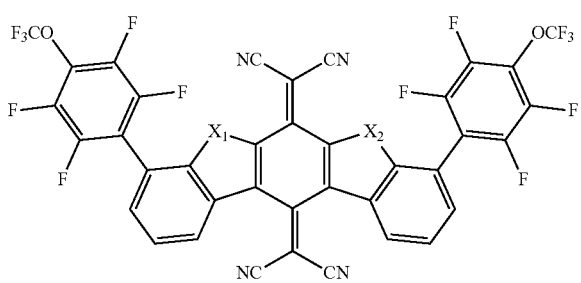
X₁ = X₂ = O compound AO-75
X₁ = X₂ = S compound AS-75
X₁ = X₂ = Se compound ASe-75

-continued
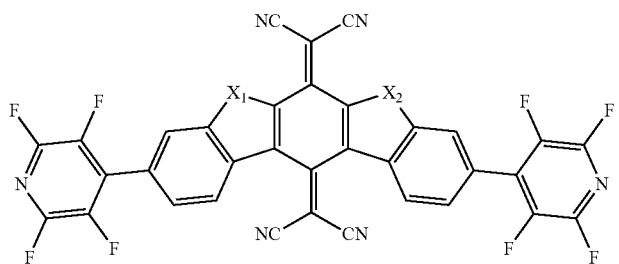
X₁ = X₂ = O compound AO-76
X₁ = X₂ = S compound AS-76
X₁ = X₂ = Se compound ASe-76
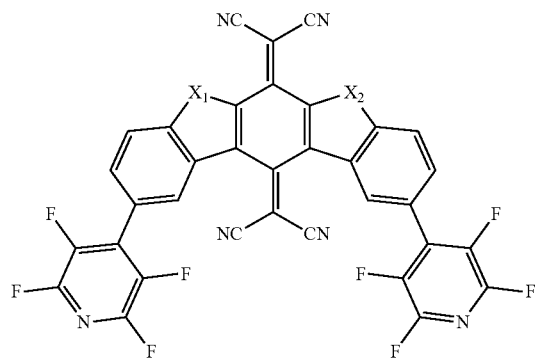
X₁ = X₂ = O compound AO-77
X₁ = X₂ = S compound AS-77
X₁ = X₂ = Se compound ASe-77
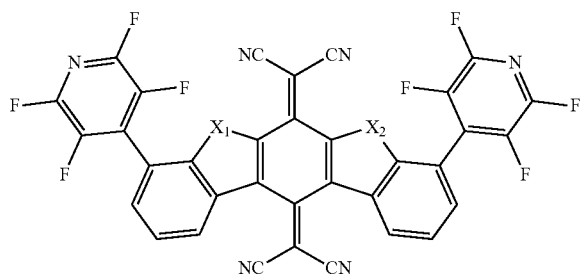
X₁ = X₂ = O compound AO-78
X₁ = X₂ = S compound AS-78
X₁ = X₂ = Se compound ASe-78
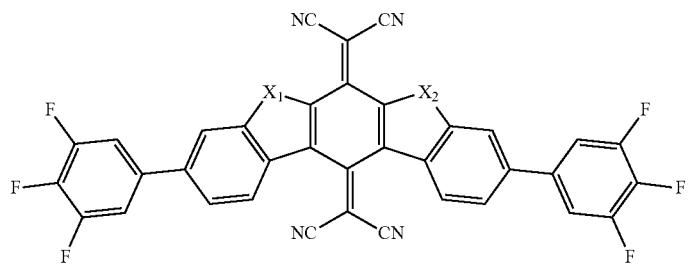
X₁ = X₂ = O compound AO-79
X₁ = X₂ = S compound AS-79
X₁ = X₂ = Se compound ASe-79

-continued
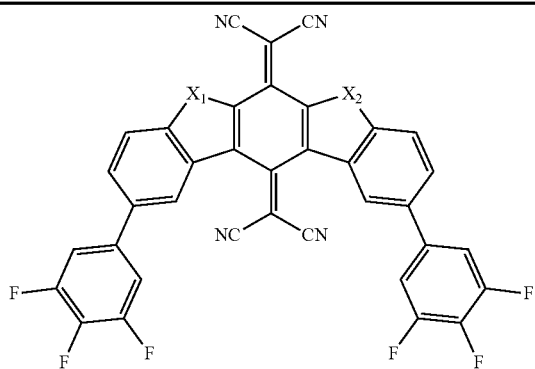
X₁ = X₂ = O compound AO-80
X₁ = X₂ = S compound AS-80
X₁ = X₂ = Se compound ASe-80
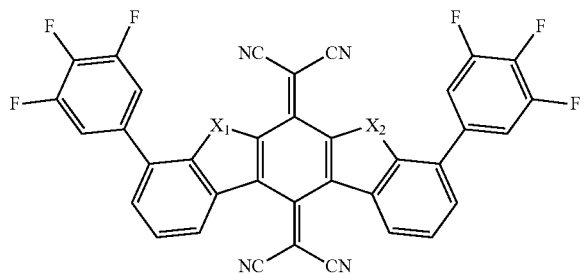
X₁ = X₂ = O compound AO-81
X₁ = X₂ = S compound AS-81
X₁ = X₂ = Se compound ASe-81
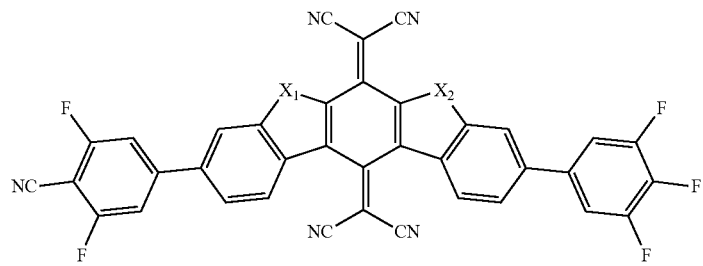
X₁ = X₂ = O compound AO-82
X₁ = X₂ = S compound AS-82
X₁ = X₂ = Se compound ASe-82
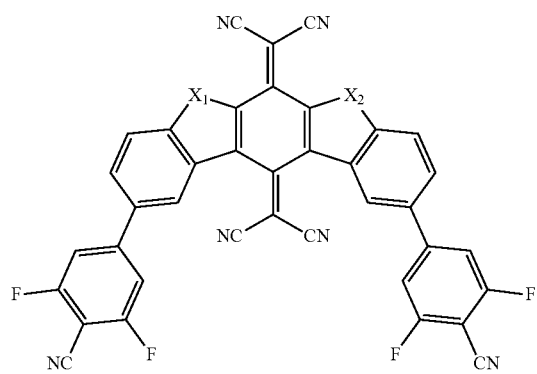
X₁ = X₂ = O compound AO-83
X₁ = X₂ = S compound AS-83
X₁ = X₂ = Se compound ASe-83

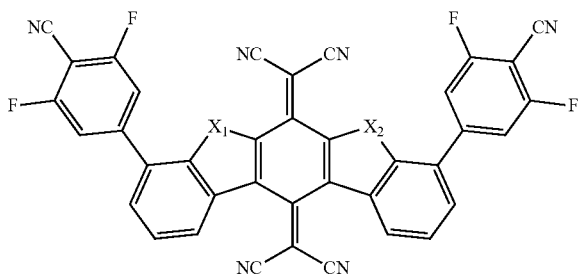
X₁ = X₂ = O compound AO-84
X₁ = X₂ = S compound AS-84
X₁ = X₂ = Se compound ASe-84
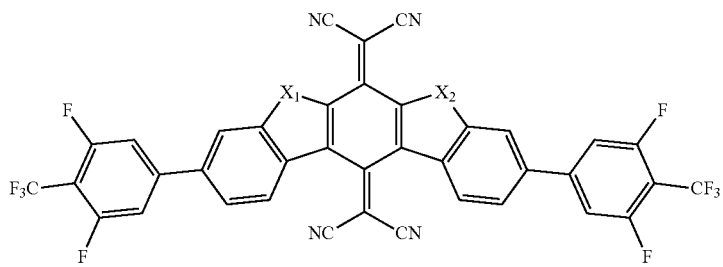
X₁ = X₂ = O compound AO-85
X₁ = X₂ = S compound AS-85
X₁ = X₂ = Se compound ASe-85
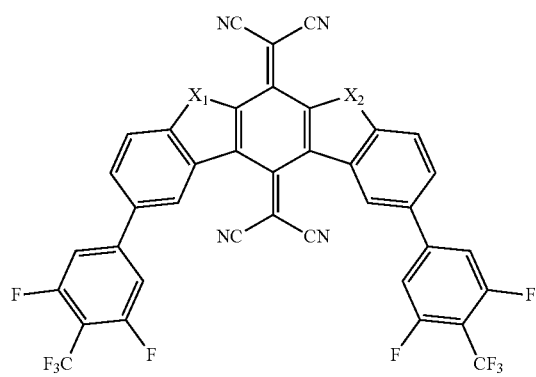
X₁ = X₂ = O compound AO-86
X₁ = X₂ = S compound AS-86
X₁ = X₂ = Se compound ASe-86
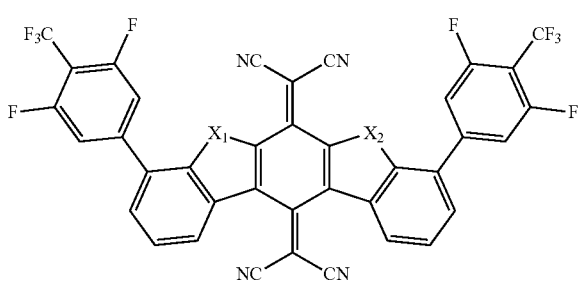
X₁ = X₂ = O compound AO-87
X₁ = X₂ = S compound AS-87
X₁ = X₂ = Se compound ASe-87

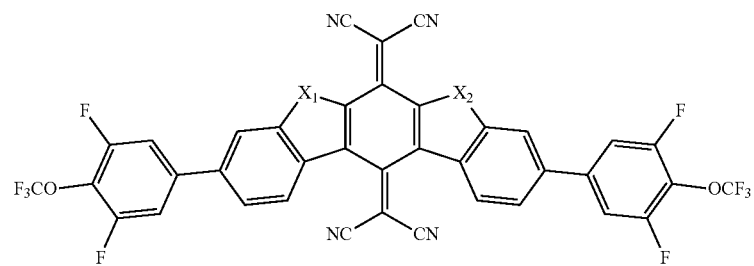
X₁ = X₂ = O compound AO-88
X₁ = X₂ = S compound AS-88
X₁ = X₂ = Se compound ASe-88
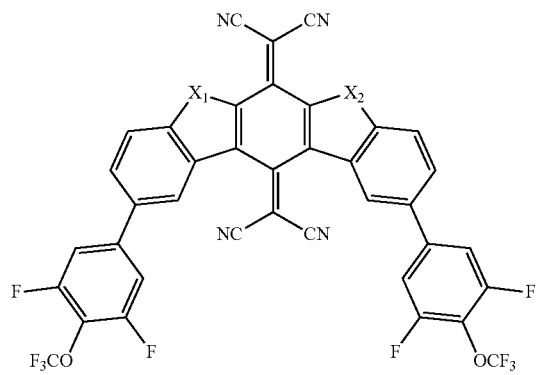
X₁ = X₂ = O compound AO-89
X₁ = X₂ = S compound AS-89
X₁ = X₂ = Se compound ASe-89
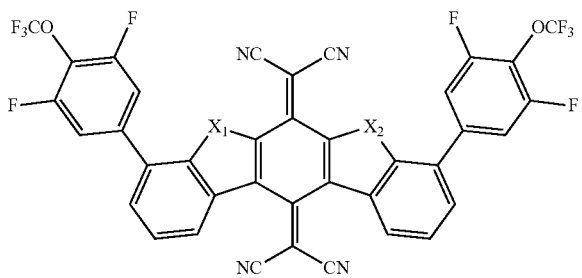
X₁ = X₂ = O compound AO-90
X₁ = X₂ = S compound AS-90
X₁ = X₂ = Se compound ASe-90
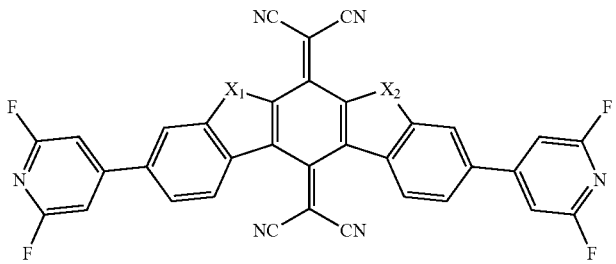
X₁ = X₂ = O compound AO-91
X₁ = X₂ = S compound AS-91
X₁ = X₂ = Se compound ASe-91

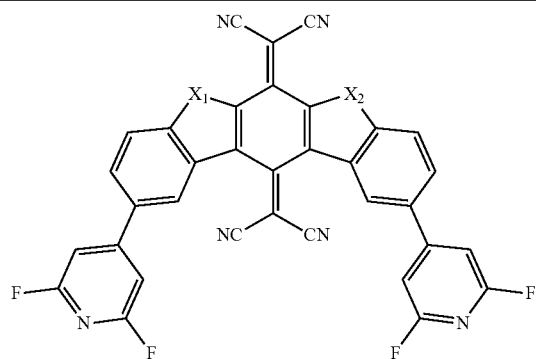
X₁ = X₂ = O compound AO-92
X₁ = X₂ = S compound AS-92
X₁ = X₂ = Se compound ASe-92
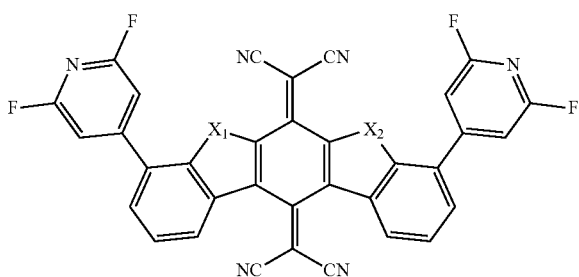
X₁ = X₂ = O compound AO-93
X₁ = X₂ = S compound AS-93
X₁ = X₂ = Se compound ASe-93
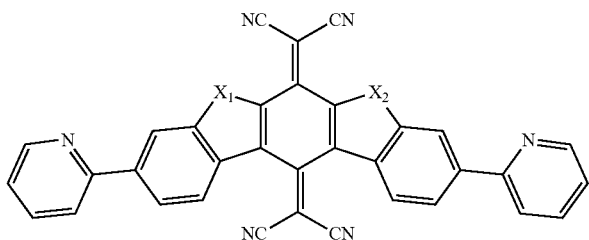
X₁ = X₂ = O compound AO-94
X₁ = X₂ = S compound AS-94
X₁ = X₂ = Se compound ASe-94
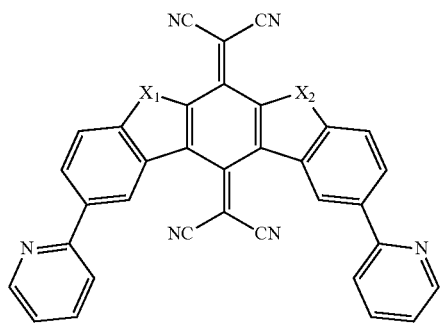
X₁ = X₂ = O compound AO-95
X₁ = X₂ = S compound AS-95
X₁ = X₂ = Se compound ASe-95

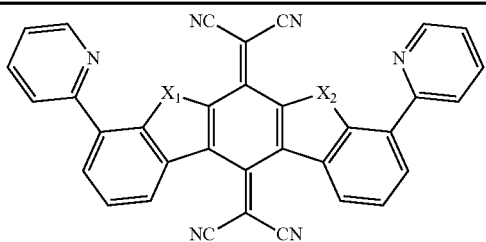
X₁ = X₂ = O compound AO-96
X₁ = X₂ = S compound AS-96
X₁ = X₂ = Se compound ASe-96
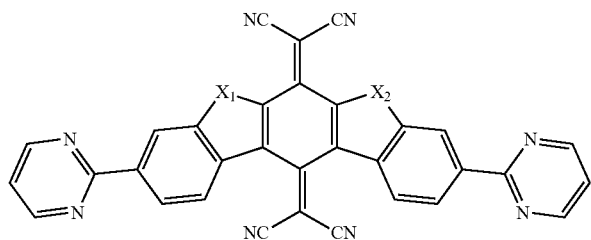
X₁ = X₂ = O compound AO-97
X₁ = X₂ = S compound AS-97
X₁ = X₂ = Se compound ASe-97
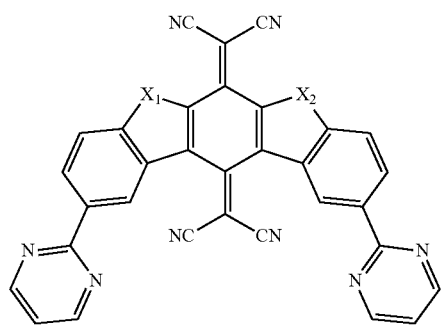
X₁ = X₂ = O compound AO-98
X₁ = X₂ = S compound AS-98
X₁ = X₂ = Se compound ASe-98
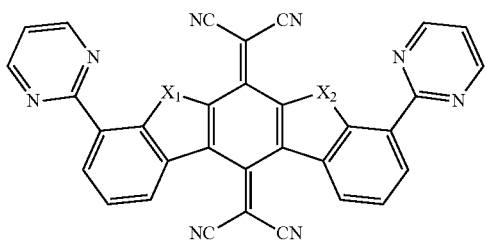
X₁ = X₂ = O compound AO-99
X₁ = X₂ = S compound AS-99
X₁ = X₂ = Se compound ASe-99
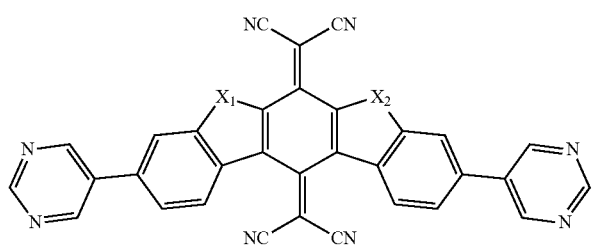

X₁ = X₂ = O compound AO-100
X₁ = X₂ = S compound AS-100
X₁ = X₂ = Se compound ASe-100
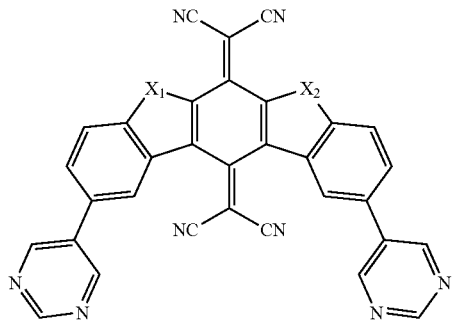
X₁ = X₂ = O compound AO-101
X₁ = X₂ = S compound AS-101
X₁ = X₂ = Se compound ASe-101
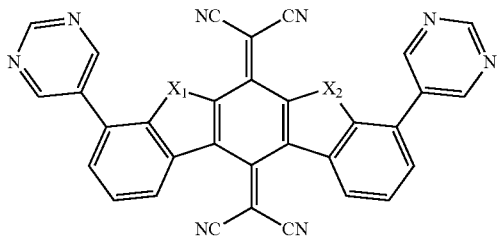
X₁ = X₂ = O compound AO-102
X₁ = X₂ = S compound AS-102
X₁ = X₂ = Se compound ASe-102
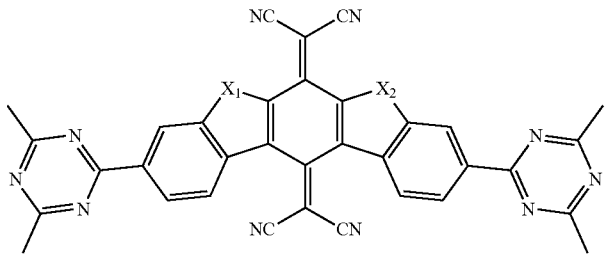
X₁ = X₂ = O compound AO-103
X₁ = X₂ = S compound AS-103
X₁ = X₂ = Se compound ASe-103
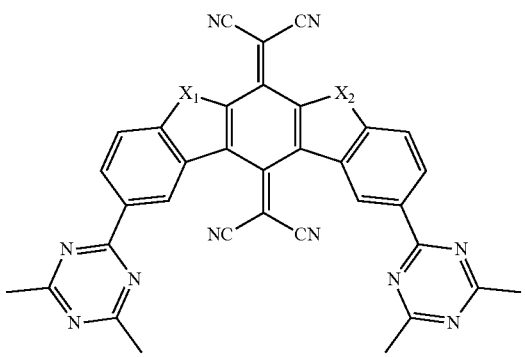
X₁ = X₂ = O compound AO-104
X₁ = X₂ = S compound AS-104
X₁ = X₂ = Se compound ASe-104

-continued
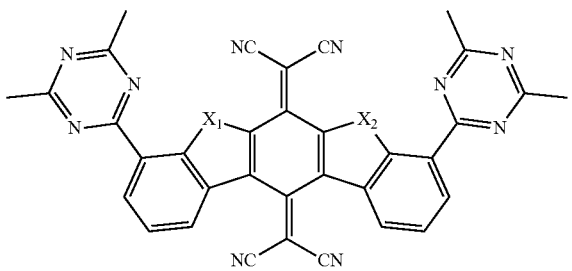
X₁ = X₂ = O compound AO-105
X₁ = X₂ = S compound AS-105
X₁ = X₂ = Se compound ASe-105
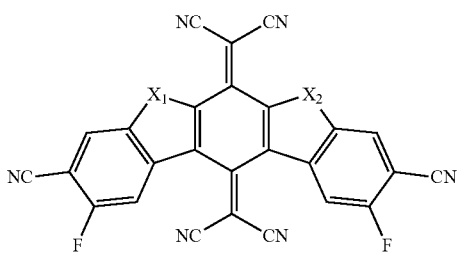
X₁ = X₂ = O compound AO-106
X₁ = X₂ = S compound AS-106
X₁ = X₂ = Se compound ASe-106
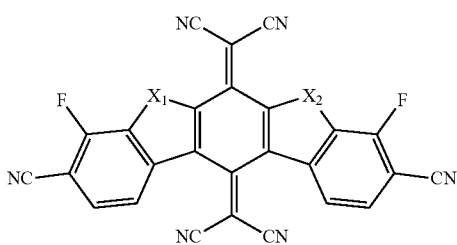
X₁ = X₂ = O compound AO-107
X₁ = X₂ = S compound AS-107
X₁ = X₂ = Se compound ASe-107
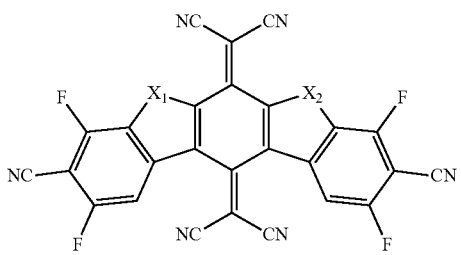
X₁ = X₂ = O compound AO-108
X₁ = X₂ = S compound AS-108
X₁ = X₂ = Se compound ASe-108
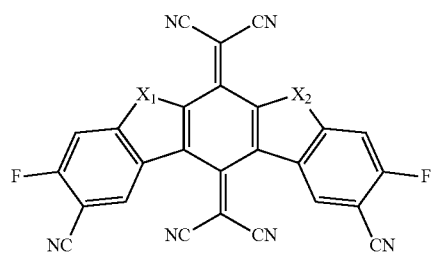

X₁ = X₂ = O compound AO-109
X₁ = X₂ = S compound AS-109
X₁ = X₂ = Se compound ASe-109
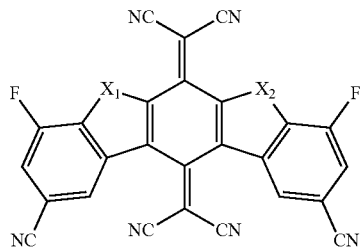
X₁ = X₂ = O compound AO-110
X₁ = X₂ = S compound AS-110
X₁ = X₂ = Se compound ASe-110
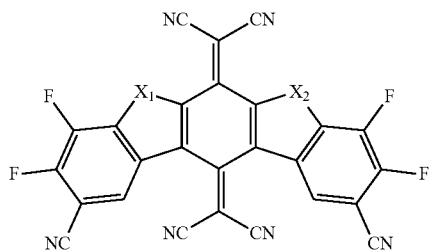
X₁ = X₂ = O compound AO-111
X₁ = X₂ = S compound AS-111
X₁ = X₂ = Se compound ASe-111
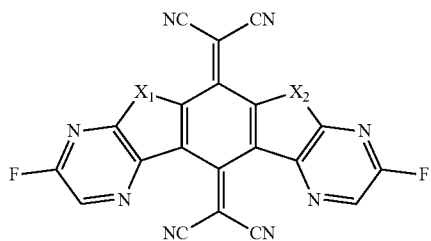
X₁ = X₂ = O compound AO-112
X₁ = X₂ = S compound AS-112
X₁ = X₂ = Se compound ASe-112
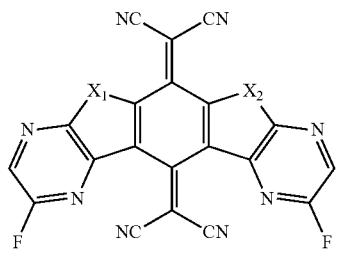
X₁ = X₂ = O compound AO-113
X₁ = X₂ = S compound AS-113
X₁ = X₂ = Se compound ASe-113

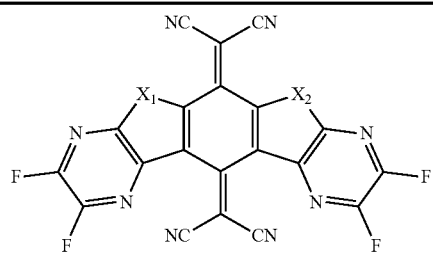
X₁ = X₂ = O compound AO-114
X₁ = X₂ = S compound AS-114
X₁ = X₂ = Se compound ASe-114
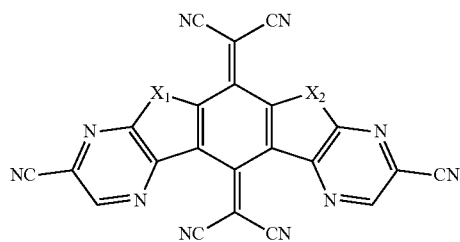
X₁ = X₂ = O compound AO-115
X₁ = X₂ = S compound AS-115
X₁ = X₂ = Se compound ASe-115
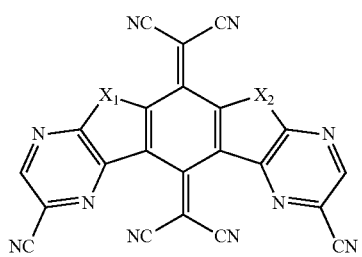
X₁ = X₂ = O compound AO-116
X₁ = X₂ = S compound AS-116
X₁ = X₂ = Se compound ASe-116
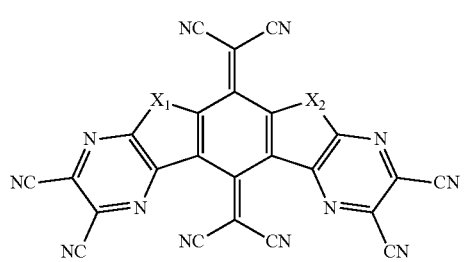
X₁ = X₂ = O compound AO-117
X₁ = X₂ = S compound AS-117
X₁ = X₂ = Se compound ASe-117
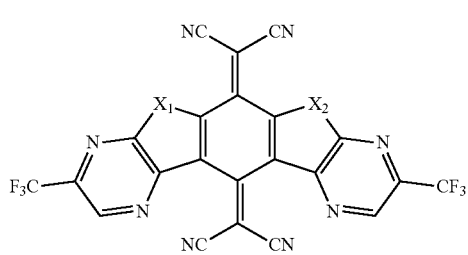

X₁ = X₂ = O compound AO-118
X₁ = X₂ = S compound AS-118
X₁ = X₂ = Se compound ASe-118
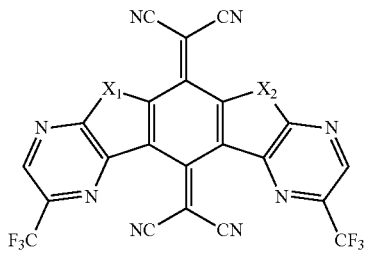
X₁ = X₂ = O compound AO-119
X₁ = X₂ = S compound AS-119
X₁ = X₂ = Se compound ASe-119
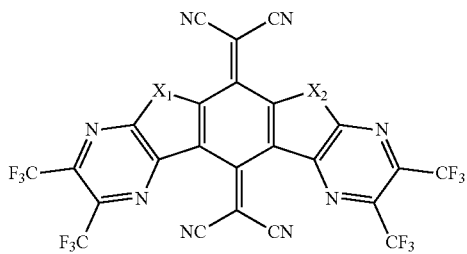
X₁ = X₂ = O compound AO-120
X₁ = X₂ = S compound AS-120
X₁ = X₂ = Se compound ASe-120
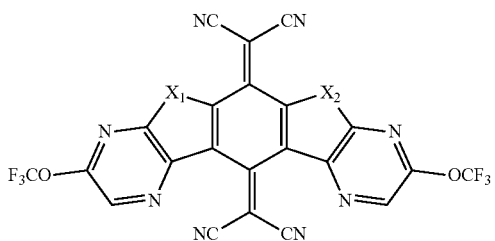
X₁ = X₂ = O compound AO-121
X₁ = X₂ = S compound AS-121
X₁ = X₂ = Se compound ASe-121
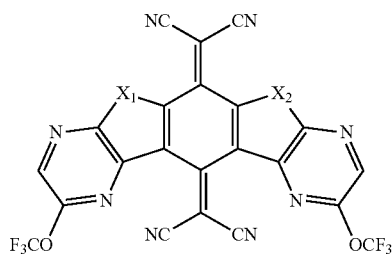
X₁ = X₂ = O compound AO-122
X₁ = X₂ = S compound AS-122
X₁ = X₂ = Se compound ASe-122

-continued
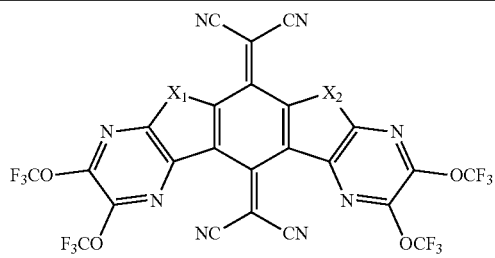
X₁ = X₂ = O compound AO-123
X₁ = X₂ = S compound AS-123
X₁ = X₂ = Se compound ASe-123
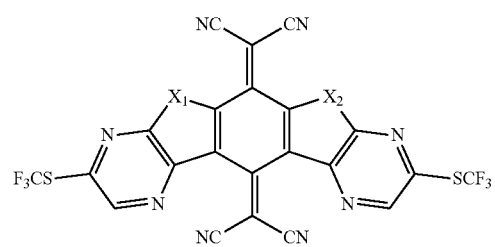
X₁ = X₂ = O compound AO-124
X₁ = X₂ = S compound AS-124
X₁ = X₂ = Se compound ASe-124
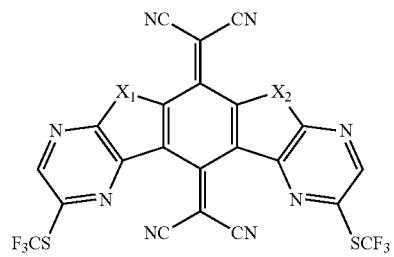
X₁ = X₂ = O compound AO-125
X₁ = X₂ = S compound AS-125
X₁ = X₂ = Se compound ASe-125
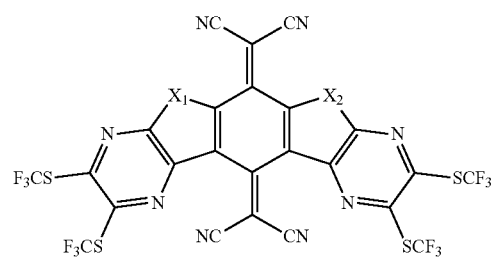
X₁ = X₂ = O compound AO-126
X₁ = X₂ = S compound AS-126
X₁ = X₂ = Se compound ASe-126
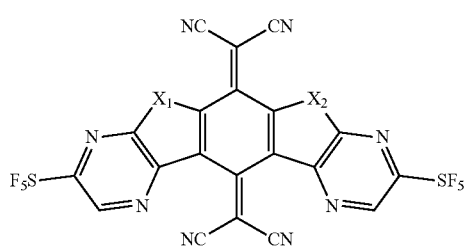

X₁ = X₂ = O compound AO-127
X₁ = X₂ = S compound AS-127
X₁ = X₂ = Se compound ASe-127
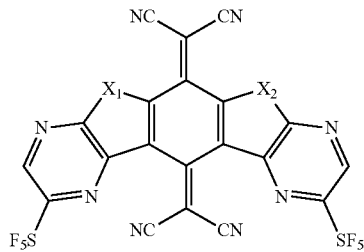
X₁ = X₂ = O compound AO-128
X₁ = X₂ = S compound AS-128
X₁ = X₂ = Se compound ASe-128
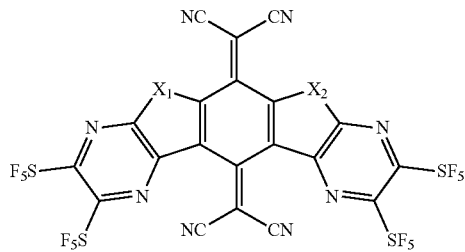
X₁ = X₂ = O compound AO-129
X₁ = X₂ = S compound AS-129
X₁ = X₂ = Se compound ASe-129
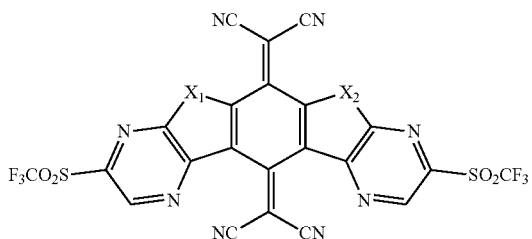
X₁ = X₂ = O compound AO-130
X₁ = X₂ = S compound AS-130
X₁ = X₂ = Se compound ASe-130
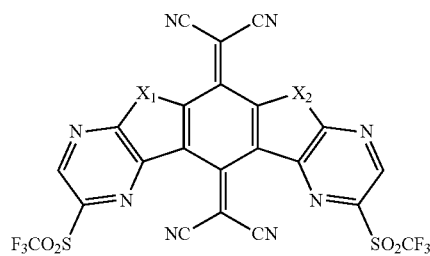
X₁ = X₂ = O compound AO-131
X₁ = X₂ = S compound AS-131
X₁ = X₂ = Se compound ASe-131

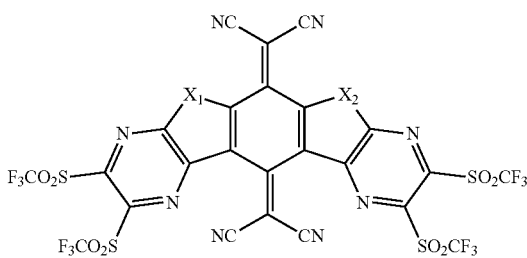
X₁ = X₂ = O compound AO-132
X₁ = X₂ = S compound AS-132
X₁ = X₂ = Se compound ASe-132
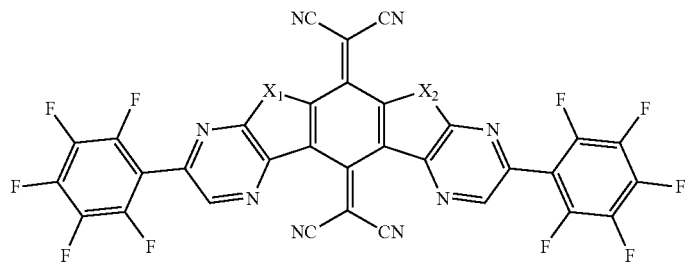
X₁ = X₂ = O compound AO-133
X₁ = X₂ = S compound AS-133
X₁ = X₂ = Se compound ASe-133
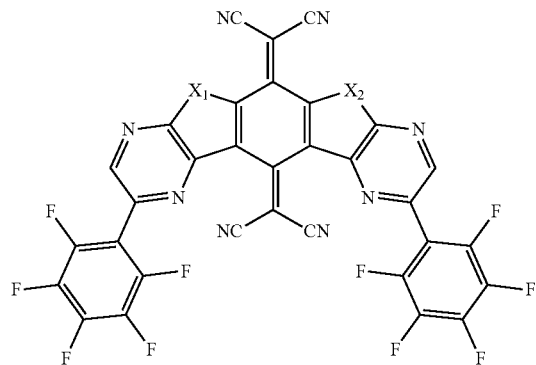
X₁ = X₂ = O compound AO-134
X₁ = X₂ = S compound AS-134
X₁ = X₂ = Se compound ASe-134
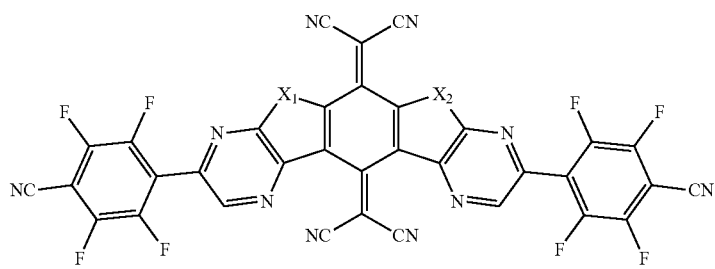
X₁ = X₂ = O compound AO-135
X₁ = X₂ = S compound AS-135
X₁ = X₂ = Se compound ASe-135

-continued
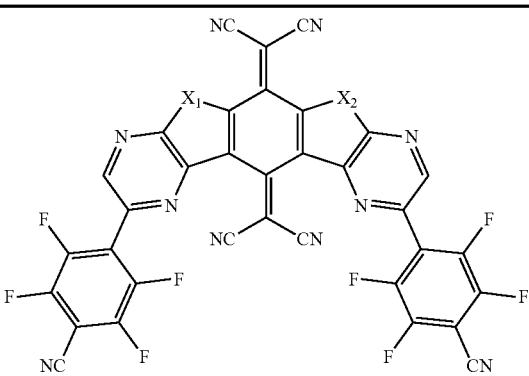
X₁ = X₂ = O compound AO-136
X₁ = X₂ = S compound AS-136
X₁ = X₂ = Se compound ASe-136
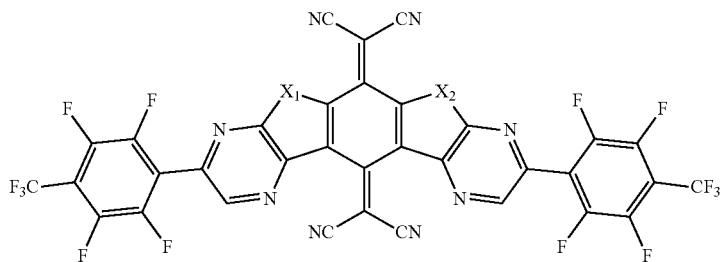
X₁ = X₂ = O compound AO-137
X₁ = X₂ = S compound AS-137
X₁ = X₂ = Se compound ASe-137
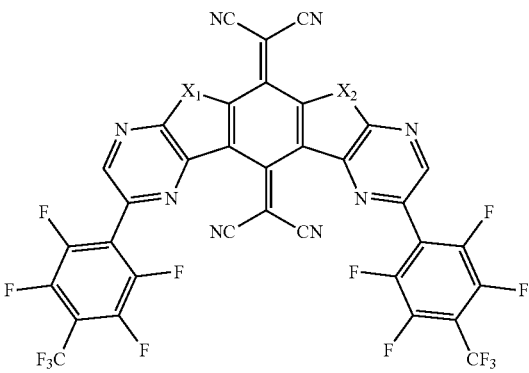
X₁ = X₂ = O compound AO-138
X₁ = X₂ = S compound AS-138
X₁ = X₂ = Se compound ASe-138
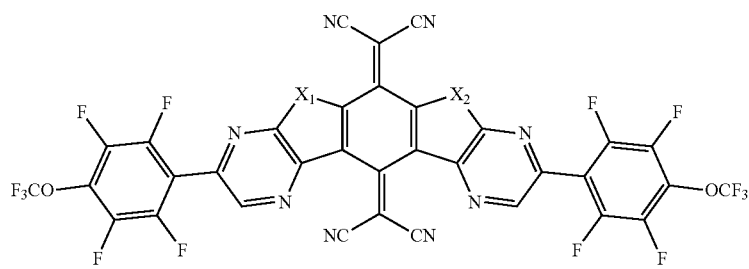
X₁ = X₂ = O compound AO-139
X₁ = X₂ = S compound AS-139
X₁ = X₂ = Se compound ASe-139

-continued
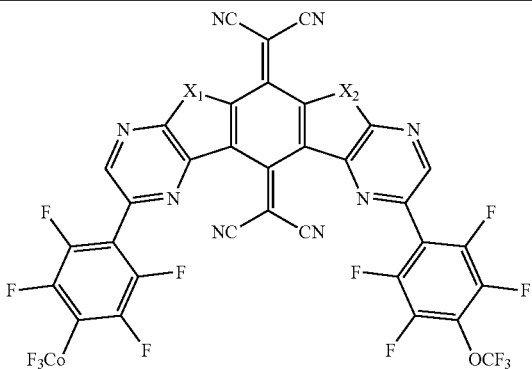
X₁ = X₂ = O compound AO-140
X₁ = X₂ = S compound AS-140
X₁ = X₂ = Se compound ASe-140
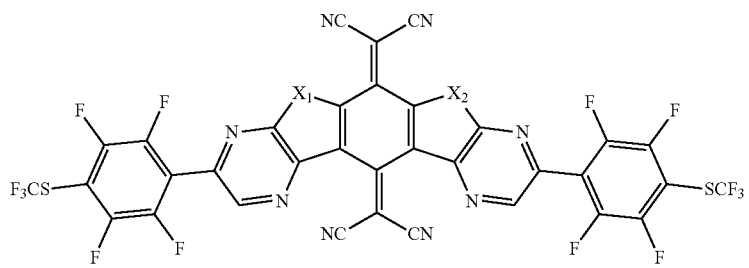
X₁ = X₂ = O compound AO-141
X₁ = X₂ = S compound AS-141
X₁ = X₂ = Se compound ASe-141
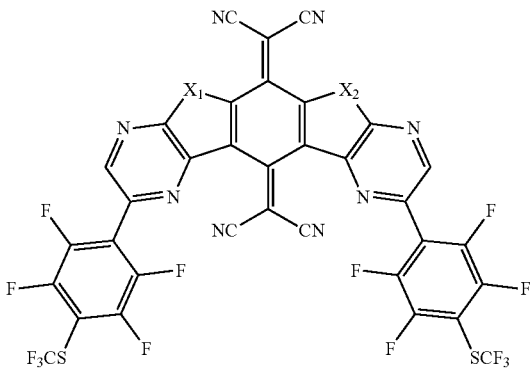
X₁ = X₂ = O compound AO-142
X₁ = X₂ = S compound AS-142
X₁ = X₂ = Se compound ASe-142
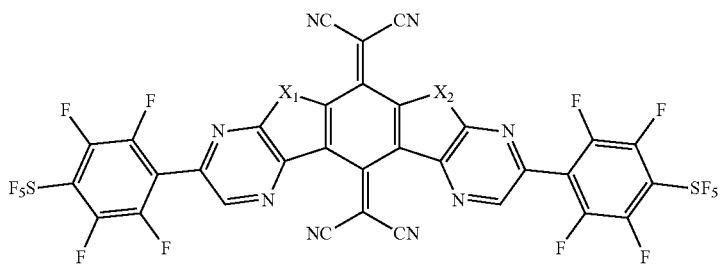
X₁ = X₂ = O compound AO-143
X₁ = X₂ = S compound AS-143
X₁ = X₂ = Se compound ASe-143

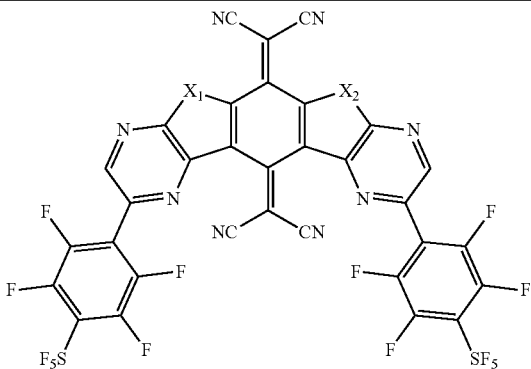
X₁ = X₂ = O compound AO-144
X₁ = X₂ = S compound AS-144
X₁ = X₂ = Se compound ASe-144
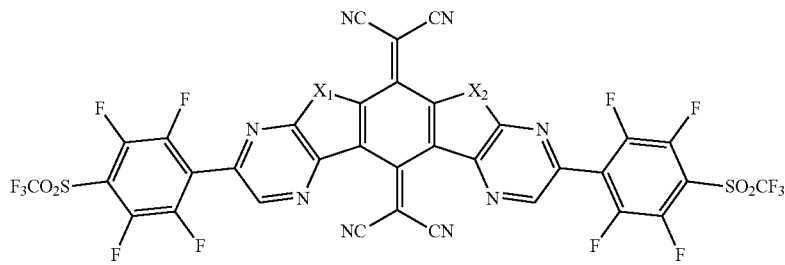
X₁ = X₂ = O compound AO-145
X₁ = X₂ = S compound AS-145
X₁ = X₂ = Se compound ASe-145
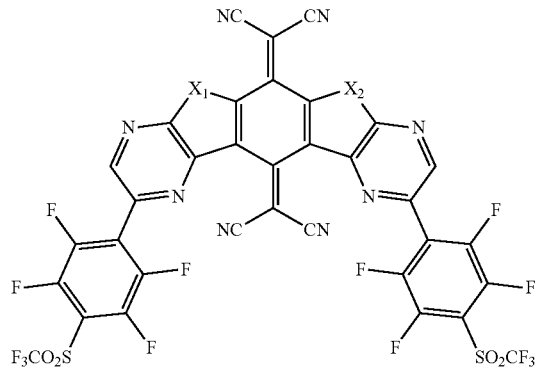
X₁ = X₂ = O compound AO-146
X₁ = X₂ = S compound AS-146
X₁ = X₂ = Se compound ASe-146
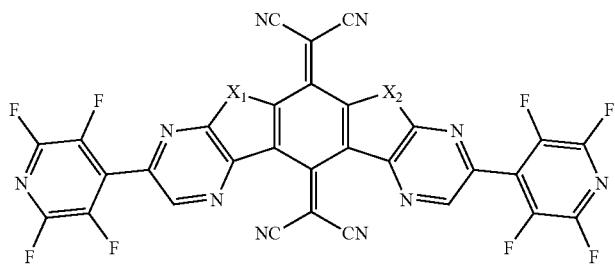
X₁ = X₂ = O compound AO-147
X₁ = X₂ = S compound AS-147
X₁ = X₂ = Se compound ASe-147

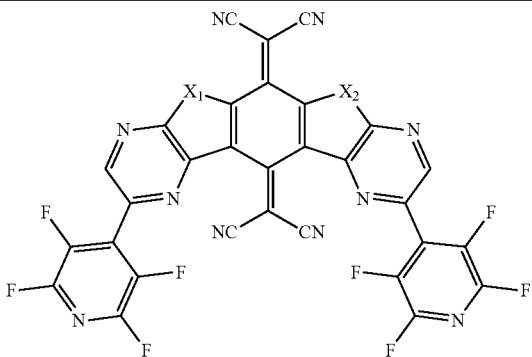
X₁ = X₂ = O compound AO-148
X₁ = X₂ = S compound AS-148
X₁ = X₂ = Se compound ASe-148
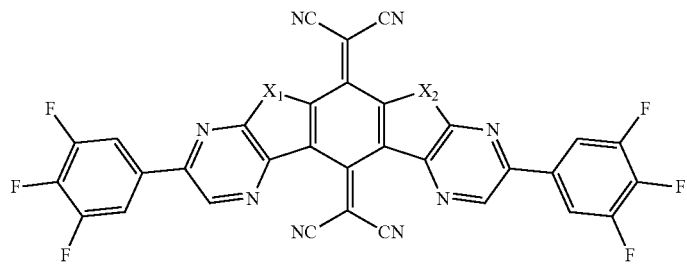
X₁ = X₂ = O compound AO-149
X₁ = X₂ = S compound AS-149
X₁ = X₂ = Se compound ASe-149
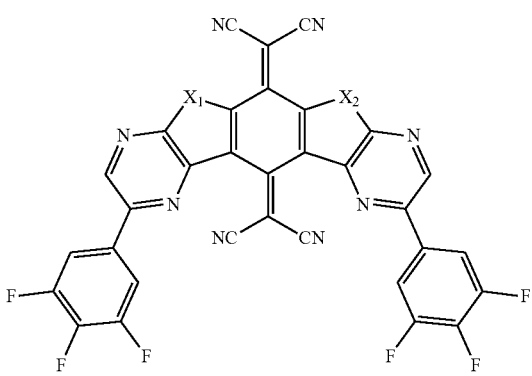
X₁ = X₂ = O compound AO-150
X₁ = X₂ = S compound AS-150
X₁ = X₂ = Se compound ASe-150
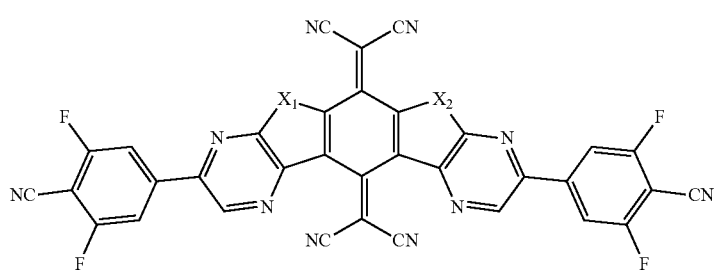
X₁ = X₂ = O compound AO-151
X₁ = X₂ = S compound AS-151
X₁ = X₂ = Se compound ASe-151

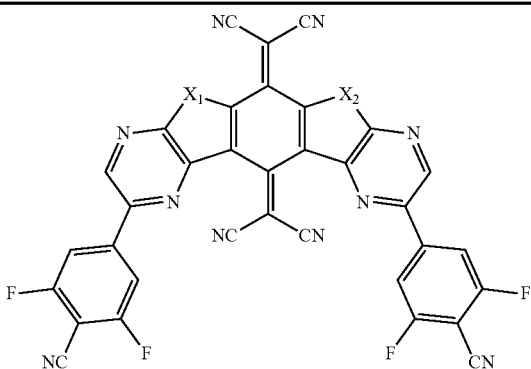
X₁ = X₂ = O compound AO-152
X₁ = X₂ = S compound AS-152
X₁ = X₂ = Se compound ASe-152
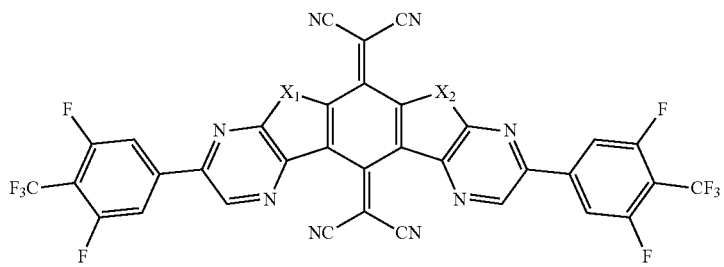
X₁ = X₂ = O compound AO-153
X₁ = X₂ = S compound AS-153
X₁ = X₂ = Se compound ASe-153
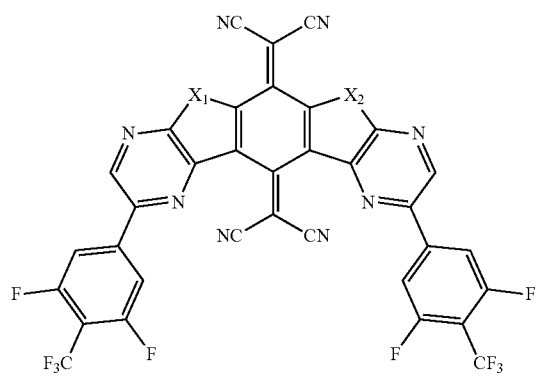
X₁ = X₂ = O compound AO-154
X₁ = X₂ = S compound AS-154
X₁ = X₂ = Se compound ASe-154
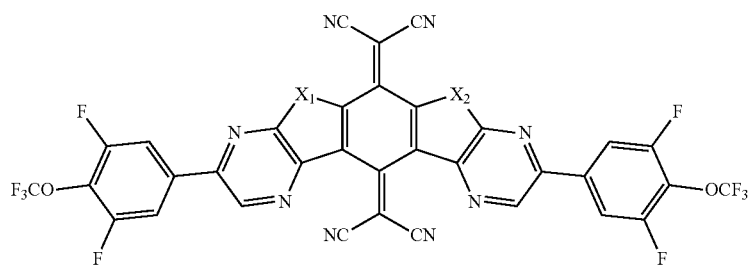
X₁ = X₂ = O compound AO-155
X₁ = X₂ = S compound AS-155
X₁ = X₂ = Se compound ASe-155

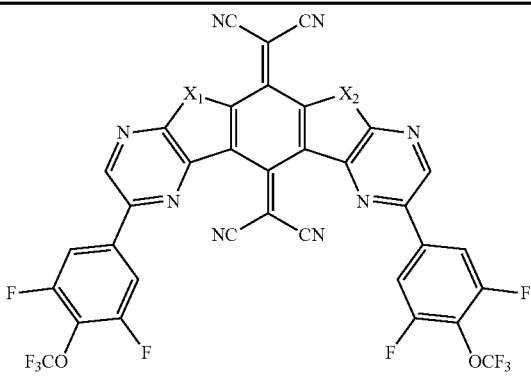
X₁ = X₂ = O compound AO-156
X₁ = X₂ = S compound AS-156
X₁ = X₂ = Se compound ASe-156
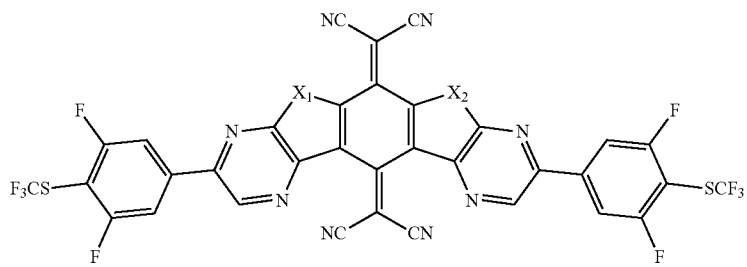
X₁ = X₂ = O compound AO-157
X₁ = X₂ = S compound AS-157
X₁ = X₂ = Se compound ASe-157
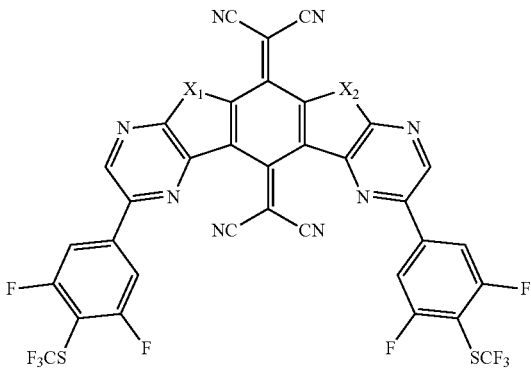
X₁ = X₂ = O compound AO-158
X₁ = X₂ = S compound AS-158
X₁ = X₂ = Se compound ASe-158
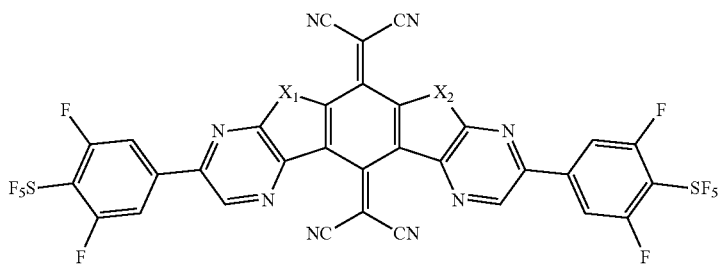
X₁ = X₂ = O compound AO-159
X₁ = X₂ = S compound AS-159
X₁ = X₂ = Se compound ASe-159

-continued
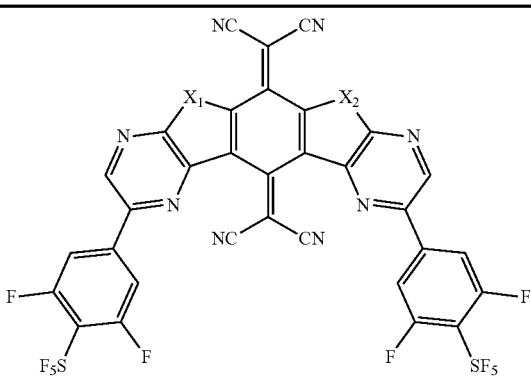
X₁ = X₂ = O compound AO-160
X₁ = X₂ = S compound AS-160
X₁ = X₂ = Se compound ASe-160
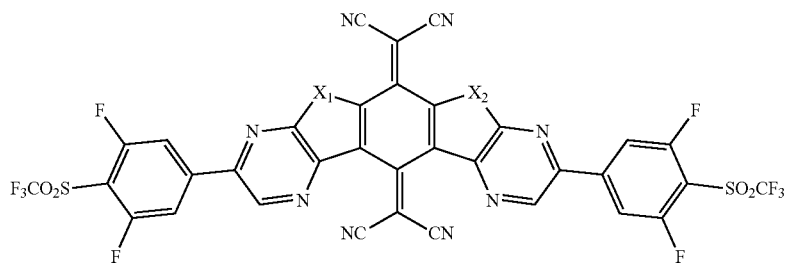
X₁ = X₂ = O compound AO-161
X₁ = X₂ = S compound AS-161
X₁ = X₂ = Se compound ASe-161
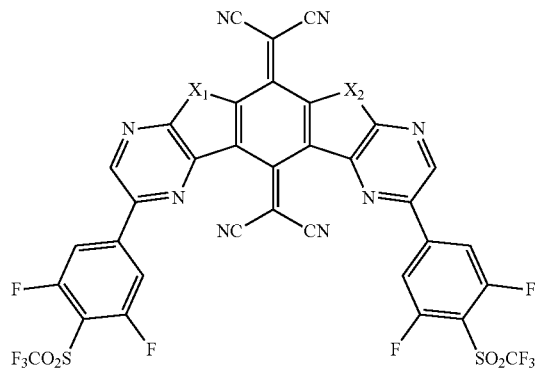
X₁ = X₂ = O compound AO-162
X₁ = X₂ = S compound AS-162
X₁ = X₂ = Se compound ASe-162
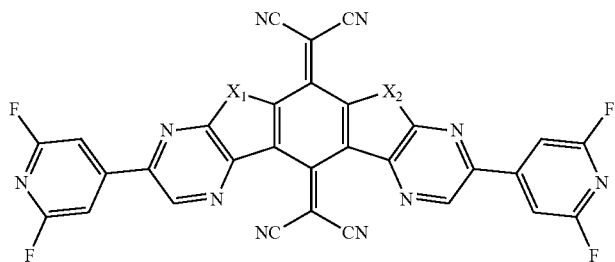
X₁ = X₂ = O compound AO-163
X₁ = X₂ = S compound AS-163
X₁ = X₂ = Se compound ASe-163

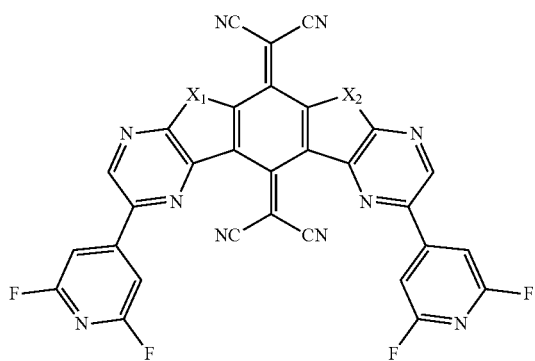
X₁ = X₂ = O compound AO-164
X₁ = X₂ = S compound AS-164
X₁ = X₂ = Se compound ASe-164
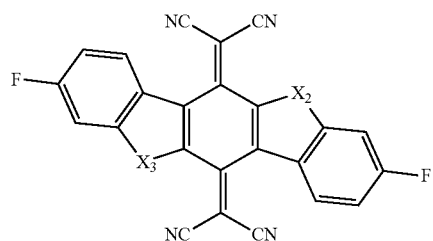
X₃ = X₂ = O compound BO-1
X₃ = X₂ = S compound BS-1
X₃ = X₂ = Se compound BSe-1
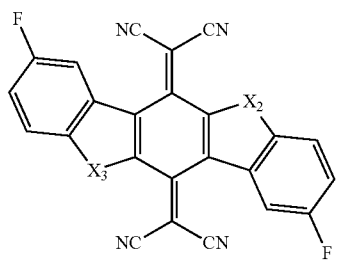
X₃ = X₂ = O compound BO-2
X₃ = X₂ = S compound BS-2
X₃ = X₂ = Se compound BSe-2
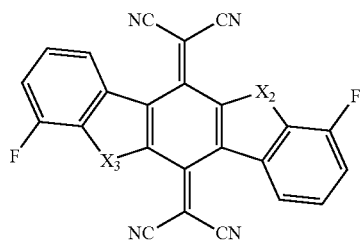
X₃ = X₂ = O compound BO-3
X₃ = X₂ = S compound BS-3
X₃ = X₂ = Se compound BSe-3

-continued
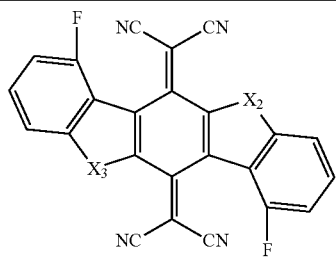
X₃ = X₂ = O compound BO-4
X₃ = X₂ = S compound BS-4
X₃ = X₂ = Se compound BSe-4
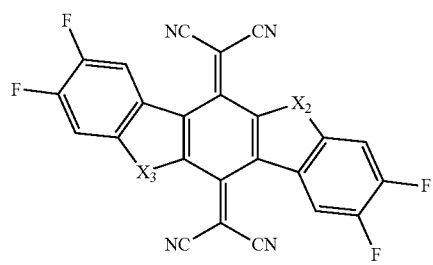
X₃ = X₂ = O compound BO-5
X₃ = X₂ = S compound BS-5
X₃ = X₂ = Se compound BSe-5
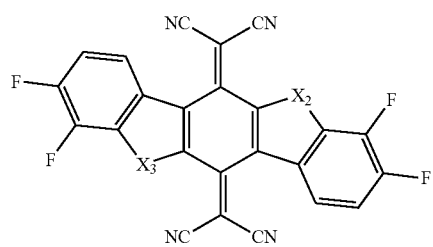
X₃ = X₂ = O compound BO-6
X₃ = X₂ = S compound BS-6
X₃ = X₂ = Se compound BSe-6
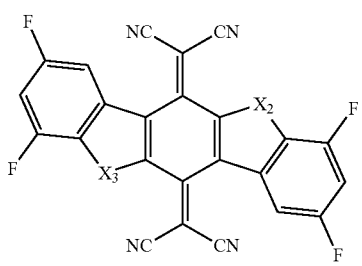
X₃ = X₂ = O compound BO-7
X₃ = X₂ = S compound BS-7
X₃ = X₂ = Se compound BSe-7
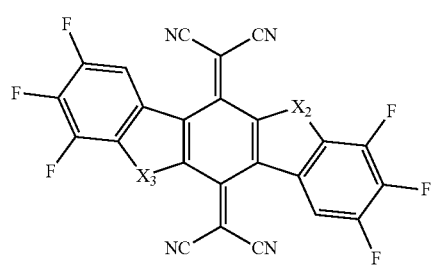

X₃ = X₂ = O compound BO-8
X₃ = X₂ = S compound BS-8
X₃ = X₂ = Se compound BSe-8
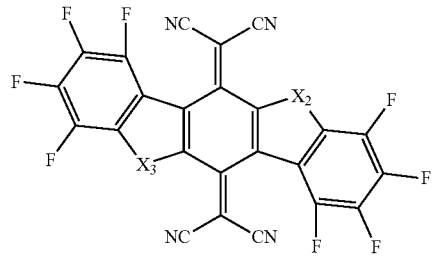
X₃ = X₂ = O compound BO-9
X₃ = X₂ = S compound BS-9
X₃ = X₂ = Se compound BSe-9
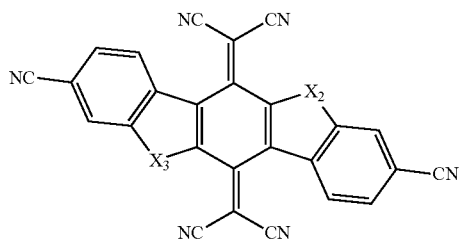
X₃ = X₂ = O compound BO-10
X₃ = X₂ = S compound BS-10
X₃ = X₂ = Se compound BSe-10
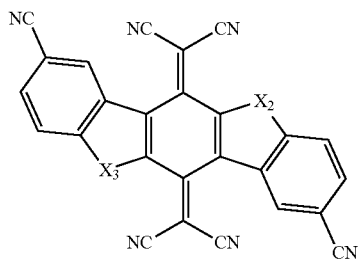
X₃ = X₂ = O compound BO-11
X₃ = X₂ = S compound BS-11
X₃ = X₂ = Se compound BSe-11
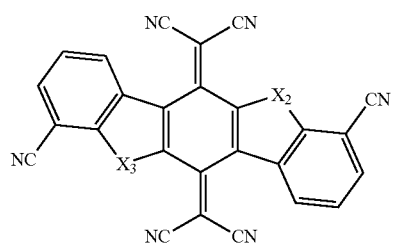
X₃ = X₂ = O compound BO-12
X₃ = X₂ = S compound BS-12
X₃ = X₂ = Se compound BSe-12

-continued
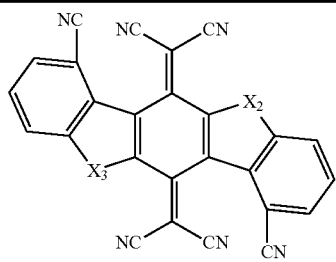
X₃ = X₂ = O compound BO-13
X₃ = X₂ = S compound BS-13
X₃ = X₂ = Se compound BSe-13
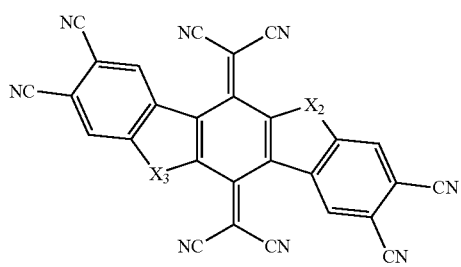
X₃ = X₂ = O compound BO-14
X₃ = X₂ = S compound BS-14
X₃ = X₂ = Se compound BSe-14
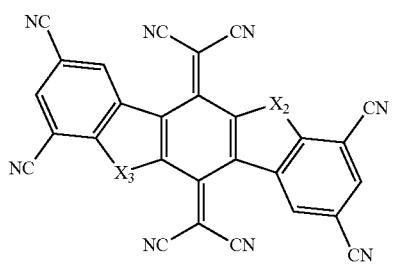
X₃ = X₂ = O compound BO-15
X₃ = X₂ = S compound BS-15
X₃ = X₂ = Se compound BSe-15
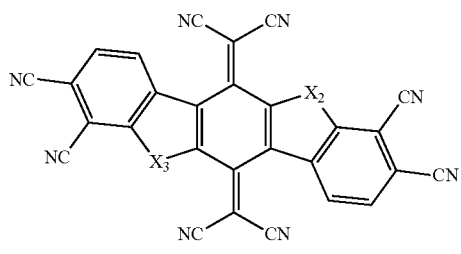
X₃ = X₂ = O compound BO-16
X₃ = X₂ = S compound BS-16
X₃ = X₂ = Se compound BSe-16
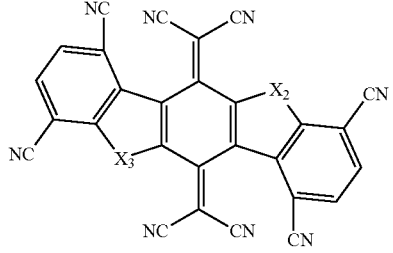

-continued
X₃ = X₂ = O compound BO-17
X₃ = X₂ = S compound BS-17
X₃ = X₂ = Se compound BSe-17
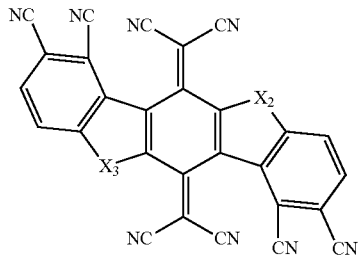
X₃ = X₂ = O compound BO-18
X₃ = X₂ = S compound BS-18
X₃ = X₂ = Se compound BSe-18
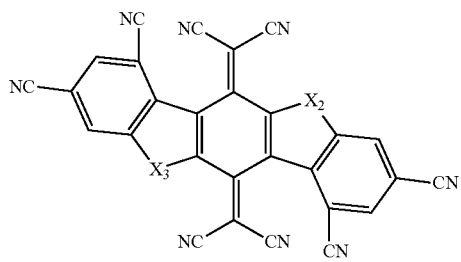
X₃ = X₂ = O compound BO-19
X₃ = X₂ = S compound BS-19
X₃ = X₂ = Se compound BSe-19
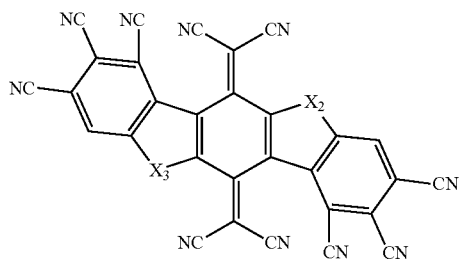
X₃ = X₂ = O compound BO-20
X₃ = X₂ = S compound BS-20
X₃ = X₂ = Se compound BSe-20
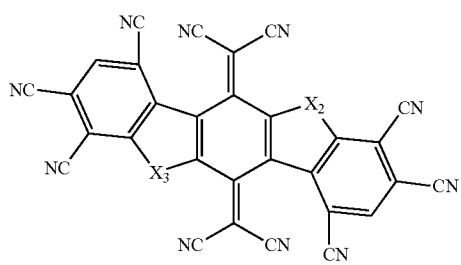
X₃ = X₂ = O compound BO-21
X₃ = X₂ = S compound BS-21
X₃ = X₂ = Se compound BSe-21

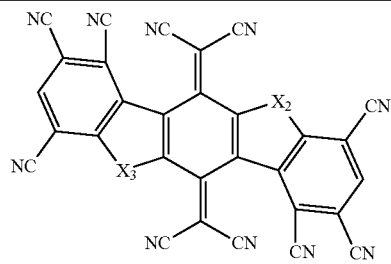
X₃ = X₂ = O compound BO-22
X₃ = X₂ = S compound BS-22
X₃ = X₂ = Se compound BSe-22
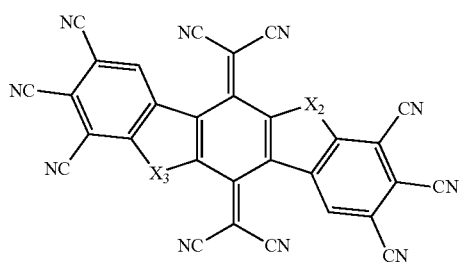
X₃ = X₂ = O compound BO-23
X₃ = X₂ = S compound BS-23
X₃ = X₂ = Se compound BSe-23
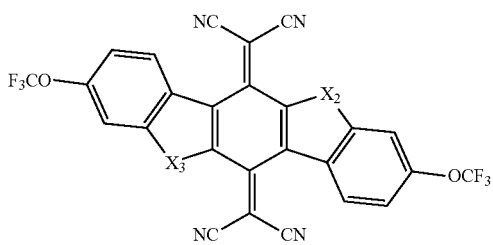
X₃ = X₂ = O compound BO-24
X₃ = X₂ = S compound BS-24
X₃ = X₂ = Se compound BSe-24
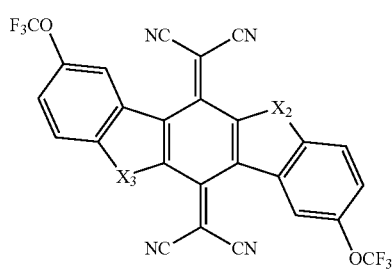
X₃ = X₂ = O compound BO-25
X₃ = X₂ = S compound BS-25
X₃ = X₂ = Se compound BSe-25
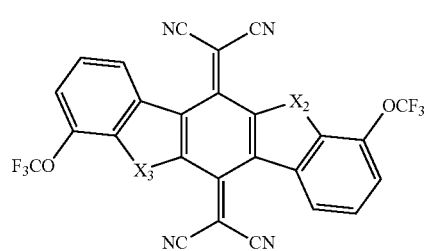

X₃ = X₂ = O compound BO-26
X₃ = X₂ = S compound BS-26
X₃ = X₂ = Se compound BSe-26
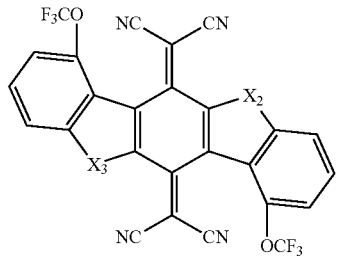
X₃ = X₂ = O compound BO-27
X₃ = X₂ = S compound BS-27
X₃ = X₂ = Se compound BSe-27
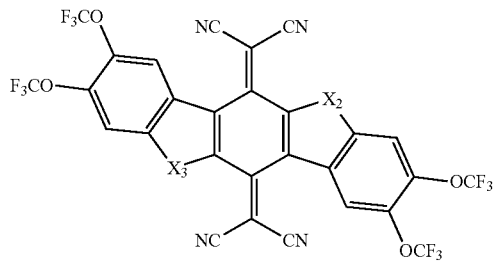
X₃ = X₂ = O compound BO-28
X₃ = X₂ = S compound BS-28
X₃ = X₂ = Se compound BSe-28
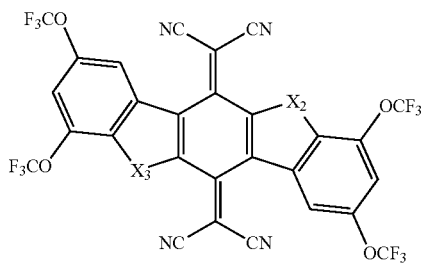
X₃ = X₂ = O compound BO-29
X₃ = X₂ = S compound BS-29
X₃ = X₂ = Se compound BSe-29
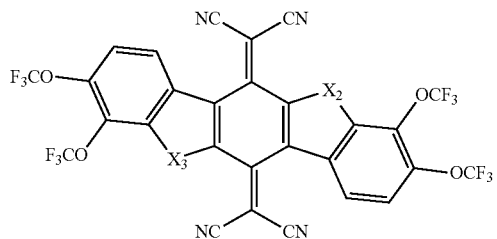
X₃ = X₂ = O compound BO-30
X₃ = X₂ = S compound BS-30
X₃ = X₂ = Se compound BSe-30

-continued
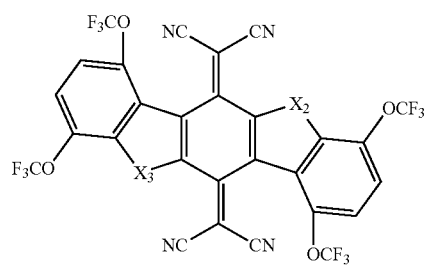
X₃ = X₂ = O compound BO-31
X₃ = X₂ = S compound BS-31
X₃ = X₂ = Se compound BSe-31
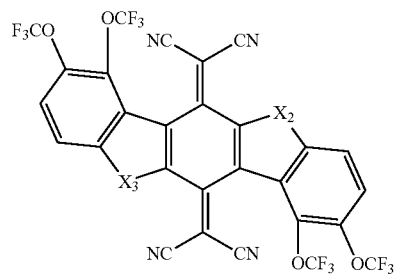
X₃ = X₂ = O compound BO-32
X₃ = X₂ = S compound BS-32
X₃ = X₂ = Se compound BSe-32
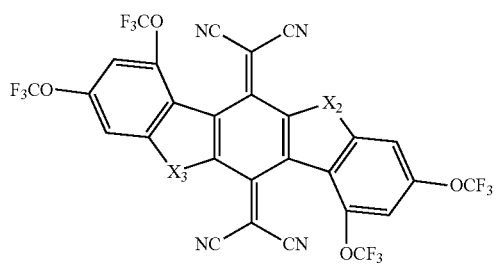
X₃ = X₂ = O compound BO-33
X₃ = X₂ = S compound BS-33
X₃ = X₂ = Se compound BSe-33
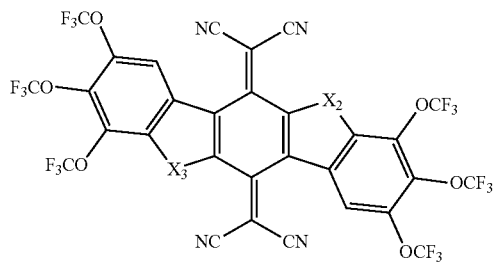
X₃ = X₂ = O compound BO-34
X₃ = X₂ = S compound BS-34
X₃ = X₂ = Se compound BSe-34

-continued
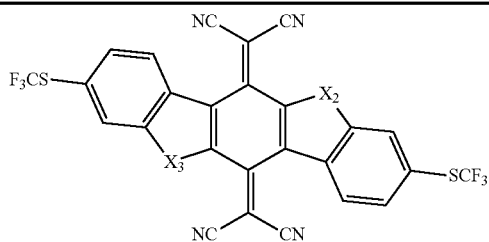
X₃ = X₂ = O compound BO-35
X₃ = X₂ = S compound BS-35
X₃ = X₂ = Se compound BSe-35
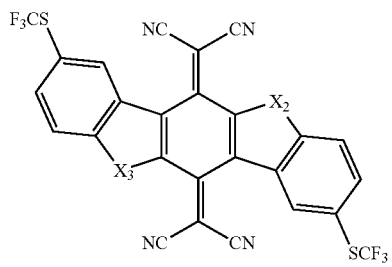
X₃ = X₂ = O compound BO-36
X₃ = X₂ = S compound BS-36
X₃ = X₂ = Se compound BSe-36
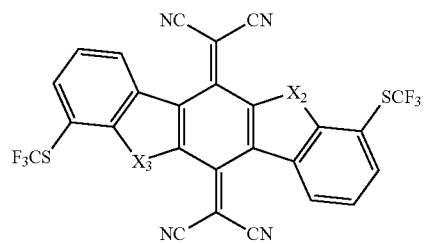
X₃ = X₂ = O compound BO-37
X₃ = X₂ = S compound BS-37
X₃ = X₂ = Se compound BSe-37
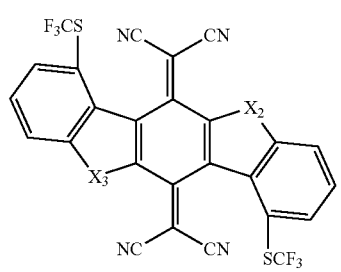
X₃ = X₂ = O compound BO-38
X₃ = X₂ = S compound BS-38
X₃ = X₂ = Se compound BSe-38
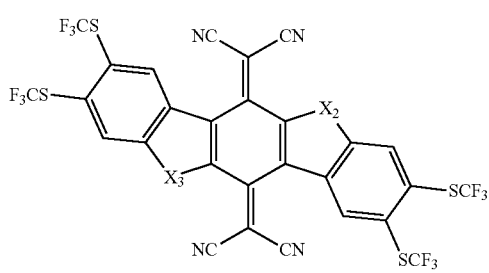

X₃ = X₂ = O compound BO-39
X₃ = X₂ = S compound BS-39
X₃ = X₂ = Se compound BSe-39
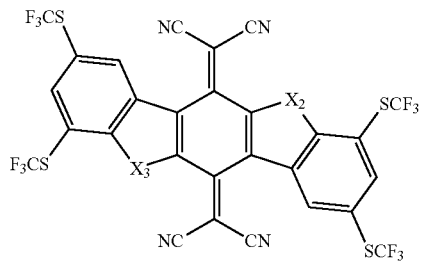
X₃ = X₂ = O compound BO-40
X₃ = X₂ = S compound BS-40
X₃ = X₂ = Se compound BSe-40
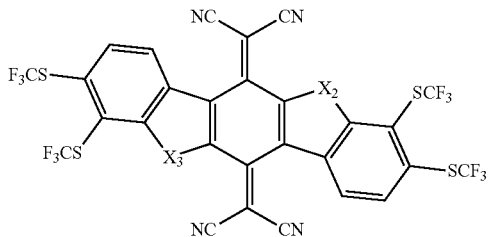
X₃ = X₂ = O compound BO-41
X₃ = X₂ = S compound BS-41
X₃ = X₂ = Se compound BSe-41
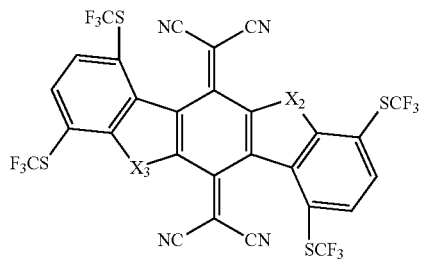
X₃ = X₂ = O compound BO-42
X₃ = X₂ = S compound BS-42
X₃ = X₂ = Se compound BSe-42
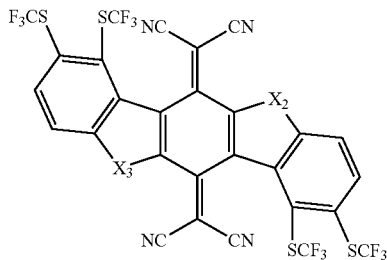
X₃ = X₂ = O compound BO-43
X₃ = X₂ = S compound BS-43
X₃ = X₂ = Se compound BSe-43

-continued
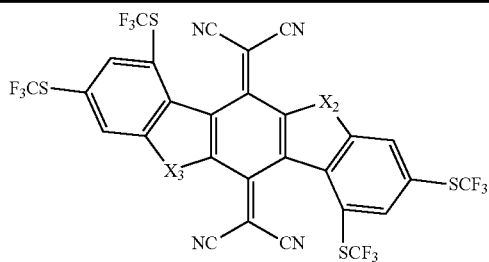
X₃ = X₂ = O compound BO-44
X₃ = X₂ = S compound BS-44
X₃ = X₂ = Se compound BSe-44
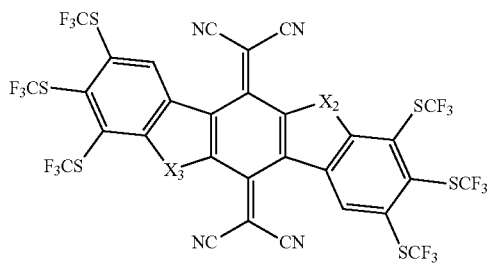
X₃ = X₂ = O compound BO-45
X₃ = X₂ = S compound BS-45
X₃ = X₂ = Se compound BSe-45
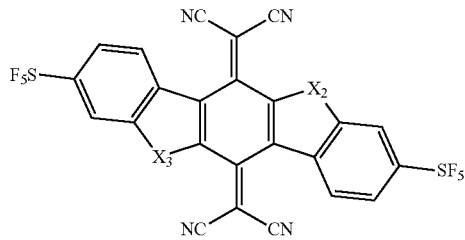
X₃ = X₂ = O compound BO-46
X₃ = X₂ = S compound BS-46
X₃ = X₂ = Se compound BSe-46
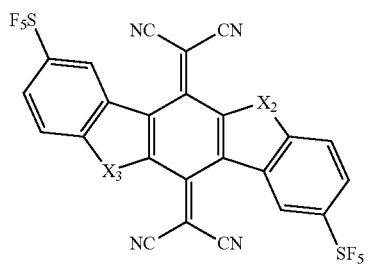
X₃ = X₂ = O compound BO-47
X₃ = X₂ = S compound BS-47
X₃ = X₂ = Se compound BSe-47
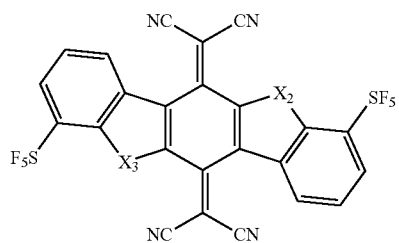

X₃ = X₂ = O compound BO-48
X₃ = X₂ = S compound BS-48
X₃ = X₂ = Se compound BSe-48
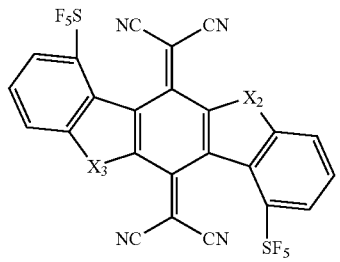
X₃ = X₂ = O compound BO-49
X₃ = X₂ = S compound BS-49
X₃ = X₂ = Se compound BSe-49
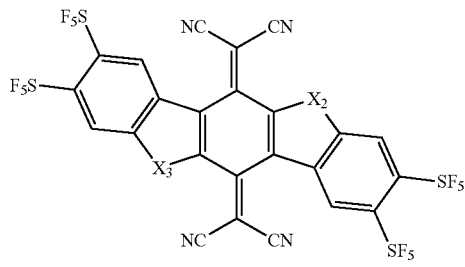
X₃ = X₂ = O compound BO-50
X₃ = X₂ = S compound BS-50
X₃ = X₂ = Se compound BSe-50
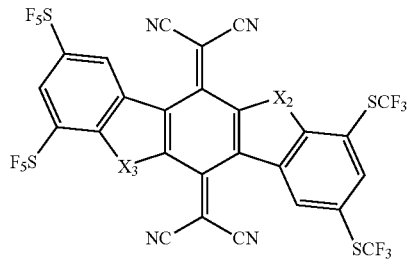
X₃ = X₂ = O compound BO-51
X₃ = X₂ = S compound BS-51
X₃ = X₂ = Se compound BSe-51
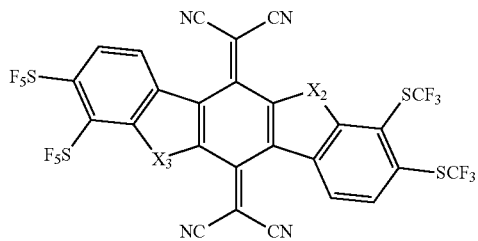
X₃ = X₂ = O compound BO-52
X₃ = X₂ = S compound BS-52
X₃ = X₂ = Se compound BSe-52

-continued
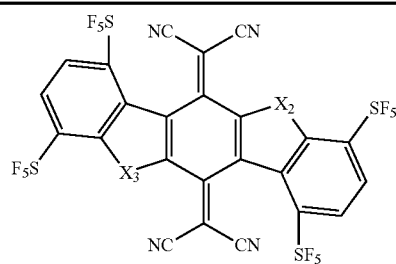
X₃ = X₂ = O compound BO-53
X₃ = X₂ = S compound BS-53
X₃ = X₂ = Se compound BSe-53
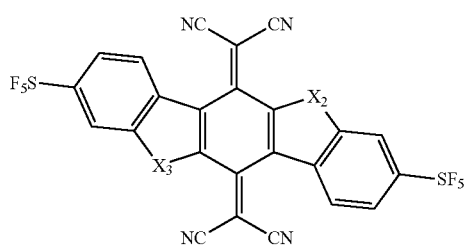
X₃ = X₂ = O compound BO-54
X₃ = X₂ = S compound BS-54
X₃ = X₂ = Se compound BSe-54
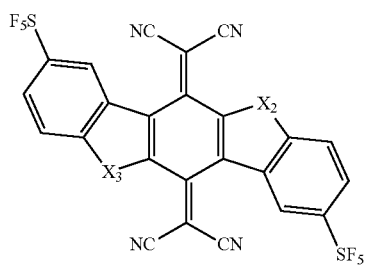
X₃ = X₂ = O compound BO-55
X₃ = X₂ = S compound BS-55
X₃ = X₂ = Se compound BSe-55
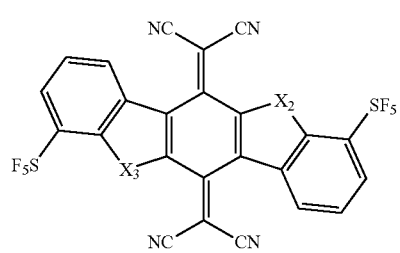
X₃ = X₂ = O compound BO-56
X₃ = X₂ = S compound BS-56
X₃ = X₂ = Se compound BSe-56
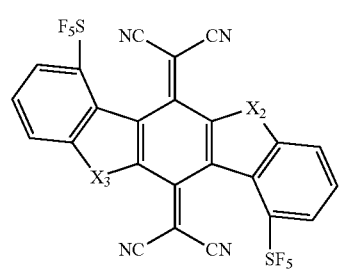

X₃ = X₂ = O compound BO-57
X₃ = X₂ = S compound BS-57
X₃ = X₂ = Se compound BSe-57
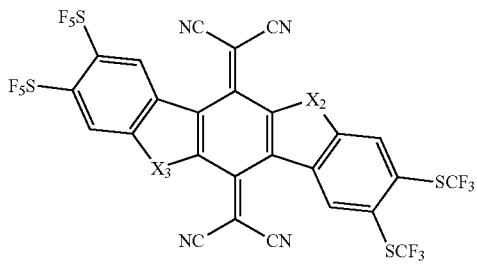
X₃ = X₂ = O compound BO-58
X₃ = X₂ = S compound BS-58
X₃ = X₂ = Se compound BSe-58
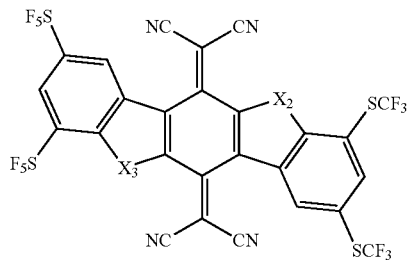
X₃ = X₂ = O compound BO-59
X₃ = X₂ = S compound BS-59
X₃ = X₂ = Se compound BSe-59
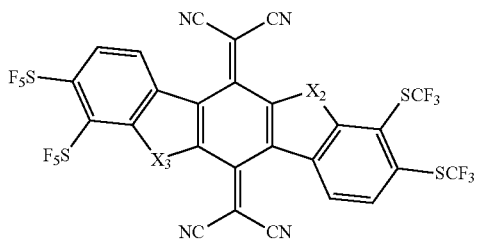
X₃ = X₂ = O compound BO-60
X₃ = X₂ = S compound BS-60
X₃ = X₂ = Se compound BSe-60
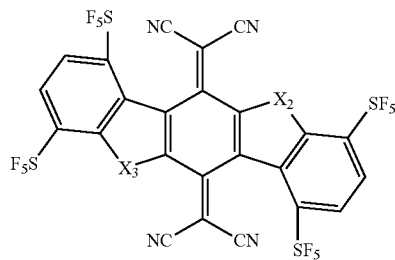
X₃ = X₂ = O compound BO-61
X₃ = X₂ = S compound BS-61
X₃ = X₂ = Se compound BSe-61

-continued
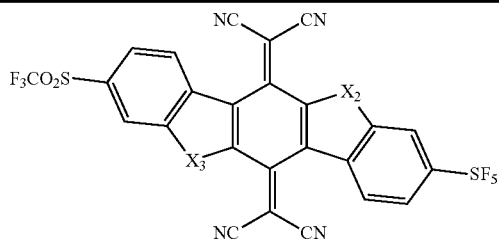
X₃ = X₂ = O compound BO-62
X₃ = X₂ = S compound BS-62
X₃ = X₂ = Se compound BSe-62
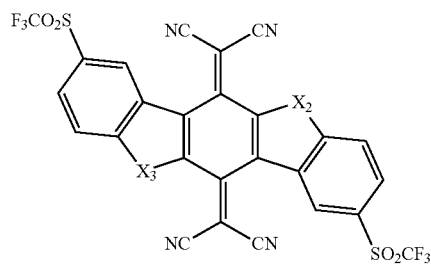
X₃ = X₂ = O compound BO-63
X₃ = X₂ = S compound BS-63
X₃ = X₂ = Se compound BSe-63
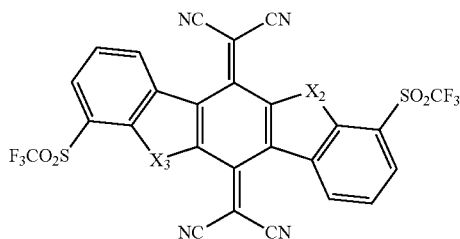
X₃ = X₂ = O compound BO-64
X₃ = X₂ = S compound BS-64
X₃ = X₂ = Se compound BSe-64
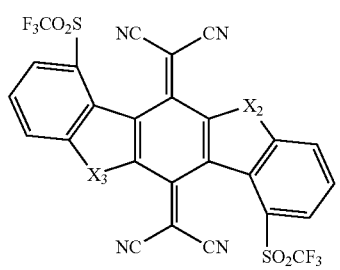
X₃ = X₂ = O compound BO-65
X₃ = X₂ = S compound BS-65
X₃ = X₂ = Se compound BSe-65
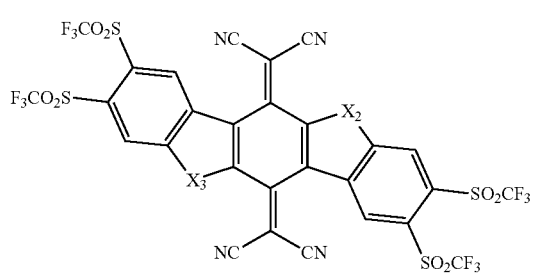

X₃ = X₂ = O compound BO-66
X₃ = X₂ = S compound BS-66
X₃ = X₂ = Se compound BSe-66
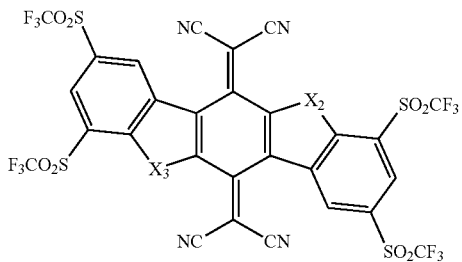
X₃ = X₂ = O compound BO-67
X₃ = X₂ = S compound BS-67
X₃ = X₂ = Se compound BSe-67
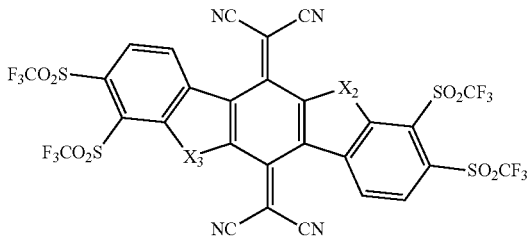
X₃ = X₂ = O compound BO-68
X₃ = X₂ = S compound BS-68
X₃ = X₂ = Se compound BSe-68
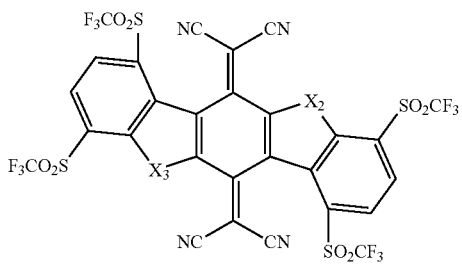
X₃ = X₂ = O compound BO-69
X₃ = X₂ = S compound BS-69
X₃ = X₂ = Se compound BSe-69
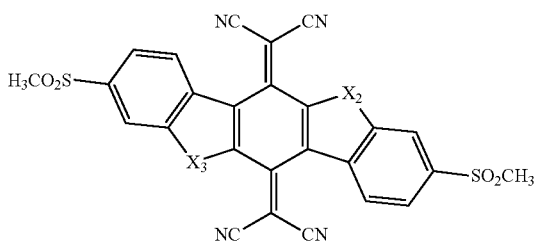
X₃ = X₂ = O compound BO-70
X₃ = X₂ = S compound BS-70
X₃ = X₂ = Se compound BSe-70

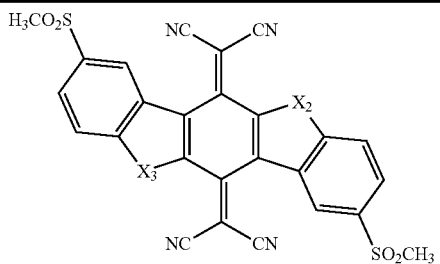
X₃ = X₂ = O compound BO-71
X₃ = X₂ = S compound BS-71
X₃ = X₂ = Se compound BSe-71
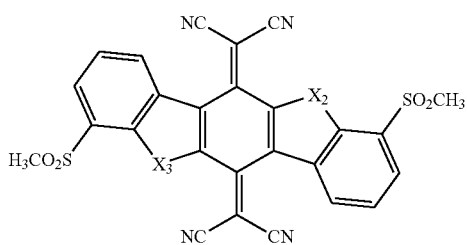
X₃ = X₂ = O compound BO-72
X₃ = X₂ = S compound BS-72
X₃ = X₂ = Se compound BSe-72
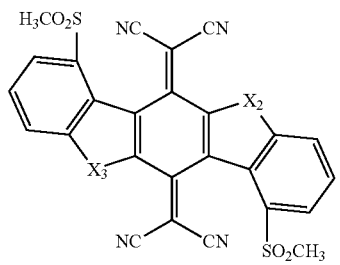
X₃ = X₂ = O compound BO-73
X₃ = X₂ = S compound BS-73
X₃ = X₂ = Se compound BSe-73
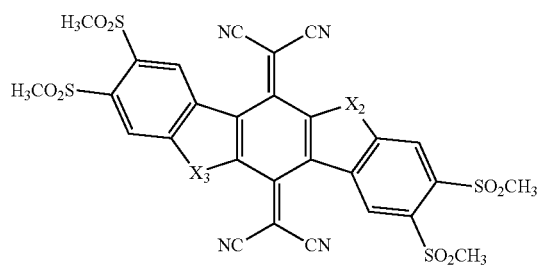
X₃ = X₂ = O compound BO-74
X₃ = X₂ = S compound BS-74
X₃ = X₂ = Se compound BSe-74
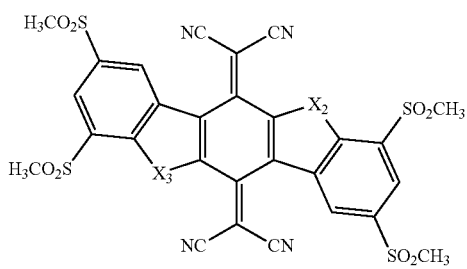

X₃ = X₂ = O compound BO-75
X₃ = X₂ = S compound BS-75
X₃ = X₂ = Se compound BSe-75
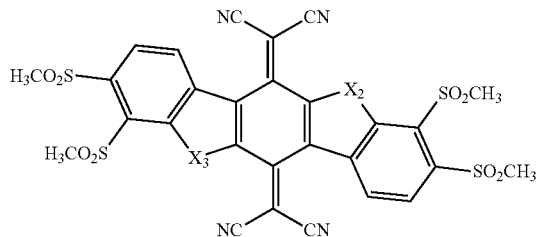
X₃ = X₂ = O compound BO-76
X₃ = X₂ = S compound BS-76
X₃ = X₂ = Se compound BSe-76
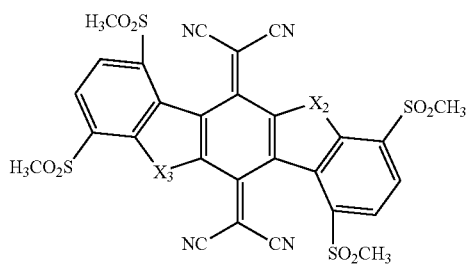
X₃ = X₂ = O compound BO-77
X₃ = X₂ = S compound BS-77
X₃ = X₂ = Se compound BSe-77
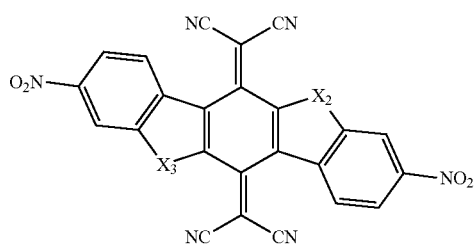
X₃ = X₂ = O compound BO-78
X₃ = X₂ = S compound BS-78
X₃ = X₂ = Se compound BSe-78
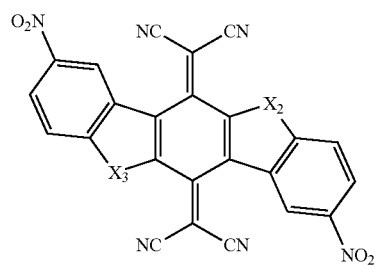
X₃ = X₂ = O compound BO-79
X₃ = X₂ = S compound BS-79
X₃ = X₂ = Se compound BSe-79

-continued
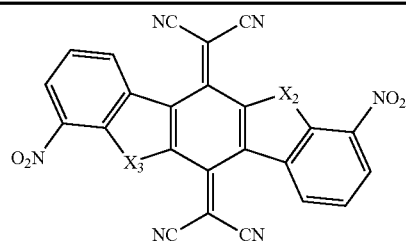
X₃ = X₂ = O compound BO-81
X₃ = X₂ = S compound BS-81
X₃ = X₂ = Se compound BSe-81
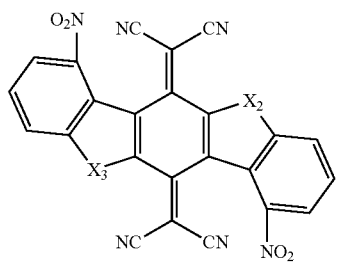
X₃ = X₂ = O compound BO-82
X₃ = X₂ = S compound BS-82
X₃ = X₂ = Se compound BSe-82
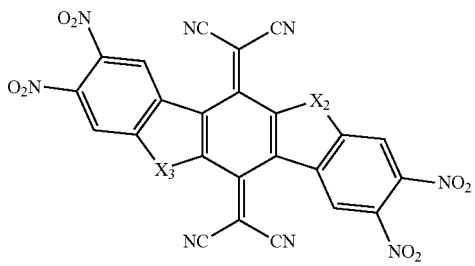
X₃ = X₂ = O compound BO-83
X₃ = X₂ = S compound BS-83
X₃ = X₂ = Se compound BSe-83
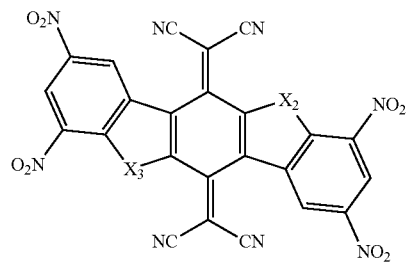
X₃ = X₂ = O compound BO-84
X₃ = X₂ = S compound BS-84
X₃ = X₂ = Se compound BSe-84
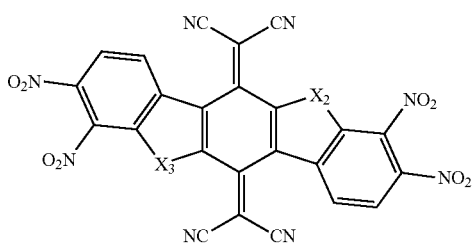

$X_3 = X_2 = O$ compound BO-85
$X_3 = X_2 = S$ compound BS-85
$X_3 = X_2 = Se$ compound BSe-85
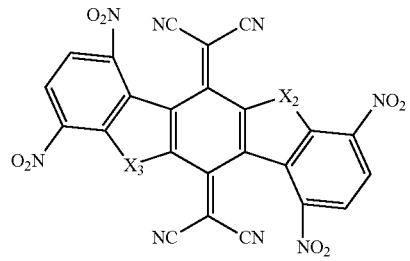
$X_3 = X_2 = O$ compound BO-86
$X_3 = X_2 = S$ compound BS-86
$X_3 = X_2 = Se$ compound BSe-86
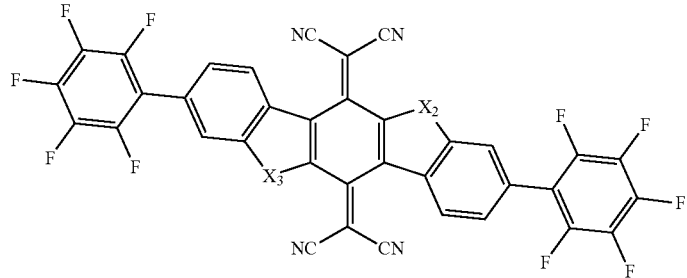
$X_3 = X_2 = O$ compound BO-87
$X_3 = X_2 = S$ compound BS-87
$X_3 = X_2 = Se$ compound BSe-87
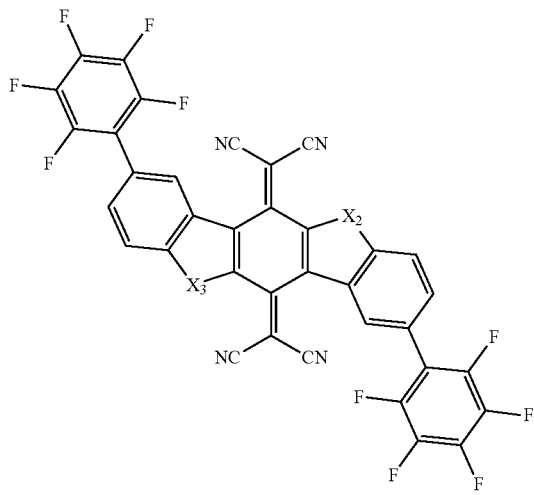
$X_3 = X_2 = O$ compound BO-88
$X_3 = X_2 = S$ compound BS-88
$X_3 = X_2 = Se$ compound BSe-88

-continued
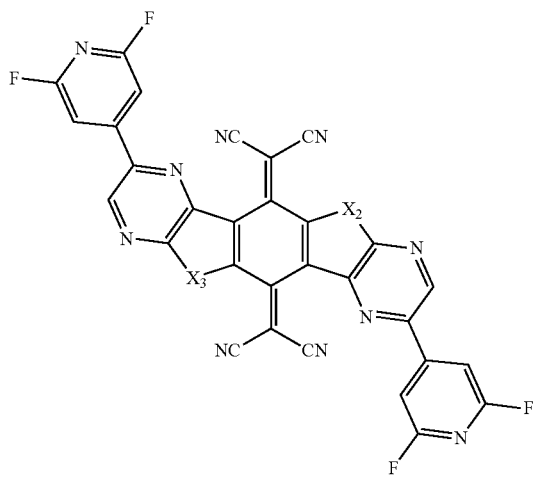
$X_3 = X_2 = O$ compound BO-89
$X_3 = X_2 = S$ compound BS-89
$X_3 = X_2 = Se$ compound BSe-89
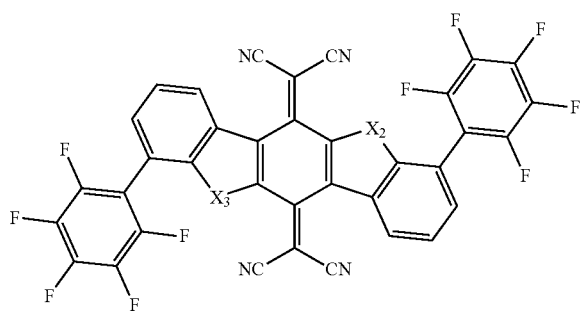
$X_3 = X_2 = O$ compound BO-90
$X_3 = X_2 = S$ compound BS-90
$X_3 = X_2 = Se$ compound BSe-90
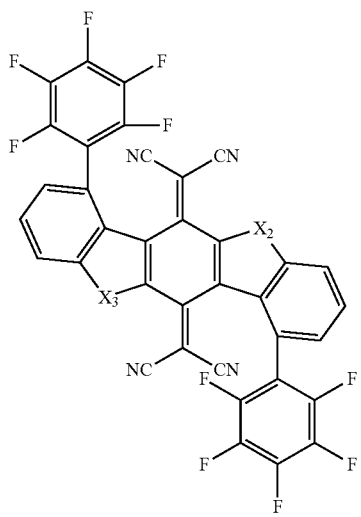
$X_3 = X_2 = O$ compound BO-91
$X_3 = X_2 = S$ compound BS-91
$X_3 = X_2 = Se$ compound BSe-91

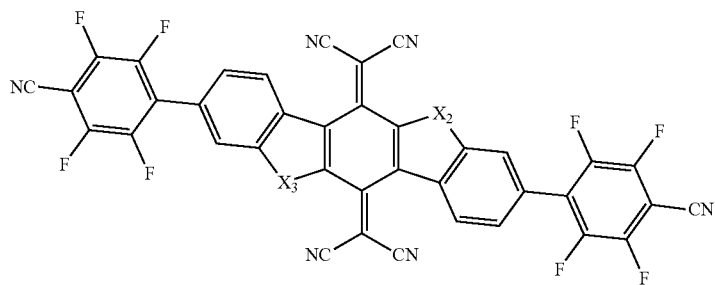
X₃ = X₂ = O compound BO-92
X₃ = X₂ = S compound BS-92
X₃ = X₂ = Se compound BSe-92
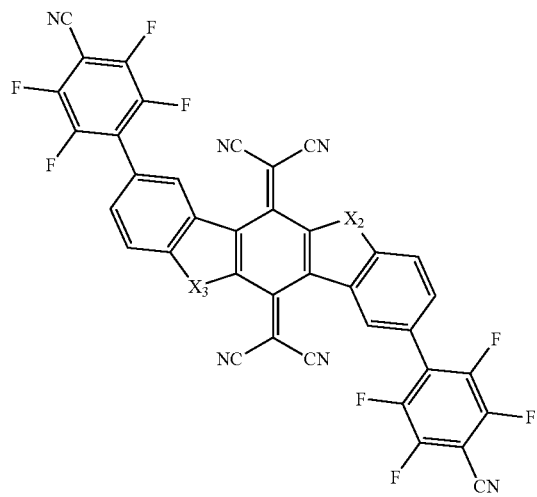
X₃ = X₂ = O compound BO-93
X₃ = X₂ = S compound BS-93
X₃ = X₂ = Se compound BSe-93
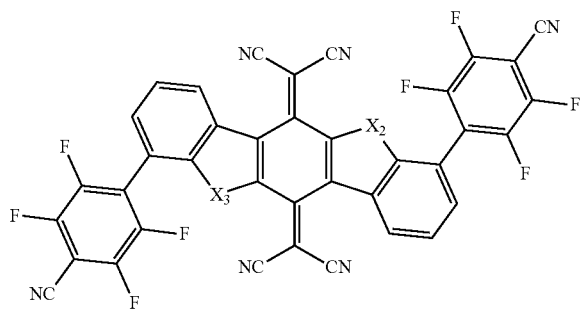
X₃ = X₂ = O compound BO-94
X₃ = X₂ = S compound BS-94
X₃ = X₂ = Se compound BSe-94

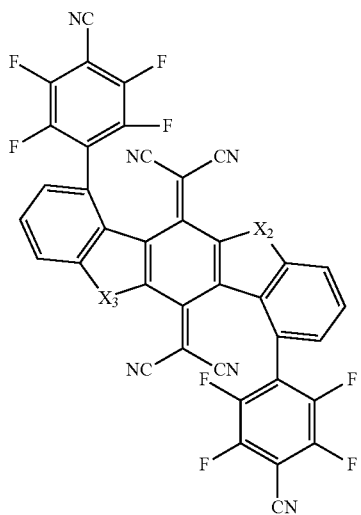
X$_3$ = X$_2$ = O compound BO-95
X$_3$ = X$_2$ = S compound BS-95
X$_3$ = X$_2$ = Se compound BSe-95
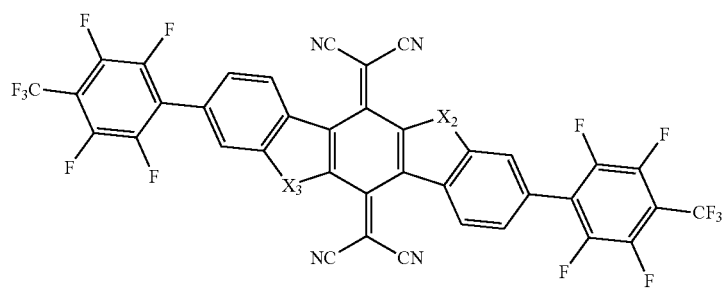
X$_3$ = X$_2$ = O compound BO-96
X$_3$ = X$_2$ = S compound BS-96
X$_3$ = X$_2$ = Se compound BSe-96
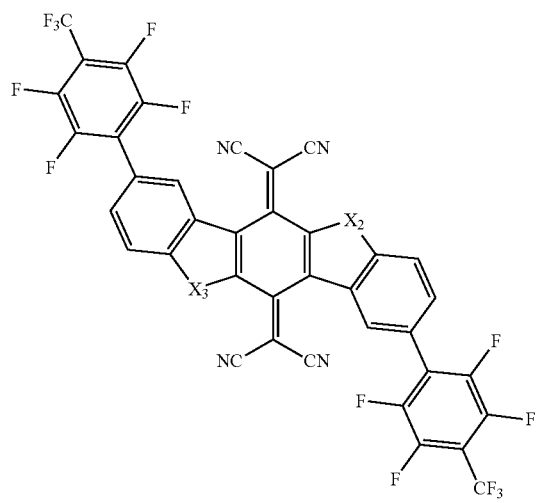
X$_3$ = X$_2$ = O compound BO-97
X$_3$ = X$_2$ = S compound BS-97
X$_3$ = X$_2$ = Se compound BSe-97

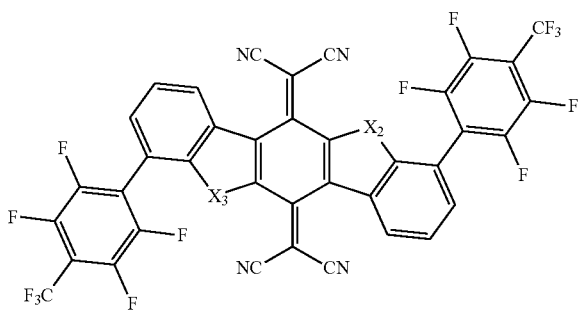
$X_3 = X_2 = O$ compound BO-98
$X_3 = X_2 = S$ compound BS-98
$X_3 = X_2 = Se$ compound BSe-98
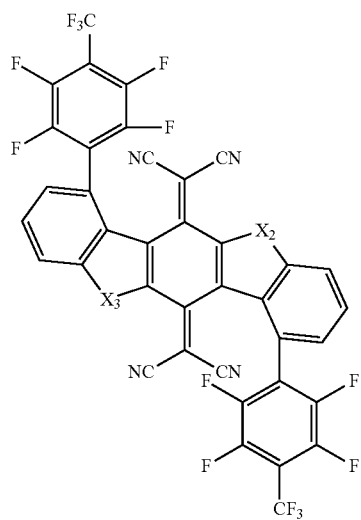
$X_3 = X_2 = O$ compound BO-99
$X_3 = X_2 = S$ compound BS-99
$X_3 = X_2 = Se$ compound BSe-99
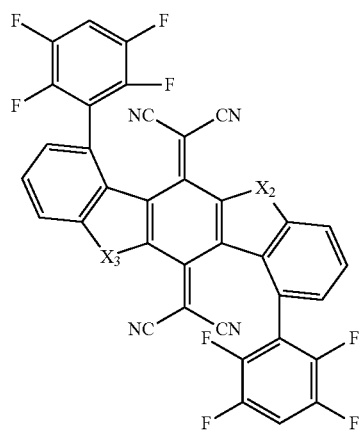
$X_3 = X_2 = O$ compound BO-100
$X_3 = X_2 = S$ compound BS-100
$X_3 = X_2 = Se$ compound BSe-100

-continued
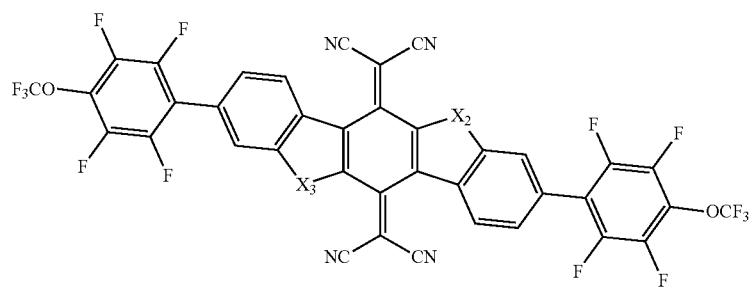
X₃ = X₂ = O compound BO-101
X₃ = X₂ = S compound BS-101
X₃ = X₂ = Se compound BSe-101
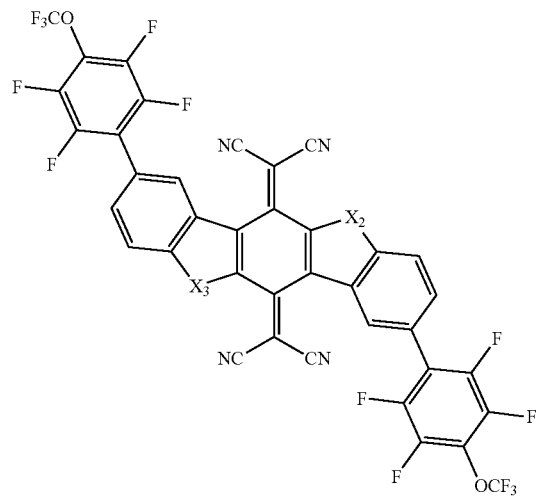
X₃ = X₂ = O compound BO-102
X₃ = X₂ = S compound BS-102
X₃ = X₂ = Se compound BSe-102
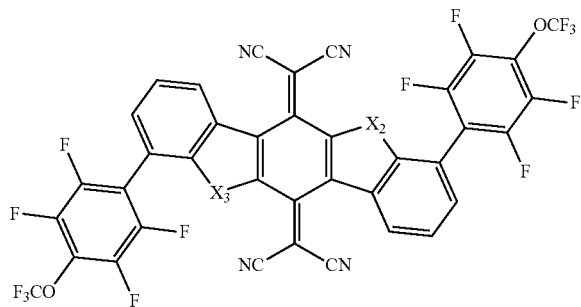
X₃ = X₂ = O compound BO-103
X₃ = X₂ = S compound BS-103
X₃ = X₂ = Se compound BSe-103

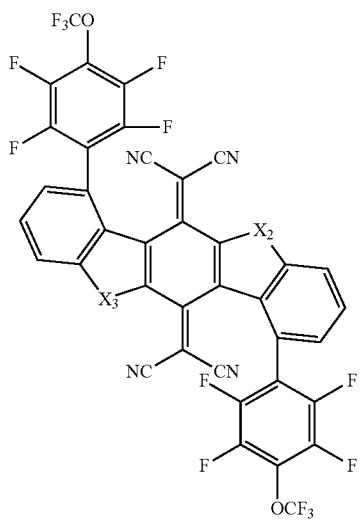
$X_3 = X_2 = O$ compound BO-104
$X_3 = X_2 = S$ compound BS-104
$X_3 = X_2 = Se$ compound BSe-104
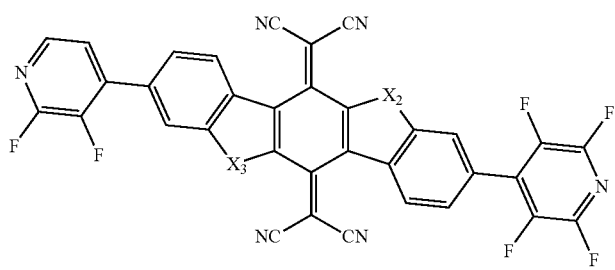
$X_3 = X_2 = O$ compound BO-105
$X_3 = X_2 = S$ compound BS-105
$X_3 = X_2 = Se$ compound BSe-105
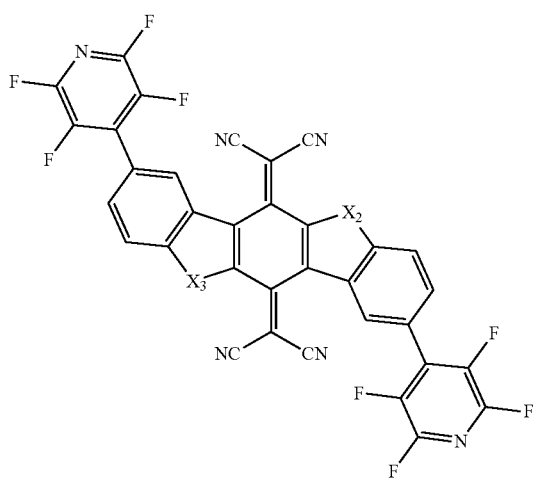
$X_3 = X_2 = O$ compound BO-106
$X_3 = X_2 = S$ compound BS-106
$X_3 = X_2 = Se$ compound BSe-106

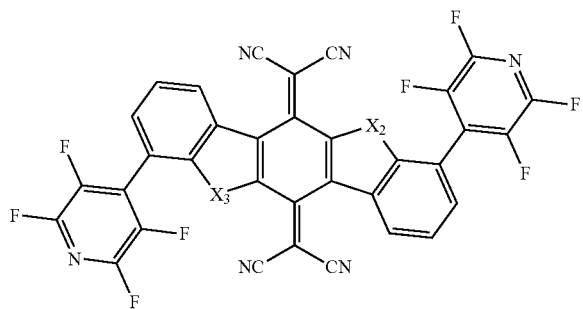
X₃ = X₂ = O compound BO-107
X₃ = X₂ = S compound BS-107
X₃ = X₂ = Se compound BSe-107
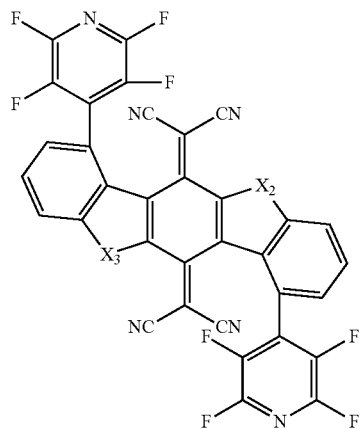
X₃ = X₂ = O compound BO-108
X₃ = X₂ = S compound BS-108
X₃ = X₂ = Se compound BSe-108
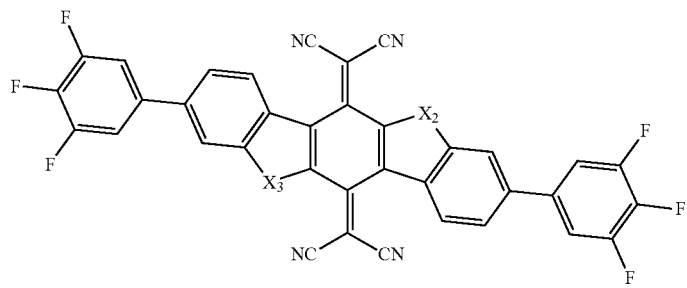
X₃ = X₂ = O compound BO-109
X₃ = X₂ = S compound BS-109
X₃ = X₂ = Se compound BSe-109

-continued
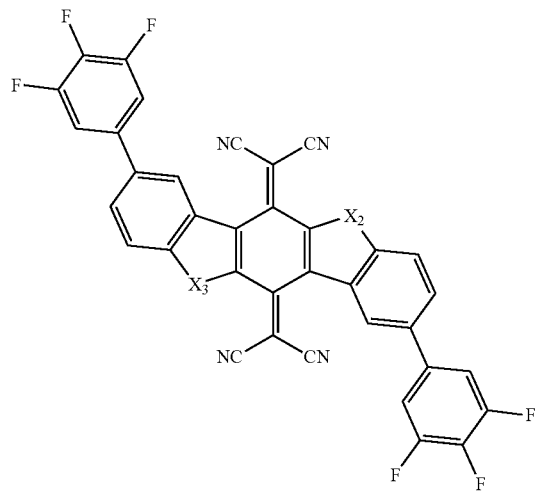
X₃ = X₂ = O compound BO-110
X₃ = X₂ = S compound BS-110
X₃ = X₂ = Se compound BSe-110
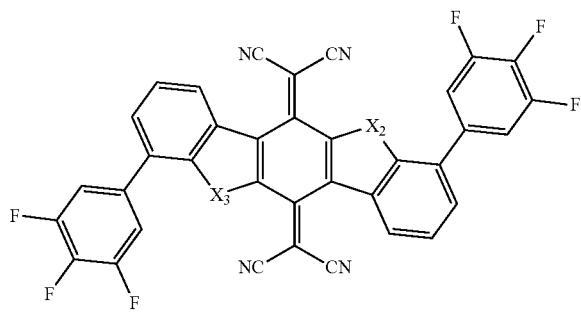
X₃ = X₂ = O compound BO-111
X₃ = X₂ = S compound BS-111
X₃ = X₂ = Se compound BSe-111
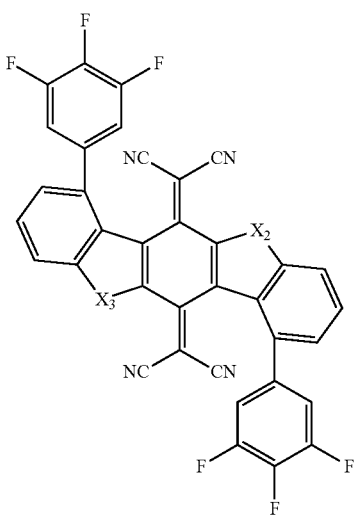
X₃ = X₂ = O compound BO-112
X₃ = X₂ = S compound BS-112
X₃ = X₂ = Se compound BSe-112

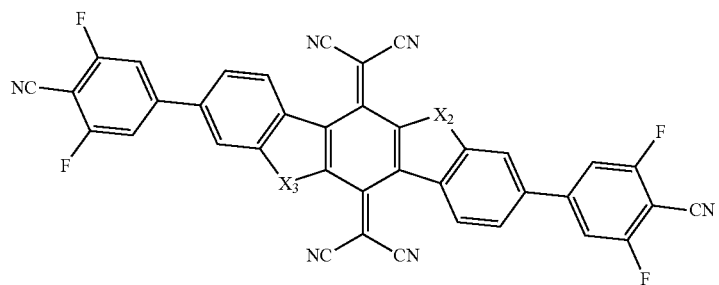
X₃ = X₂ = O compound BO-113
X₃ = X₂ = S compound BS-113
X₃ = X₂ = Se compound BSe-113
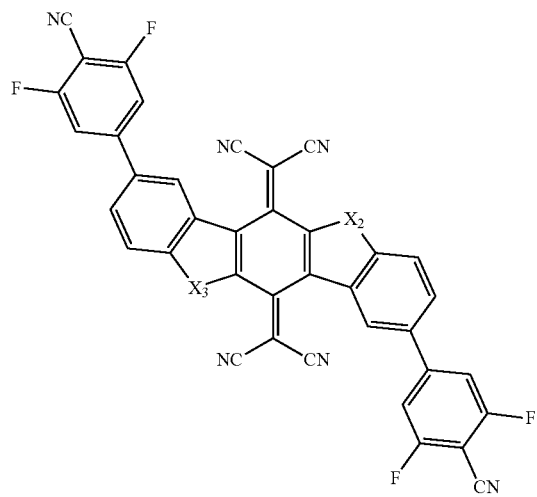
X₃ = X₂ = O compound BO-114
X₃ = X₂ = S compound BS-114
X₃ = X₂ = Se compound BSe-114
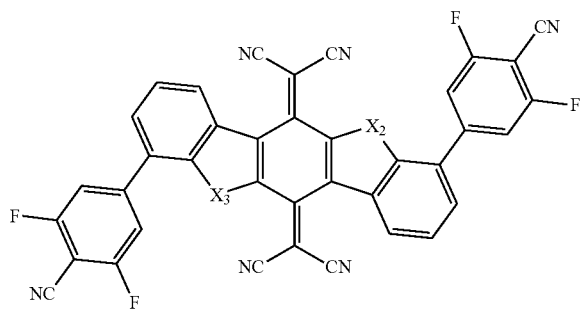
X₃ = X₂ = O compound BO-115
X₃ = X₂ = S compound BS-115
X₃ = X₂ = Se compound BSe-115

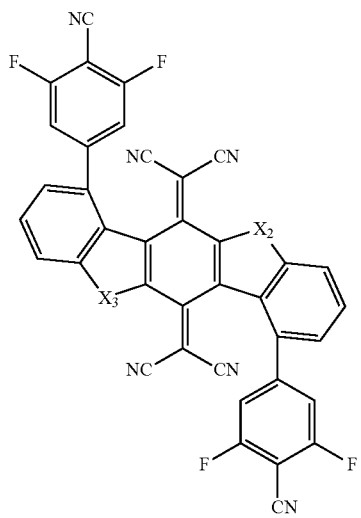
X₃ = X₂ = O compound BO-116
X₃ = X₂ = S compound BS-116
X₃ = X₂ = Se compound BSe-116
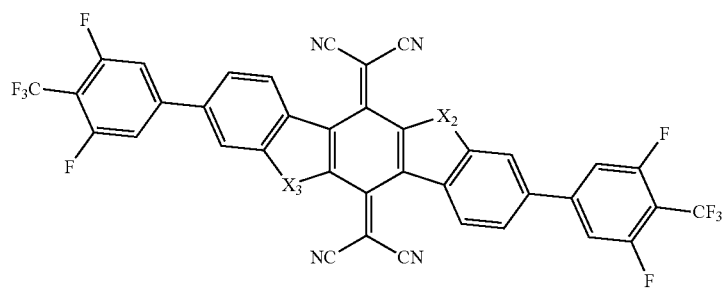
X₃ = X₂ = O compound BO-117
X₃ = X₂ = S compound BS-117
X₃ = X₂ = Se compound BSe-117
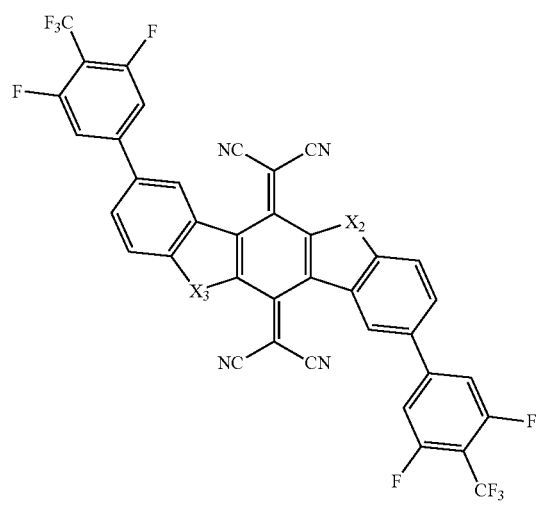
X₃ = X₂ = O compound BO-118
X₃ = X₂ = S compound BS-118
X₃ = X₂ = Se compound BSe-118

-continued
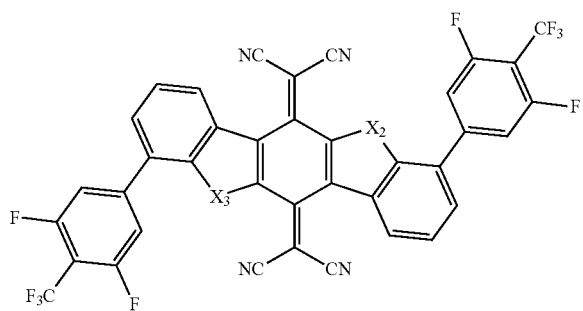
X₃ = X₂ = O compound BO-119
X₃ = X₂ = S compound BS-119
X₃ = X₂ = Se compound BSe-119
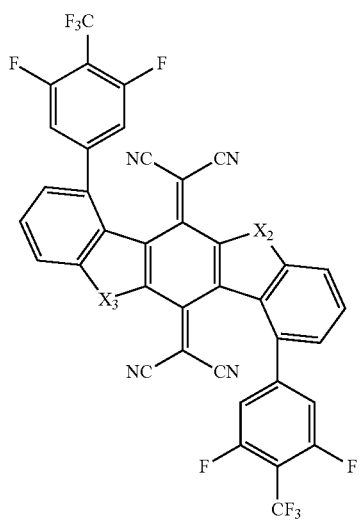
X₃ = X₂ = O compound BO-120
X₃ = X₂ = S compound BS-120
X₃ = X₂ = Se compound BSe-120
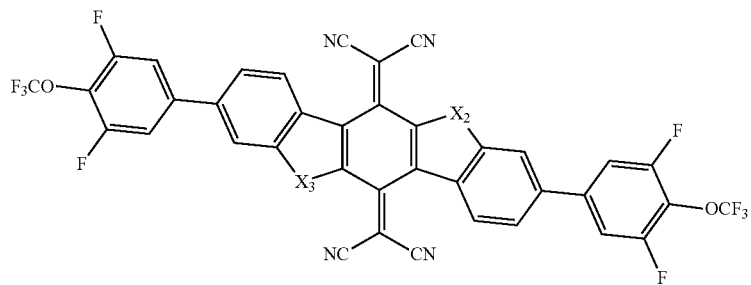
X₃ = X₂ = O compound BO-121
X₃ = X₂ = S compound BS-121
X₃ = X₂ = Se compound BSe-121

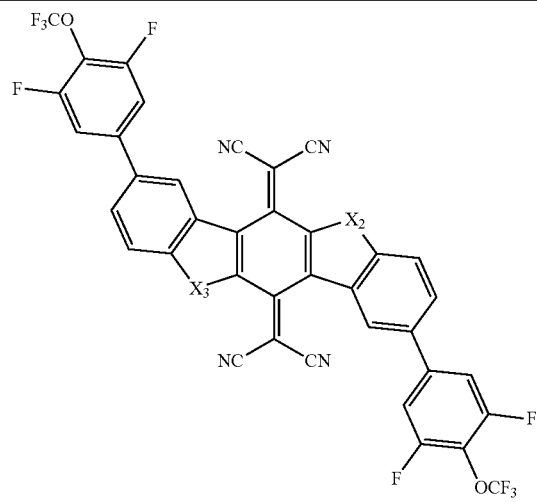
X$_3$ = X$_2$ = O compound BO-122
X$_3$ = X$_2$ = S compound BS-122
X$_3$ = X$_2$ = Se compound BSe-122
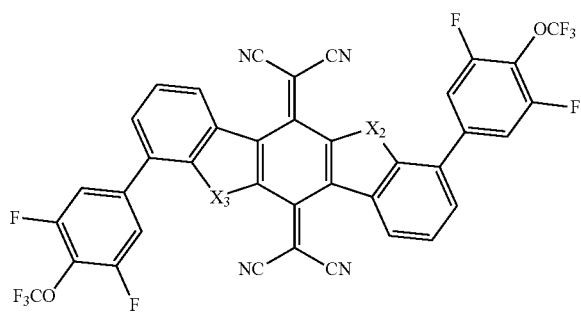
X$_3$ = X$_2$ = O compound BO-123
X$_3$ = X$_2$ = S compound BS-123
X$_3$ = X$_2$ = Se compound BSe-123
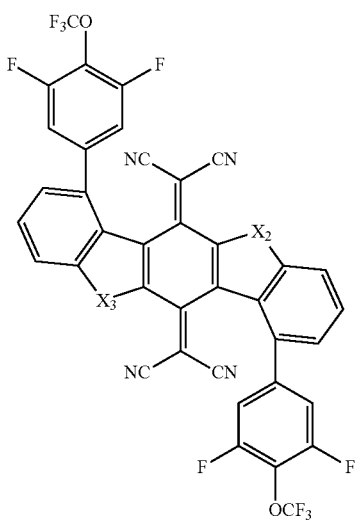
X$_3$ = X$_2$ = O compound BO-124
X$_3$ = X$_2$ = S compound BS-124
X$_3$ = X$_2$ = Se compound BSe-124

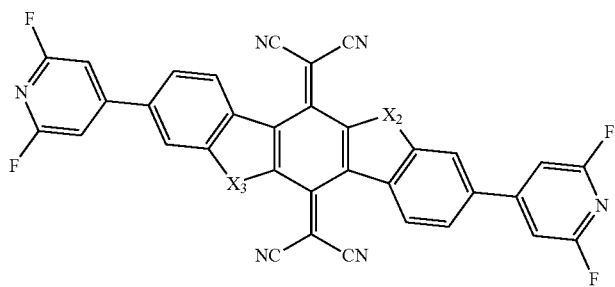
X₃ = X₂ = O compound BO-125
X₃ = X₂ = S compound BS-125
X₃ = X₂ = Se compound BSe-125
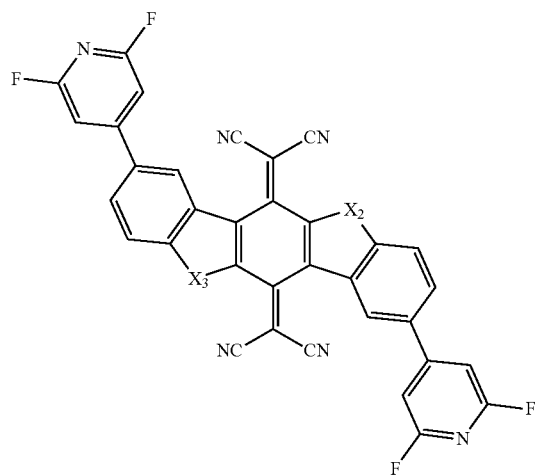
X₃ = X₂ = O compound BO-126
X₃ = X₂ = S compound BS-126
X₃ = X₂ = Se compound BSe-126
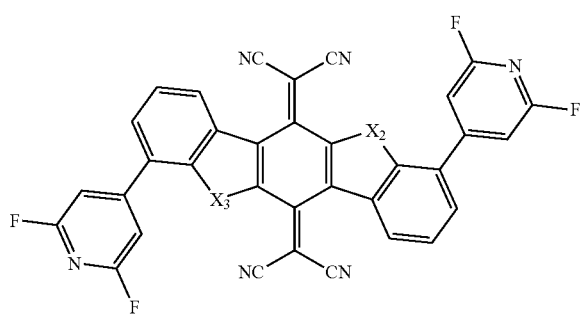
X₃ = X₂ = O compound BO-127
X₃ = X₂ = S compound BS-127
X₃ = X₂ = Se compound BSe-127

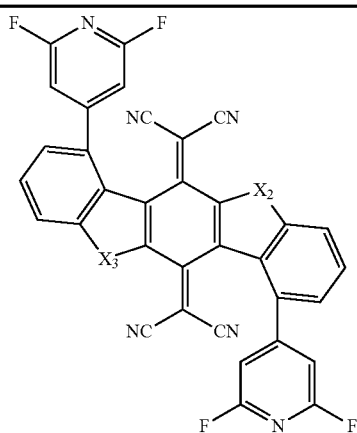
X₃ = X₂ = O compound BO-128
X₃ = X₂ = S compound BS-128
X₃ = X₂ = Se compound BSe-128
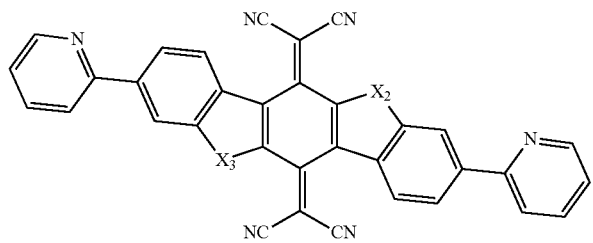
X₃ = X₂ = O compound BO-129
X₃ = X₂ = S compound BS-129
X₃ = X₂ = Se compound BSe-129
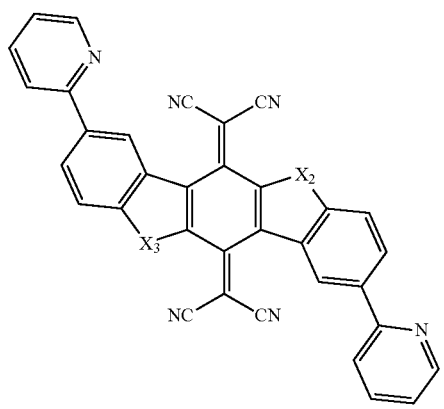
X₃ = X₂ = O compound BO-130
X₃ = X₂ = S compound BS-130
X₃ = X₂ = Se compound BSe-130
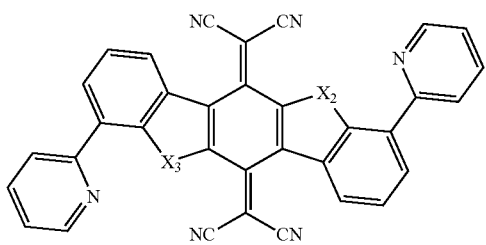
X₃ = X₂ = O compound BO-131
X₃ = X₂ = S compound BS-131
X₃ = X₂ = Se compound BSe-131

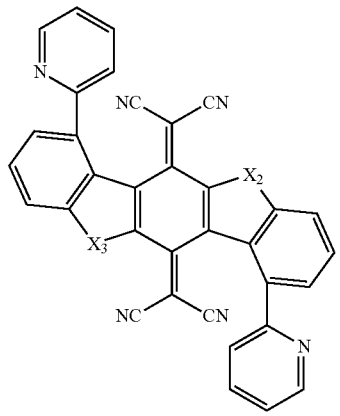
X$_1$ = X$_2$ = O compound BO-132
X$_1$ = X$_2$ = S compound BS-132
X$_1$ = X$_2$ = Se compound BSe-132
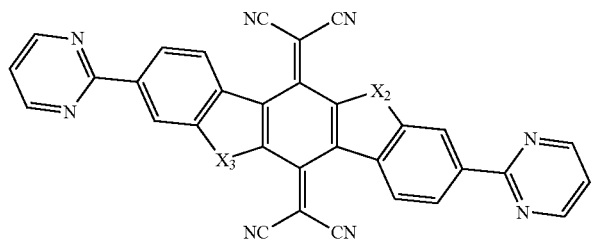
X$_3$ = X$_2$ = O compound BO-133
X$_3$ = X$_2$ = S compound BS-133
X$_3$ = X$_2$ = Se compound BSe-133
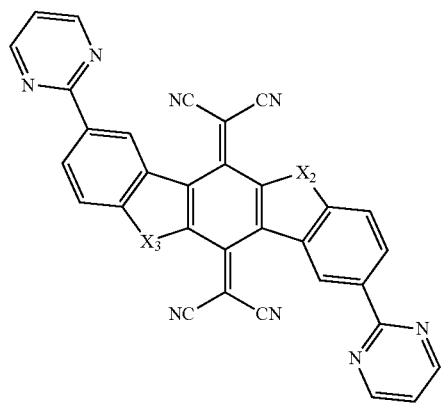
X$_3$ = X$_2$ = O compound BO-134
X$_3$ = X$_2$ = S compound BS-134
X$_3$ = X$_2$ = Se compound BSe-134
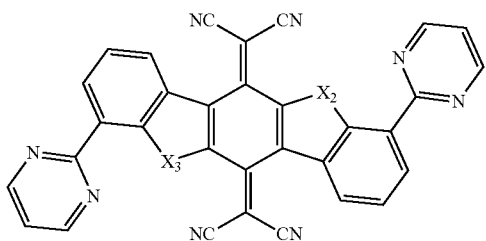

$X_3 = X_2 = O$ compound BO-135
$X_3 = X_2 = S$ compound BS-135
$X_3 = X_2 = Se$ compound BSe-135
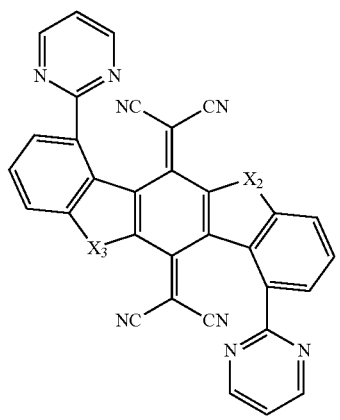
$X_3 = X_2 = O$ compound BO-136
$X_3 = X_2 = S$ compound BS-136
$X_3 = X_2 = Se$ compound BSe-136
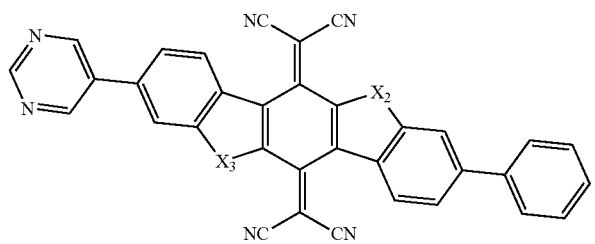
$X_3 = X_2 = O$ compound BO-137
$X_3 = X_2 = S$ compound BS-137
$X_3 = X_2 = Se$ compound BSe-137
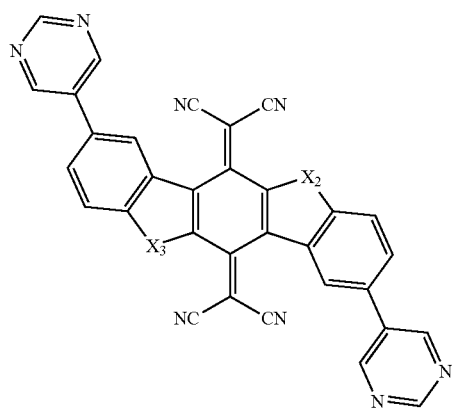
$X_3 = X_2 = O$ compound BO-138
$X_3 = X_2 = S$ compound BS-138
$X_3 = X_2 = Se$ compound BSe-138

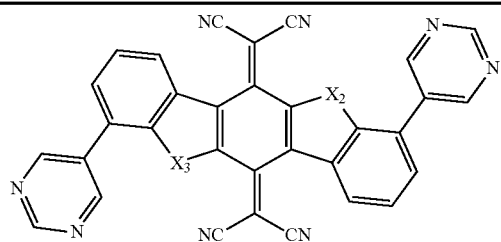
X₃ = X₂ = O compound BO-139
X₃ = X₂ = S compound BS-139
X₃ = X₂ = Se compound BSe-139
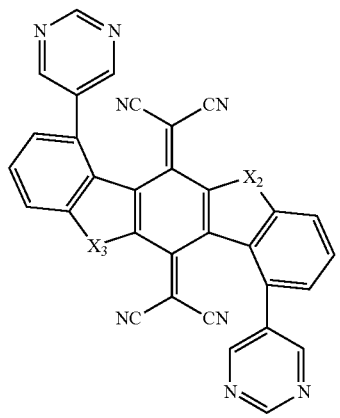
X₁ = X₂ = O compound BO-140
X₁ = X₂ = S compound BS-140
X₁ = X₂ = Se compound BSe-140
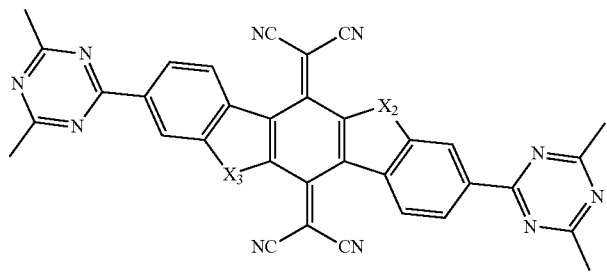
X₃ = X₂ = O compound BO-141
X₃ = X₂ = S compound BS-141
X₃ = X₂ = Se compound BSe-141
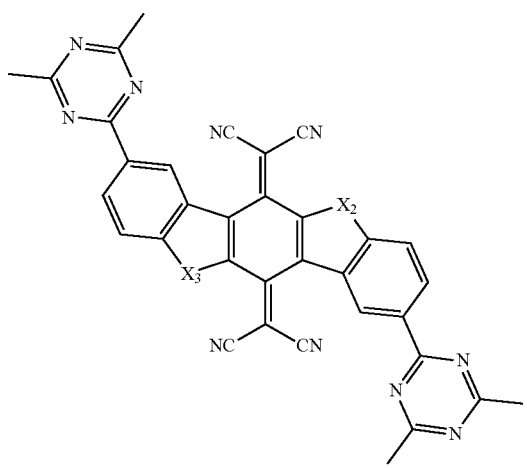

X₃ = X₂ = O compound BO-142
X₃ = X₂ = S compound BS-142
X₃ = X₂ = Se compound BSe-142
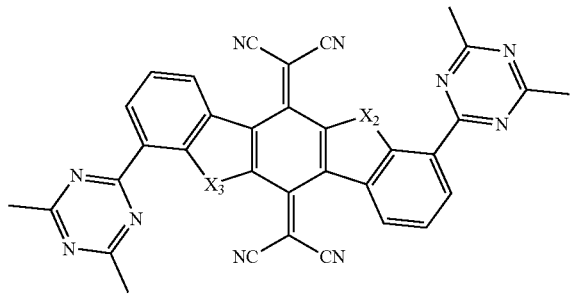
X₃ = X₂ = O compound BO-143
X₃ = X₂ = S compound BS-143
X₃ = X₂ = Se compound BSe-143
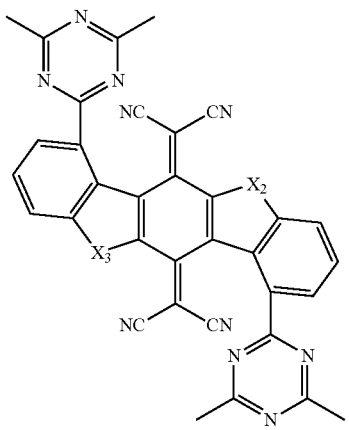
X₃ = X₂ = O compound BO-144
X₃ = X₂ = S compound BS-144
X₃ = X₂ = Se compound BSe-144
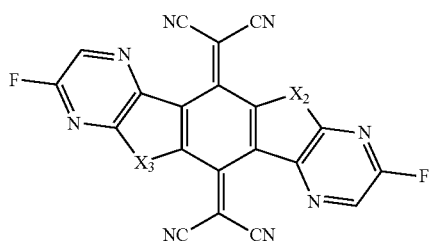
X₃ = X₂ = O compound BO-145
X₃ = X₂ = S compound BS-145
X₃ = X₂ = Se compound BSe-145
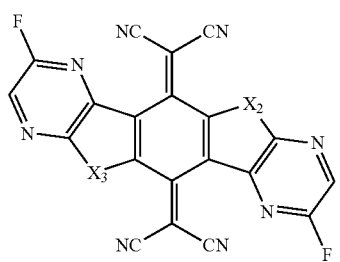

$X_3 = X_2 = $ O compound BO-146
$X_3 = X_2 = $ S compound BS-146
$X_3 = X_2 = $ Se compound BSe-146
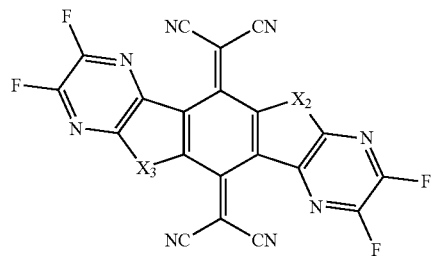
$X_3 = X_2 = $ O compound BO-147
$X_3 = X_2 = $ S compound BS-147
$X_3 = X_2 = $ Se compound BSe-147
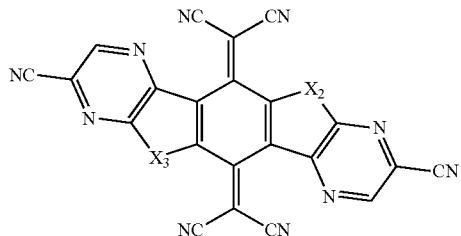
$X_3 = X_2 = $ O compound BO-148
$X_3 = X_2 = $ S compound BS-148
$X_3 = X_2 = $ Se compound BSe-148
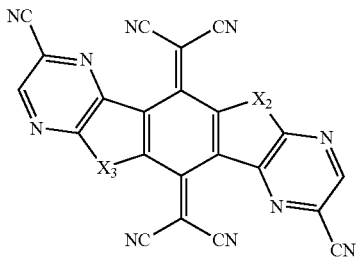
$X_3 = X_2 = $ O compound BO-149
$X_3 = X_2 = $ S compound BS-149
$X_3 = X_2 = $ Se compound BSe-149
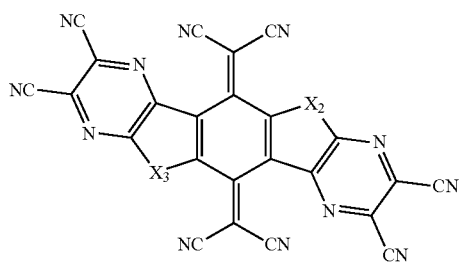
$X_3 = X_2 = $ O compound BO-150
$X_3 = X_2 = $ S compound BS-150
$X_3 = X_2 = $ Se compound BSe-150

-continued
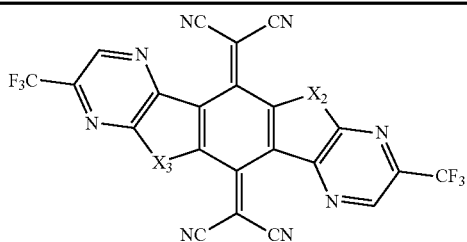
X₃ = X₂ = O compound BO-151
X₃ = X₂ = S compound BS-151
X₃ = X₂ = Se compound BSe-151
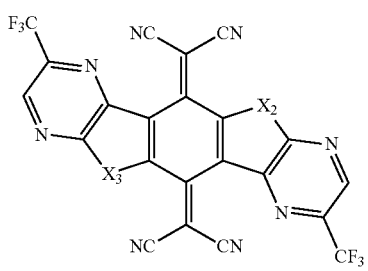
X₃ = X₂ = O compound BO-152
X₃ = X₂ = S compound BS-152
X₃ = X₂ = Se compound BSe-152
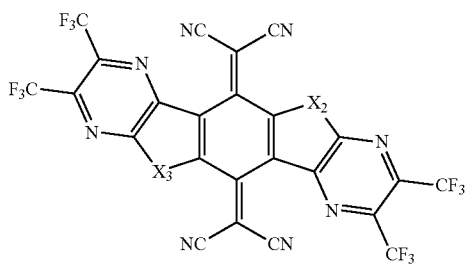
X₃ = X₂ = O compound BO-153
X₃ = X₂ = S compound BS-153
X₃ = X₂ = Se compound BSe-153
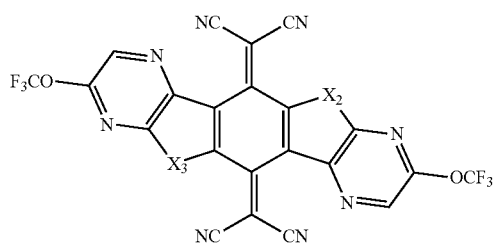
X₃ = X₂ = O compound BO-154
X₃ = X₂ = S compound BS-154
X₃ = X₂ = Se compound BSe-154
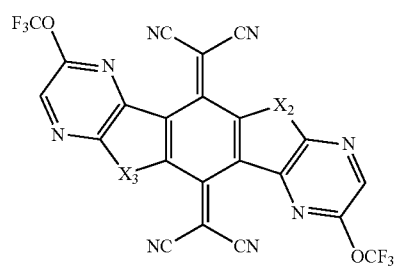

X₃ = X₂ = O compound BO-155
X₃ = X₂ = S compound BS-155
X₃ = X₂ = Se compound BSe-155
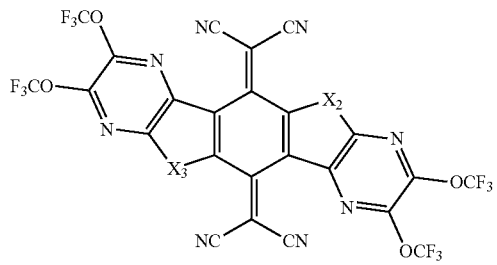
X₃ = X₂ = O compound BO-156
X₃ = X₂ = S compound BS-156
X₃ = X₂ = Se compound BSe-156
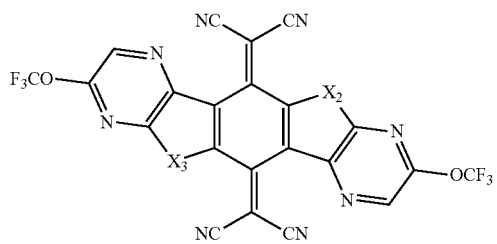
X₃ = X₂ = O compound BO-157
X₃ = X₂ = S compound BS-157
X₃ = X₂ = Se compound BSe-157
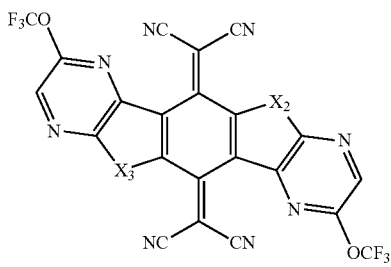
X₃ = X₂ = O compound BO-158
X₃ = X₂ = S compound BS-158
X₃ = X₂ = Se compound BSe-158
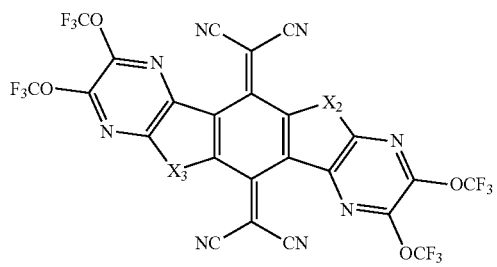
X₃ = X₂ = O compound BO-159
X₃ = X₂ = S compound BS-159
X₃ = X₂ = Se compound BSe-159

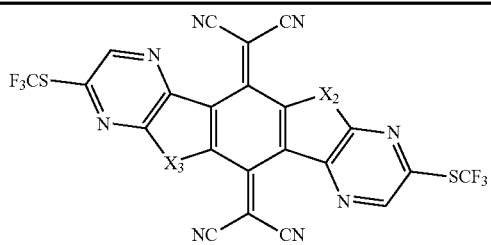
X₃ = X₂ = O compound BO-160
X₃ = X₂ = S compound BS-160
X₃ = X₂ = Se compound BSe-160
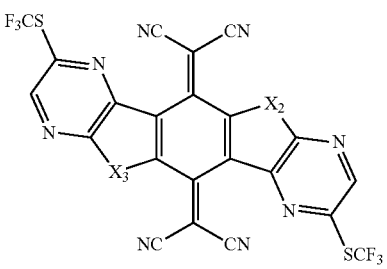
X₃ = X₂ = O compound BO-161
X₃ = X₂ = S compound BS-161
X₃ = X₂ = Se compound BSe-161
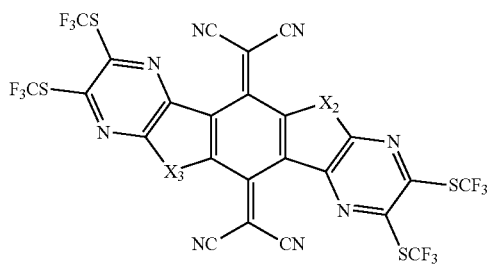
X₃ = X₂ = O compound BO-162
X₃ = X₂ = S compound BS-162
X₃ = X₂ = Se compound BSe-162
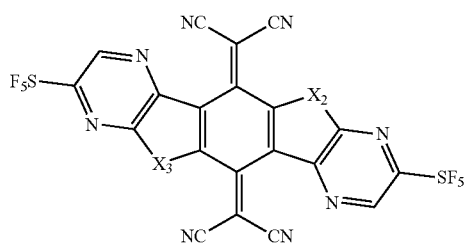
X₃ = X₂ = O compound BO-163
X₃ = X₂ = S compound BS-163
X₃ = X₂ = Se compound BSe-163
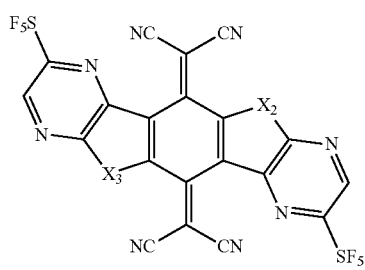

X₃ = X₂ = O compound BO-164
X₃ = X₂ = S compound BS-164
X₃ = X₂ = Se compound BSe-164
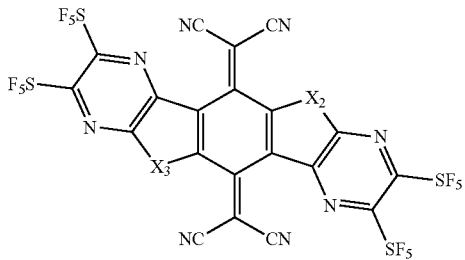
X₃ = X₂ = O compound BO-165
X₃ = X₂ = S compound BS-165
X₃ = X₂ = Se compound BSe-165
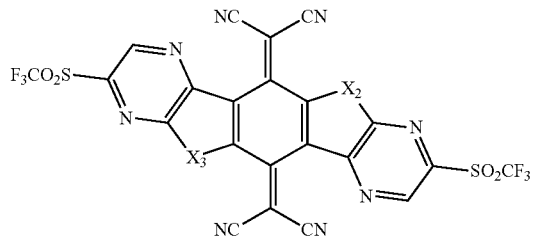
X₃ = X₂ = O compound BO-166
X₃ = X₂ = S compound BS-166
X₃ = X₂ = Se compound BSe-166
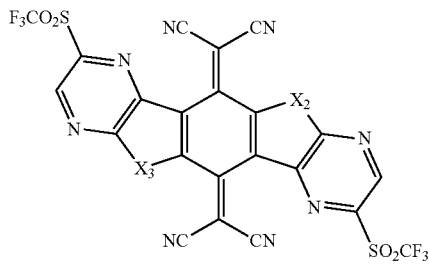
X₃ = X₂ = O compound BO-167
X₃ = X₂ = S compound BS-167
X₃ = X₂ = Se compound BSe-167
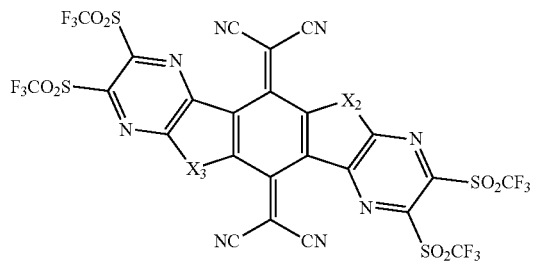
X₃ = X₂ = O compound BO-168
X₃ = X₂ = S compound BS-168
X₃ = X₂ = Se compound BSe-168

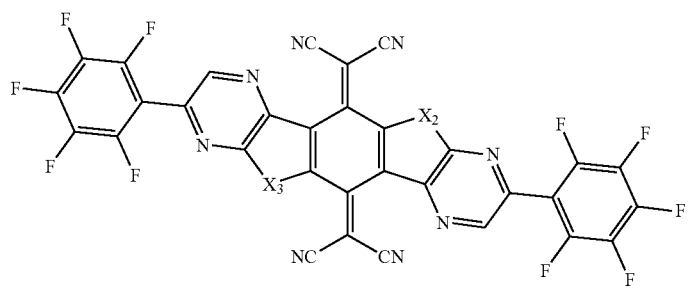
X₃ = X₂ = O compound BO-169
X₃ = X₂ = S compound BS-169
X₃ = X₂ = Se compound BSe-169
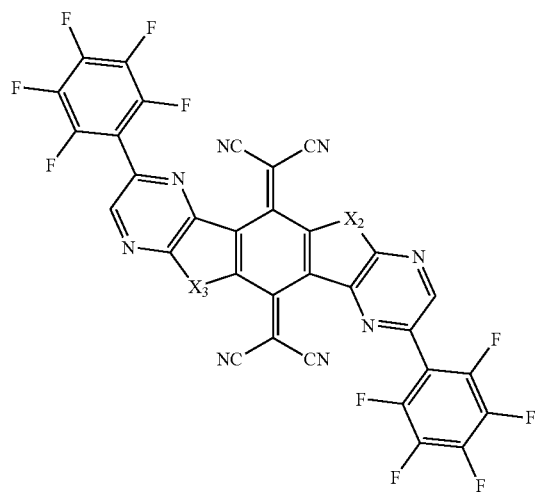
X₃ = X₂ = O compound BO-170
X₃ = X₂ = S compound BS-170
X₃ = X₂ = Se compound BSe-170
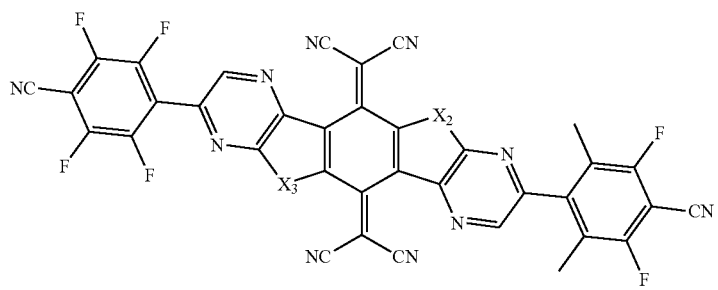
X₃ = X₂ = O compound BO-171
X₃ = X₂ = S compound BS-171
X₃ = X₂ = Se compound BSe-171

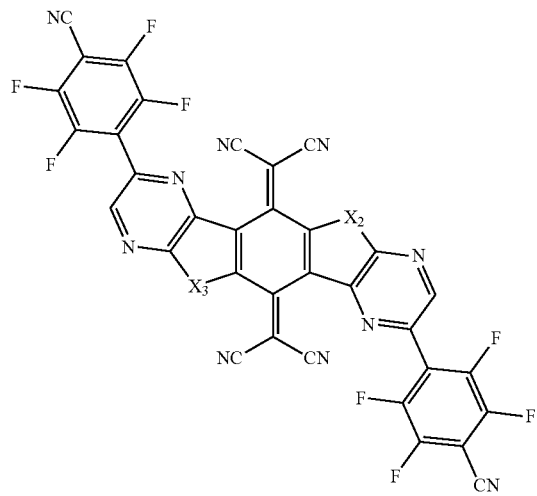
X₃ = X₂ = O compound BO-172
X₃ = X₂ = S compound BS-172
X₃ = X₂ = Se compound BSe-172
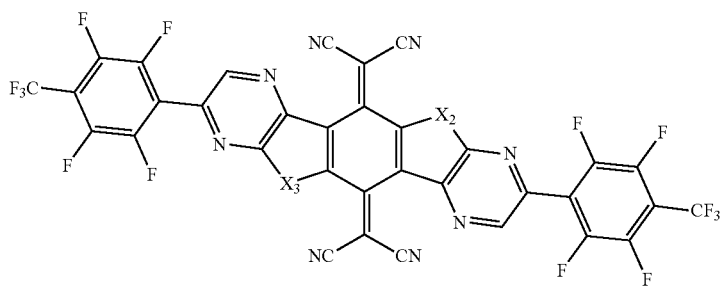
X₃ = X₂ = O compound BO-173
X₃ = X₂ = S compound BS-173
X₃ = X₂ = Se compound BSe-173
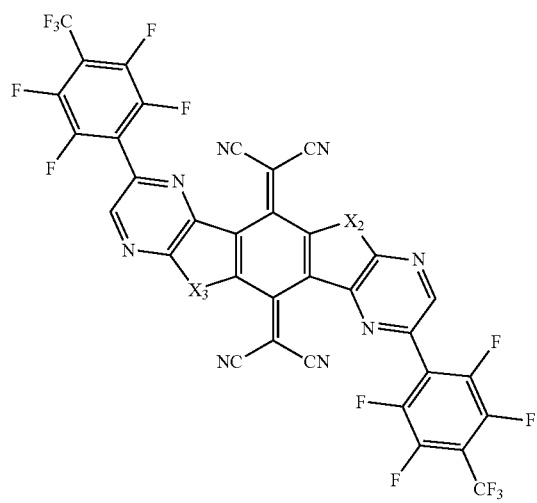
X₃ = X₂ = O compound BO-174
X₃ = X₂ = S compound BS-174
X₃ = X₂ = Se compound BSe-174

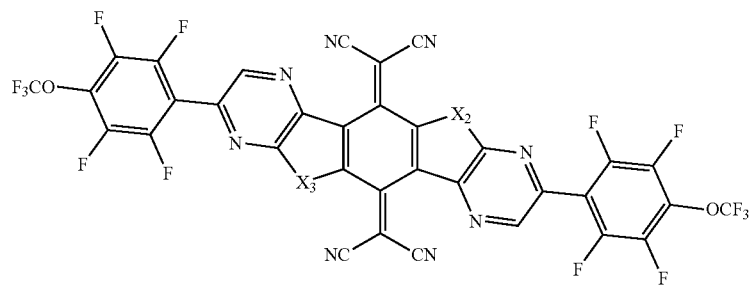
X₃ = X₂ = O compound BO-175
X₃ = X₂ = S compound BS-175
X₃ = X₂ = Se compound BSe-175
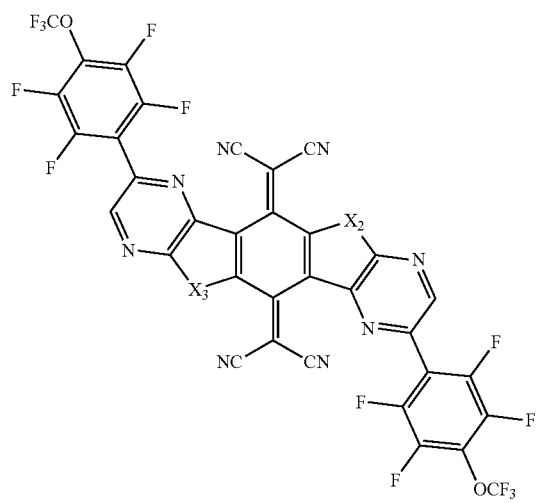
X₃ = X₂ = O compound BO-176
X₃ = X₂ = S compound BS-176
X₃ = X₂ = Se compound BSe-176
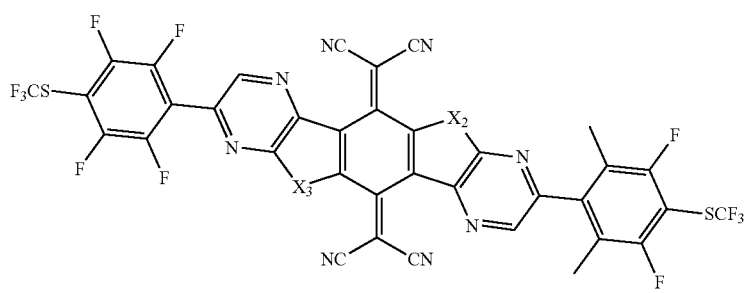
X₃ = X₂ = O compound BO-177
X₃ = X₂ = S compound BS-177
X₃ = X₂ = Se compound BSe-177

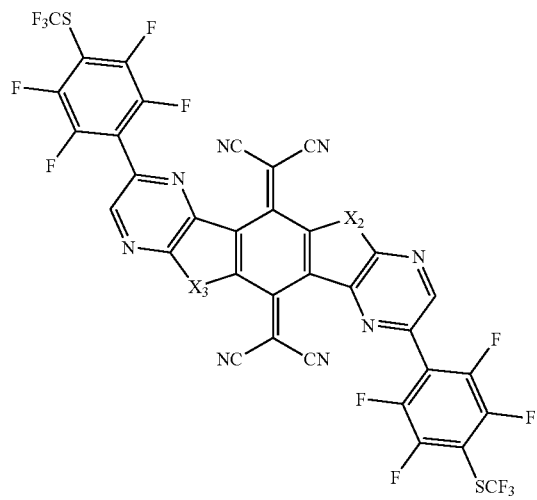
$X_3 = X_2 = O$ compound BO-178
$X_3 = X_2 = S$ compound BS-178
$X_3 = X_2 = Se$ compound BSe-178
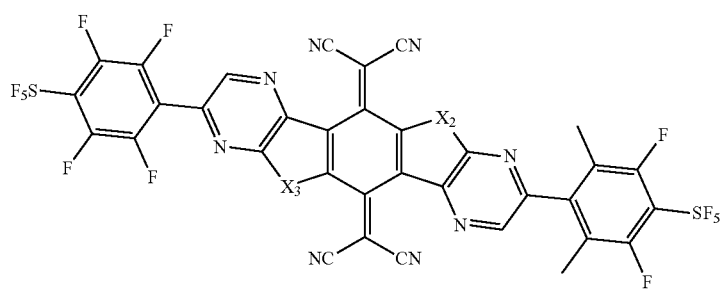
$X_3 = X_2 = O$ compound BO-179
$X_3 = X_2 = S$ compound BS-179
$X_3 = X_2 = Se$ compound BSe-179
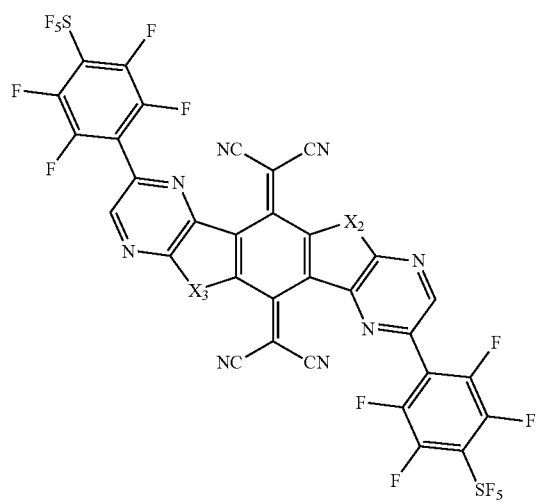
$X_3 = X_2 = O$ compound BO-180
$X_3 = X_2 = S$ compound BS-180
$X_3 = X_2 = Se$ compound BSe-180

-continued
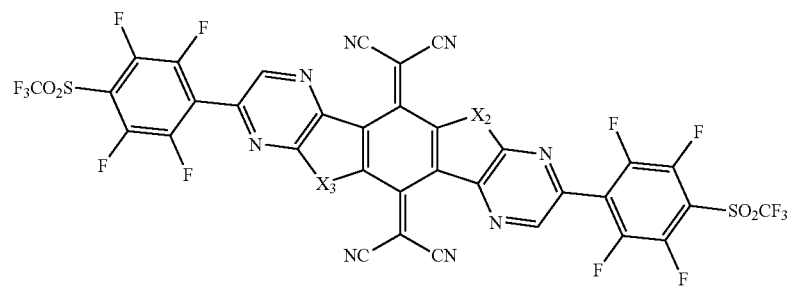
X₃ = X₂ = O compound BO-181
X₃ = X₂ = S compound BS-181
X₃ = X₂ = Se compound BSe-181
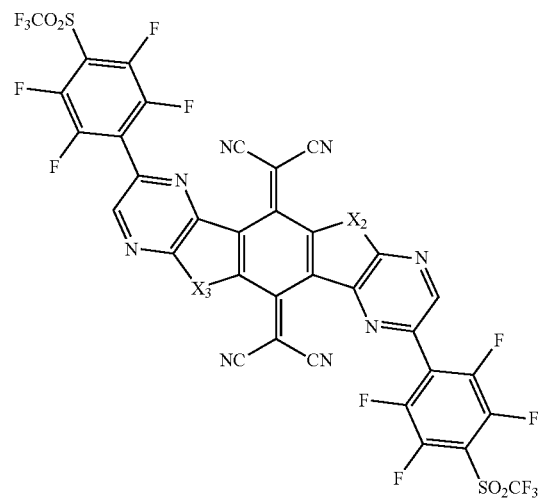
X₃ = X₂ = O compound BO-182
X₃ = X₂ = S compound BS-182
X₃ = X₂ = Se compound BSe-182
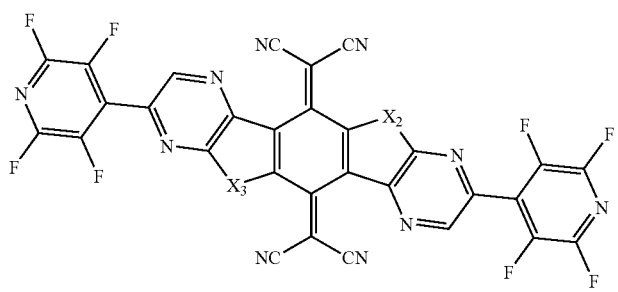
X₃ = X₂ = O compound BO-183
X₃ = X₂ = S compound BS-183
X₃ = X₂ = Se compound BSe-183

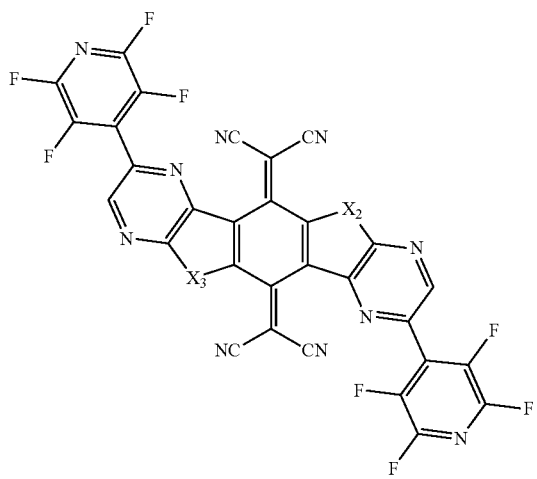
X₃ = X₂ = O compound BO-184
X₃ = X₂ = S compound BS-184
X₃ = X₂ = Se compound BSe-184
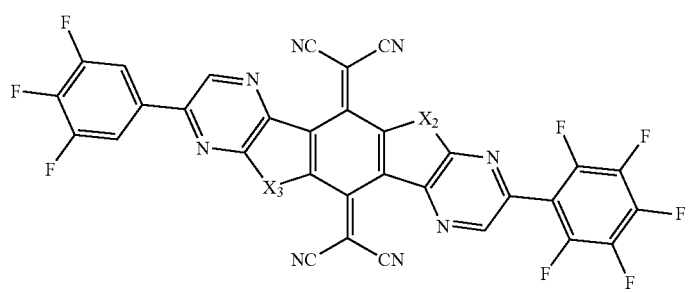
X₃ = X₂ = O compound BO-185
X₃ = X₂ = S compound BS-185
X₃ = X₂ = Se compound BSe-185
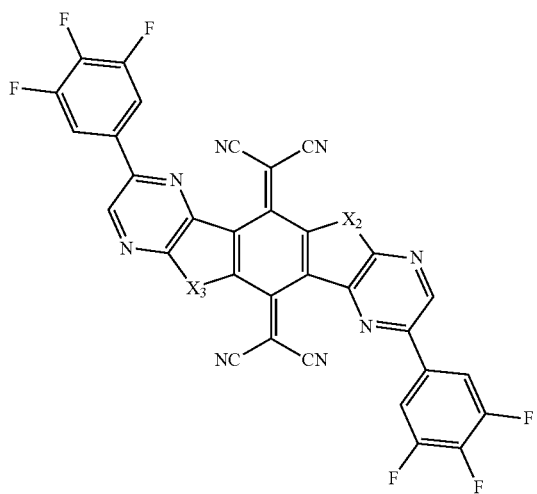
X₃ = X₂ = O compound BO-186
X₃ = X₂ = S compound BS-186
X₃ = X₂ = Se compound BSe-186

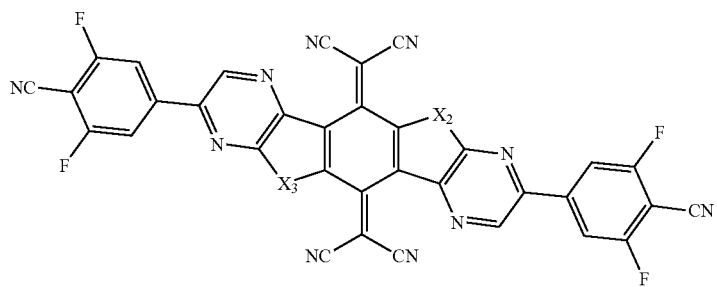
X$_3$ = X$_2$ = O compound BO-187
X$_3$ = X$_2$ = S compound BS-187
X$_3$ = X$_2$ = Se compound BSe-187
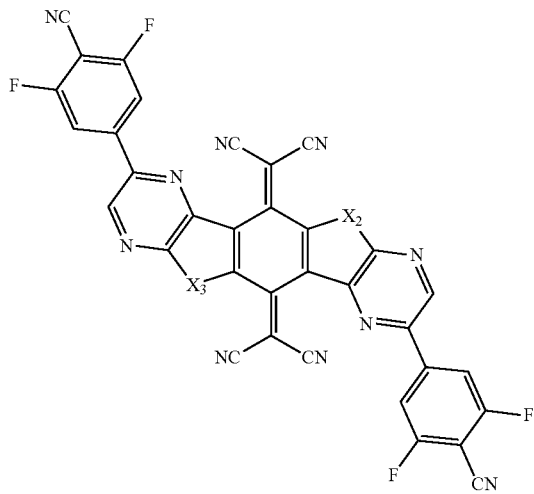
X$_3$ = X$_2$ = O compound BO-188
X$_3$ = X$_2$ = S compound BS-188
X$_3$ = X$_2$ = Se compound BSe-188
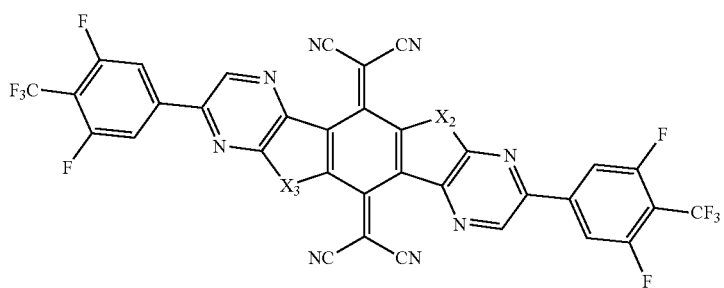
X$_3$ = X$_2$ = O compound BO-189
X$_3$ = X$_2$ = S compound BS-189
X$_3$ = X$_2$ = Se compound BSe-189

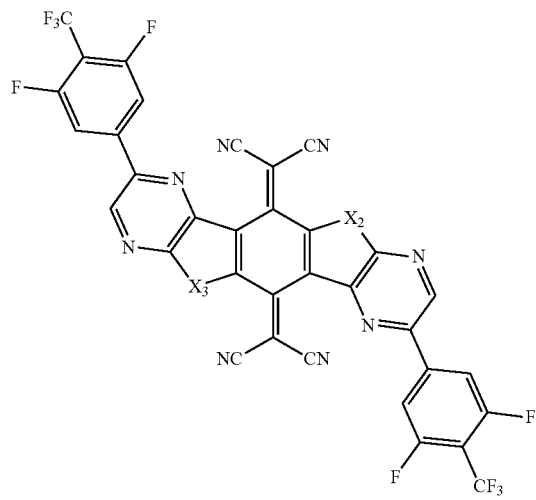
X₃ = X₂ = O compound BO-190
X₃ = X₂ = S compound BS-190
X₃ = X₂ = Se compound BSe-190
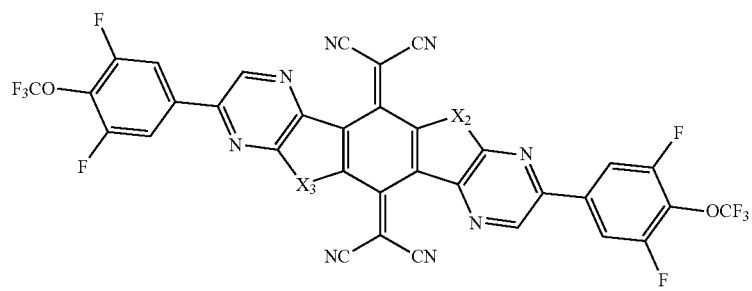
X₃ = X₂ = O compound BO-191
X₃ = X₂ = S compound BS-191
X₃ = X₂ = Se compound BSe-191
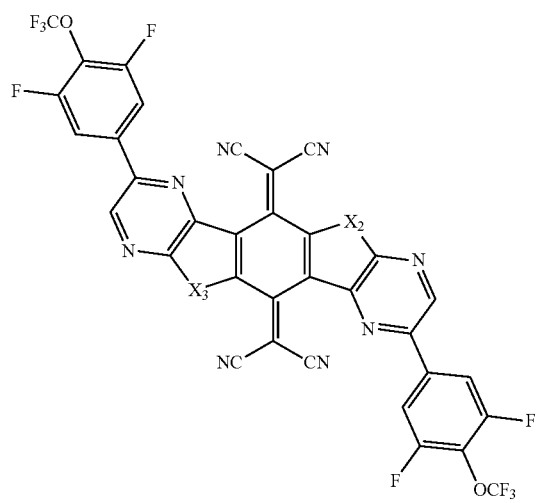
X₃ = X₂ = O compound BO-192
X₃ = X₂ = S compound BS-192
X₃ = X₂ = Se compound BSe-192

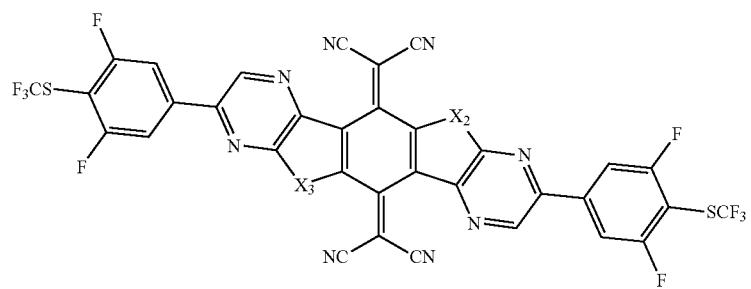
X₃ = X₂ = O compound BO-193
X₃ = X₂ = S compound BS-193
X₃ = X₂ = Se compound BSe-193
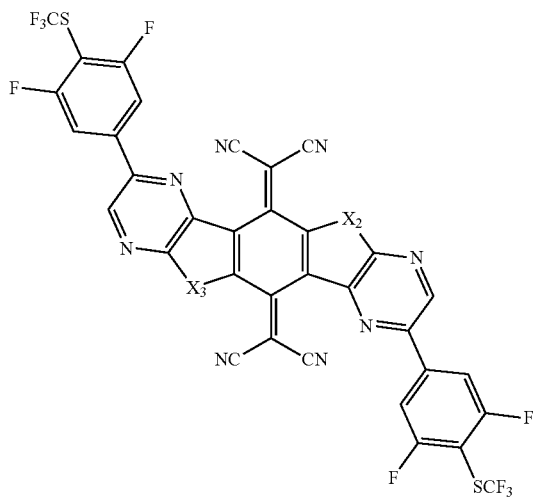
X₃ = X₂ = O compound BO-194
X₃ = X₂ = S compound BS-194
X₃ = X₂ = Se compound BSe-194
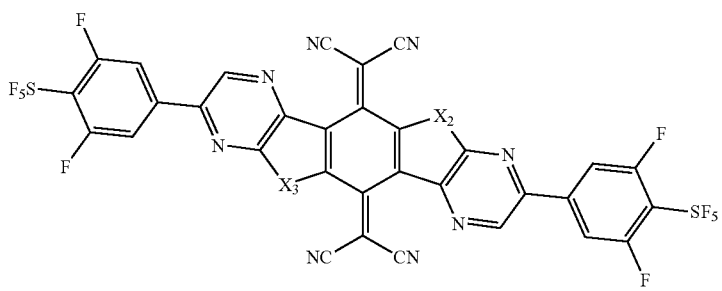
X₃ = X₂ = O compound BO-195
X₃ = X₂ = S compound BS-195
X₃ = X₂ = Se compound BSe-195

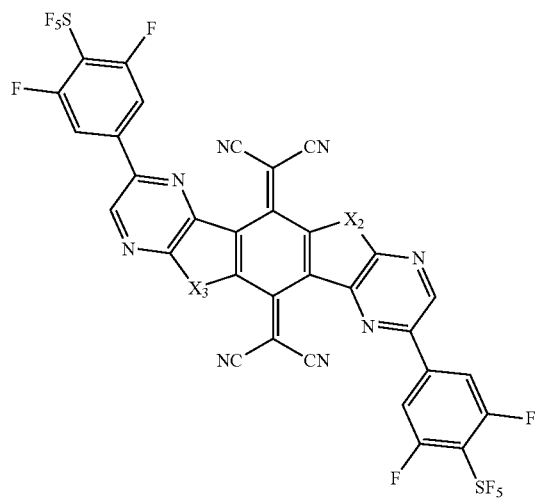
X₃ = X₂ = O compound BO-196
X₃ = X₂ = S compound BS-196
X₃ = X₂ = Se compound BSe-196
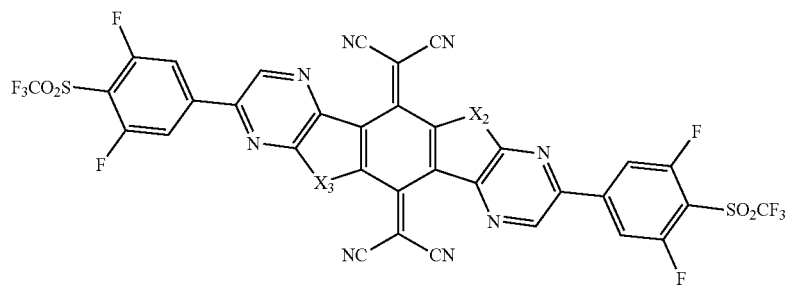
X₃ = X₂ = O compound BO-197
X₃ = X₂ = S compound BS-197
X₃ = X₂ = Se compound BSe-197
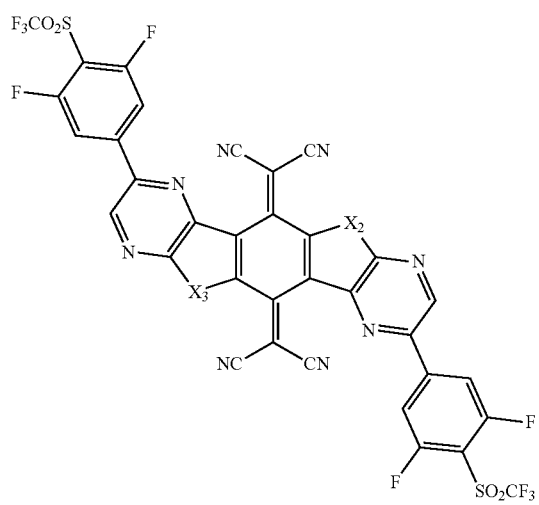
X₃ = X₂ = O compound BO-198
X₃ = X₂ = S compound BS-198
X₃ = X₂ = Se compound BSe-198

-continued

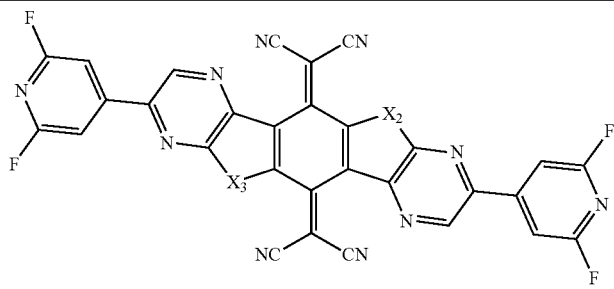

X₃ = X₂ = O compound BO-199
X₃ = X₂ = S compound BS-199
X₃ = X₂ = Se compound BSe-199.

12. The organic compound according to claim 11, wherein the organic compound is partially or completely deuterated.

13. A composition comprising the organic compound according to claim 1 and at least one material.

14. The composition according to claim 13, wherein the material is an aromatic amine compound.

15. An electroluminescent device comprising an anode, a cathode, and an organic layer disposed between the anode and the cathode, wherein the organic layer contains the organic compound according to claim 1.

16. The electroluminescent device according to claim 15, wherein the organic layer comprises at least one or two layers of a hole injection layer and a hole transporting layer.

17. The electroluminescent device according to claim 16, wherein the hole injection layer further comprises at least one material.

18. The electroluminescent device according to claim 16, wherein the hole injection layer further comprises at least one aromatic amine compound.

19. The electroluminescent device according to claim 16, wherein the hole transporting layer further comprises at least one material.

20. The electroluminescent device according to claim 16, wherein the hole transporting layer further comprises at least one aromatic amine compound.

* * * * *